(12) United States Patent
Ferrara Koller et al.

(10) Patent No.: US 11,286,300 B2
(45) Date of Patent: Mar. 29, 2022

(54) HUMANIZED ANTI-HUMAN CD19 ANTIBODIES AND METHODS OF USE

(71) Applicant: Hoffmann-La Roche Inc., Little Falls, NJ (US)

(72) Inventors: Claudia Ferrara Koller, Zug (CH); Guy Georges, Habach (DE); Alexander Haas, Weilheim (DE); Hubert Kettenberger, Munich (DE); Ekkehard Moessner, Kreuzlingen (CH); Tilman Schlothauer, Penzberg (DE); Michael Molhoj, Munich (DE); Laurent Lariviere, Munich (DE)

(73) Assignee: Hoffmann-La Roche Inc., Little Falls, NJ (US)

( * ) Notice: Subject to any disclaimer, the term of this patent is extended or adjusted under 35 U.S.C. 154(b) by 0 days.

(21) Appl. No.: 15/763,868

(22) PCT Filed: Sep. 30, 2016

(86) PCT No.: PCT/EP2016/073412
§ 371 (c)(1),
(2) Date: Mar. 28, 2018

(87) PCT Pub. No.: WO2017/055541
PCT Pub. Date: Apr. 6, 2017

(65) Prior Publication Data
US 2018/0282409 A1    Oct. 4, 2018

(30) Foreign Application Priority Data
Oct. 1, 2015  (EP) ..................................... 15187820

(51) Int. Cl.
| | | |
|---|---|---|
| C07K 16/00 | (2006.01) | |
| C12P 21/08 | (2006.01) | |
| A61K 39/395 | (2006.01) | |
| A61K 39/40 | (2006.01) | |
| C07K 16/28 | (2006.01) | |
| C07K 1/00 | (2006.01) | |

(52) U.S. Cl.
CPC ...... C07K 16/2803 (2013.01); *C07K 2317/24* (2013.01); *C07K 2317/33* (2013.01); *C07K 2317/56* (2013.01); *C07K 2317/565* (2013.01); *C07K 2317/732* (2013.01); *C07K 2317/734* (2013.01); *C07K 2317/92* (2013.01); *C07K 2317/94* (2013.01)

(58) Field of Classification Search
None
See application file for complete search history.

(56) References Cited

U.S. PATENT DOCUMENTS

| | | |
|---|---|---|
| 4,186,567 A | 2/1980 | Monden et al. |
| 4,676,980 A | 6/1987 | Segal et al. |
| 5,500,362 A | 3/1996 | Robinson et al. |
| 5,565,332 A | 10/1996 | Hoogenboom et al. |
| 5,571,894 A | 11/1996 | Wels et al. |
| 5,587,458 A | 12/1996 | King et al. |
| 5,591,828 A | 1/1997 | Bosslet et al. |
| 5,624,821 A | 4/1997 | Winter et al. |
| 5,648,260 A | 7/1997 | Winter et al. |
| 5,731,168 A | 3/1998 | Carter et al. |
| 5,821,333 A | 10/1998 | Carter et al. |
| 5,821,337 A | 10/1998 | Carter et al. |
| 5,869,046 A | 2/1999 | Presta et al. |
| 5,959,177 A | 9/1999 | Hein et al. |
| 5,969,108 A | 10/1999 | McCafferty et al. |
| 6,040,498 A | 3/2000 | Stomp et al. |
| 6,054,297 A | 4/2000 | Carter et al. |
| 6,171,586 B1 | 1/2001 | Lam et al. |
| 6,194,551 B1 | 2/2001 | Idusogie et al. |
| 6,248,516 B1 | 6/2001 | Winter et al. |
| 6,267,958 B1 | 7/2001 | Andya et al. |
| 6,417,429 B1 | 7/2002 | Hein et al. |
| 6,420,548 B1 | 7/2002 | Vezina et al. |
| 6,602,684 B1 | 8/2003 | Umana et al. |
| 6,737,056 B1 | 5/2004 | Presta |
| 6,809,185 B1 | 10/2004 | Schoonjans et al. |
| 6,818,418 B1 | 11/2004 | Lipovsek et al. |
| 6,982,321 B2 | 1/2006 | Winter |
| 7,087,409 B2 | 8/2006 | Barbas, III et al. |

(Continued)

FOREIGN PATENT DOCUMENTS

| | | |
|---|---|---|
| AU | 2011265482 B2 | 8/2013 |
| AU | 2013263717 B2 | 5/2016 |

(Continued)

OTHER PUBLICATIONS

The International Search Report and Written Opinion, dated Dec. 19, 2016, in the related PCT Appl. No. PCT/EP2016/073412.
The European Communication, dated Jan. 17, 2019, in the related European Appl. No. 16775243.5.
Chelius et al., "Identification and Characterization of Deamidation Sites in the Conserved Regions of Human Immunoglobulin Gamma Antibodies," Anal. Chem. Sep. 15, 2005, vol. 77, pp. 6004-6011.
The Indian Examination Report, dated May 1, 2020, in the related Indian Patent Appl. No. 201847010981.
The English translation of the Russian Office Action, dated Mar. 19, 2020, in the related Russian Patent Appl. No. 2018112563/10(019715).

(Continued)

*Primary Examiner* — Chun W Dahle

(57) ABSTRACT

Herein is reported an antibody that specifically binds to human CD 19, wherein the antibody comprises (a) HVR-H1 comprising the amino acid sequence of SEQ ID NO: 03, (b) HVR-H2 comprising the amino acid sequence of SEQ ID NO: 11, (c) HVR-H3 comprising the amino acid sequence of SEQ ID NO: 05, (d) HVR-L1 comprising the amino acid sequence of SEQ ID NO: 20 or 28, (e) HVR-L2 comprising the amino acid sequence of SEQ ID NO: 07, and (f) HVR-L3 comprising the amino acid sequence of SEQ ID NO: 08, as well as methods of using the same.

8 Claims, No Drawings
Specification includes a Sequence Listing.

(56) References Cited

U.S. PATENT DOCUMENTS

| | | |
|---|---|---|
| 7,125,978 B1 | 10/2006 | Vezina et al. |
| 7,166,697 B1 | 1/2007 | Galanis et al. |
| 7,250,297 B1 | 7/2007 | Beste et al. |
| 7,288,638 B2 | 10/2007 | Jure-Kunkel et al. |
| 7,332,581 B2 | 2/2008 | Presta |
| 7,371,826 B2 | 5/2008 | Presta |
| 7,521,541 B2 | 4/2009 | Eigenbrot et al. |
| 7,527,791 B2 | 5/2009 | Adams et al. |
| 7,632,925 B2 | 12/2009 | Kufer et al. |
| 7,659,384 B2 | 2/2010 | Jure-Kunkel et al. |
| 7,695,936 B2 | 4/2010 | Carter et al. |
| 8,097,703 B2 | 1/2012 | Rao-Naik et al. |
| 8,227,577 B2 | 7/2012 | Klein |
| 8,242,247 B2 | 8/2012 | Klein |
| 8,552,024 B2 | 10/2013 | Ackermann |
| 8,679,492 B2 | 3/2014 | Blein et al. |
| 8,703,132 B2 | 4/2014 | Imhof-Jung |
| 8,709,421 B2 | 4/2014 | Heiss |
| 8,796,424 B2 | 8/2014 | Croasdale |
| 8,945,571 B2 | 2/2015 | Ekkehard |
| 8,969,526 B2 | 3/2015 | Baehner |
| 9,011,847 B2 | 4/2015 | Bacac |
| 9,068,008 B2 | 6/2015 | Mossner |
| 9,266,938 B2 | 2/2016 | Ast |
| 9,266,967 B2 | 2/2016 | Klein et al. |
| 9,346,872 B2 | 5/2016 | Duerner et al. |
| 9,382,323 B2 | 7/2016 | Brinkmann et al. |
| 9,447,159 B2 | 9/2016 | Ast et al. |
| 9,481,730 B2 | 11/2016 | Bruenker |
| 9,526,797 B2 | 12/2016 | Gerdes et al. |
| 2003/0157108 A1 | 8/2003 | Presta |
| 2004/0093621 A1 | 5/2004 | Shitara et al. |
| 2004/0132028 A1 | 7/2004 | Stumpp et al. |
| 2004/0132066 A1 | 7/2004 | Balint et al. |
| 2005/0014934 A1 | 1/2005 | Hinton et al. |
| 2005/0123546 A1 | 6/2005 | Umana et al. |
| 2005/0260186 A1 | 11/2005 | Bookbinder et al. |
| 2006/0025576 A1 | 2/2006 | Miller et al. |
| 2006/0104968 A1 | 5/2006 | Bookbinder et al. |
| 2007/0111281 A1 | 5/2007 | Sondermann et al. |
| 2007/0224633 A1 | 9/2007 | Skerra et al. |
| 2008/0069820 A1 | 3/2008 | Fuh et al. |
| 2008/0139791 A1 | 6/2008 | Lipovsek et al. |
| 2008/0241152 A1 | 10/2008 | Alitalo et al. |
| 2009/0252683 A1 | 10/2009 | Kischel et al. |
| 2010/0015133 A1 | 1/2010 | Igawa et al. |
| 2010/0150918 A1 | 6/2010 | Kufer et al. |
| 2010/0215651 A1 | 8/2010 | Blein et al. |
| 2010/0316645 A1 | 12/2010 | Imhof-Jung et al. |
| 2011/0293613 A1 | 12/2011 | Brinkmann et al. |
| 2012/0225071 A1 | 9/2012 | Klein et al. |
| 2012/0276125 A1 | 11/2012 | Ast et al. |
| 2013/0022601 A1 | 1/2013 | Brinkmann et al. |
| 2013/0058936 A1 | 3/2013 | Bruenker et al. |
| 2013/0058937 A1 | 3/2013 | Auer et al. |
| 2013/0060011 A1 | 3/2013 | Bruenker et al. |
| 2013/0078249 A1 | 3/2013 | Ast et al. |
| 2013/0171095 A1 | 7/2013 | Bernett et al. |
| 2013/0287802 A1 | 10/2013 | Govindappa et al. |
| 2014/0044674 A1 | 2/2014 | Duerner et al. |
| 2014/0088295 A1 | 3/2014 | Smith et al. |
| 2014/0112914 A1 | 4/2014 | Nezu et al. |
| 2014/0154254 A1 | 6/2014 | Kannan et al. |
| 2014/0242079 A1 | 8/2014 | Bacac et al. |
| 2014/0242080 A1 | 8/2014 | Jaeger et al. |
| 2014/0288275 A1 | 9/2014 | Moore et al. |
| 2014/0294823 A1 | 10/2014 | Moore et al. |
| 2014/0294833 A1 | 10/2014 | Desjarlais et al. |
| 2014/0302064 A1 | 10/2014 | Moore |
| 2014/0322217 A1 | 10/2014 | Moore et al. |
| 2014/0363426 A1 | 12/2014 | Moore et al. |
| 2014/0370013 A1 | 12/2014 | Desjarlais et al. |
| 2014/0370019 A1 | 12/2014 | Bruenker et al. |
| 2014/0377270 A1 | 12/2014 | Moore et al. |
| 2015/0166661 A1 | 6/2015 | Chen et al. |
| 2015/0218244 A1 | 8/2015 | Emrich et al. |
| 2015/0274845 A1 | 10/2015 | Bruenker et al. |
| 2015/0315296 A1 | 11/2015 | Schaefer et al. |
| 2015/0368351 A1 | 12/2015 | Vu et al. |
| 2015/0376287 A1 | 12/2015 | Vu et al. |
| 2016/0060356 A1 | 3/2016 | Bacac et al. |
| 2016/0060357 A1 | 3/2016 | Bacac et al. |
| 2016/0075785 A1 | 3/2016 | Ast et al. |
| 2016/0130347 A1 | 5/2016 | Bruenker et al. |
| 2016/0145354 A1 | 5/2016 | Bacac et al. |
| 2016/0159917 A1 | 6/2016 | Bruenker et al. |
| 2016/0175397 A1 | 6/2016 | Umana et al. |
| 2016/0200833 A1 | 7/2016 | Amann et al. |
| 2016/0208017 A1 | 7/2016 | Ast et al. |
| 2016/0208019 A1 | 7/2016 | Bacac et al. |
| 2016/0263240 A1 | 9/2016 | Ast et al. |
| 2016/0297881 A1 | 10/2016 | Vu et al. |
| 2016/0340399 A1 | 11/2016 | Amann et al. |
| 2016/0340413 A1 | 11/2016 | Duerner et al. |
| 2016/0368985 A1 | 12/2016 | Hotzel et al. |
| 2017/0008971 A1 | 1/2017 | Dennis et al. |
| 2017/0096485 A1 | 4/2017 | Bacac et al. |
| 2017/0096495 A1 | 4/2017 | Bacac et al. |
| 2017/0114141 A1 | 4/2017 | Amann et al. |
| 2017/0114146 A1 | 4/2017 | Klein et al. |
| 2017/0129962 A1 | 5/2017 | Regula et al. |
| 2017/0174786 A1 | 6/2017 | Bacac et al. |
| 2017/0190783 A1 | 7/2017 | Bacac et al. |
| 2017/0209573 A1 | 7/2017 | Bacac et al. |
| 2017/0247467 A1 | 8/2017 | Amann et al. |
| 2017/0253670 A1 | 9/2017 | Klein et al. |
| 2017/0267783 A1 | 9/2017 | Nezu et al. |
| 2017/0306018 A1 | 10/2017 | Vu et al. |
| 2017/0306036 A1 | 10/2017 | Vu et al. |
| 2017/0306044 A1 | 10/2017 | Vu et al. |
| 2017/0327579 A1 | 11/2017 | Vu et al. |
| 2017/0327580 A1 | 11/2017 | Vu et al. |
| 2017/0349668 A1 | 12/2017 | Rattel et al. |
| 2018/0230215 A1 | 8/2018 | Hofer et al. |
| 2018/0282409 A1 | 10/2018 | Ferrara Koller et al. |
| 2019/0016771 A1 | 1/2019 | Amann et al. |
| 2019/0120682 A1 | 4/2019 | Ziegler et al. |
| 2019/0194291 A1 | 6/2019 | Bruenker et al. |
| 2019/0211113 A1 | 7/2019 | Amann et al. |
| 2020/0190206 A1 | 6/2020 | Ferrara Koller et al. |
| 2020/0199234 A1 | 6/2020 | Georges et al. |
| 2020/0325225 A1 | 10/2020 | Bacac et al. |
| 2020/0325238 A1 | 10/2020 | Bacac et al. |

FOREIGN PATENT DOCUMENTS

| | | |
|---|---|---|
| CN | 106279434 A | 1/2017 |
| EP | 1641818 B1 | 12/2008 |
| EP | 1691833 B1 | 3/2010 |
| EP | 2578230 A1 | 4/2013 |
| EP | 2647707 A1 | 10/2013 |
| EP | 2995626 A1 | 3/2016 |
| EP | 1870459 B1 | 6/2016 |
| WO | 9103493 A1 | 3/1991 |
| WO | 9201059 A1 | 1/1992 |
| WO | 9301161 A1 | 1/1993 |
| WO | 9308829 A1 | 5/1993 |
| WO | 9316185 A2 | 8/1993 |
| WO | 9429351 A2 | 12/1994 |
| WO | 9601126 A1 | 1/1996 |
| WO | 9627011 A1 | 9/1996 |
| WO | 9640210 A1 | 12/1996 |
| WO | 9730087 A1 | 8/1997 |
| WO | 9850431 A2 | 11/1998 |
| WO | 9858964 A1 | 12/1998 |
| WO | 9922764 A1 | 5/1999 |
| WO | 9951642 A1 | 10/1999 |
| WO | 9954440 A1 | 10/1999 |
| WO | 0209573 A2 | 2/2002 |
| WO | 0220565 A2 | 3/2002 |
| WO | 0234661 A2 | 5/2002 |
| WO | 03011878 A2 | 2/2003 |
| WO | 2003048209 A1 | 6/2003 |
| WO | 2004035607 A2 | 4/2004 |

(56) References Cited

FOREIGN PATENT DOCUMENTS

| | | |
|---|---|---|
| WO | 2004039841 A2 | 5/2004 |
| WO | 2004056312 A2 | 7/2004 |
| WO | 2004069876 A2 | 8/2004 |
| WO | 2004106381 A1 | 12/2004 |
| WO | 2005012493 A2 | 2/2005 |
| WO | 2005044859 A2 | 5/2005 |
| WO | 2005056764 A2 | 6/2005 |
| WO | 2005061547 A2 | 7/2005 |
| WO | 2005100402 A1 | 10/2005 |
| WO | 2005103081 A2 | 11/2005 |
| WO | 2006029879 A2 | 3/2006 |
| WO | 2006044908 A2 | 4/2006 |
| WO | 2006050949 A2 | 5/2006 |
| WO | 2006076651 A2 | 7/2006 |
| WO | 2006082515 A2 | 8/2006 |
| WO | 2006089133 A2 | 8/2006 |
| WO | 2006099875 A1 | 9/2006 |
| WO | 2006121168 A1 | 11/2006 |
| WO | 2006121810 A2 | 11/2006 |
| WO | 2007000675 A2 | 1/2007 |
| WO | 2007002223 A2 | 1/2007 |
| WO | 2007014744 A2 | 2/2007 |
| WO | 2007024715 A2 | 3/2007 |
| WO | 2007031875 A2 | 3/2007 |
| WO | 2007042261 A2 | 4/2007 |
| WO | 2007071422 A2 | 6/2007 |
| WO | 2007071426 A1 | 6/2007 |
| WO | 2007075270 A2 | 7/2007 |
| WO | 2007110205 A2 | 10/2007 |
| WO | 2007146968 A2 | 12/2007 |
| WO | 2007147901 A1 | 12/2007 |
| WO | 2008022152 A2 | 2/2008 |
| WO | 2008031056 A2 | 3/2008 |
| WO | 2008098796 A1 | 8/2008 |
| WO | 2008119566 A2 | 10/2008 |
| WO | 2008119567 A2 | 10/2008 |
| WO | 2009000538 A1 | 12/2008 |
| WO | 2009012268 A1 | 1/2009 |
| WO | 2009018386 A1 | 2/2009 |
| WO | 2009040550 A1 | 4/2009 |
| WO | 2009054863 A2 | 4/2009 |
| WO | 2009070642 A1 | 6/2009 |
| WO | 2009080251 A1 | 7/2009 |
| WO | 2009080252 A1 | 7/2009 |
| WO | 2009080253 A1 | 7/2009 |
| WO | 2009080254 A1 | 7/2009 |
| WO | 2009089004 A1 | 7/2009 |
| WO | 2010010051 A1 | 1/2010 |
| WO | 2010095031 A2 | 8/2010 |
| WO | 2010115589 A1 | 10/2010 |
| WO | 2010129304 A2 | 11/2010 |
| WO | 2010136172 A1 | 12/2010 |
| WO | 2010145792 A1 | 12/2010 |
| WO | 2010145793 A1 | 12/2010 |
| WO | 2011020783 A2 | 2/2011 |
| WO | 2011028952 A1 | 3/2011 |
| WO | 2011076683 A1 | 6/2011 |
| WO | 2011090754 A1 | 7/2011 |
| WO | 2011090762 A1 | 7/2011 |
| WO | 2011100403 A1 | 8/2011 |
| WO | 2011109789 A2 | 9/2011 |
| WO | 2011143545 A1 | 11/2011 |
| WO | 2011147834 A1 | 12/2011 |
| WO | 2012010561 A1 | 1/2012 |
| WO | 2012020006 A2 | 2/2012 |
| WO | 2012058768 A1 | 5/2012 |
| WO | 2012130471 A1 | 10/2012 |
| WO | 2012130831 A1 | 10/2012 |
| WO | 2012158818 A2 | 11/2012 |
| WO | 2012162067 A2 | 11/2012 |
| WO | 2013019906 A1 | 2/2013 |
| WO | 2013026831 A1 | 2/2013 |
| WO | 2013026833 A1 | 2/2013 |
| WO | 2013026837 A1 | 2/2013 |
| WO | 2013092001 A1 | 6/2013 |
| WO | 2013096291 A2 | 6/2013 |
| WO | 2013120929 A1 | 8/2013 |
| WO | 2013157953 A1 | 10/2013 |
| WO | 2013157954 A1 | 10/2013 |
| WO | 2014012085 A2 | 1/2014 |
| WO | 2014022540 A1 | 2/2014 |
| WO | 2014028560 A2 | 2/2014 |
| WO | 2014047231 A1 | 3/2014 |
| WO | 2014081955 A1 | 5/2014 |
| WO | 2014100762 A1 | 6/2014 |
| WO | 2014116846 A2 | 7/2014 |
| WO | 2014122251 A2 | 8/2014 |
| WO | 2014131694 A1 | 9/2014 |
| WO | 2014131711 A1 | 9/2014 |
| WO | 2014131712 A1 | 9/2014 |
| WO | 2014141152 A2 | 9/2014 |
| WO | 2014151910 A1 | 9/2014 |
| WO | 2014153002 A1 | 9/2014 |
| WO | 2014161845 A1 | 10/2014 |
| WO | 2014177460 A1 | 11/2014 |
| WO | 2014180754 A1 | 11/2014 |
| WO | 2014191113 A1 | 12/2014 |
| WO | 2015006749 A2 | 1/2015 |
| WO | 2015048272 A1 | 4/2015 |
| WO | 2015095392 A1 | 6/2015 |
| WO | 2015101588 A1 | 7/2015 |
| WO | 2015103072 A1 | 7/2015 |
| WO | 2015150447 A1 | 10/2015 |
| WO | 2015183902 A1 | 12/2015 |
| WO | 2015184203 A1 | 12/2015 |
| WO | 2016020065 A1 | 2/2016 |
| WO | 2016020309 A1 | 2/2016 |
| WO | 2016030350 A1 | 3/2016 |
| WO | 2016036678 A1 | 3/2016 |
| WO | 2016048938 A1 | 3/2016 |
| WO | 2016079076 A1 | 5/2016 |
| WO | 2016079081 A1 | 5/2016 |
| WO | WO-2016075278 A1 * | 5/2016 ......... C07K 16/2815 |
| WO | 2016110576 A1 | 7/2016 |
| WO | 2016156291 A1 | 10/2016 |
| WO | 2016166629 A1 | 10/2016 |
| WO | 2016177802 A1 | 11/2016 |
| WO | 2016179003 A1 | 11/2016 |
| WO | 2016184882 A1 | 11/2016 |
| WO | 201755391 A1 | 4/2017 |
| WO | 201755398 A2 | 4/2017 |
| WO | 2017055328 A1 | 4/2017 |
| WO | 2017055541 A1 | 4/2017 |
| WO | 2017060144 A1 | 4/2017 |
| WO | 2017072207 A1 | 5/2017 |
| WO | 2017180913 A2 | 10/2017 |
| WO | 2018114748 A1 | 6/2018 |
| WO | 2018114754 A1 | 6/2018 |
| WO | 2018127473 A1 | 7/2018 |
| WO | 2018177966 A1 | 10/2018 |
| WO | 2018177967 A1 | 10/2018 |
| WO | 2019154890 A1 | 8/2019 |

OTHER PUBLICATIONS

The English translation of the Indonesian Office Action, dated Mar. 12, 2020, in the related Indonesian Patent Appl. No. PID201802285.

Kellner et al., "The Fc-engineered CD19 antibody MOR208 (XmAb5574) induces natural killer cell-mediated lysis of acute lymphoblastic leukemia cells from pediatric and adult patients," Leukemia, Dec. 31, 2012, 27(7): pp. 1595-1598.

Nishimoto, et al., "Costimulation of mast cells by 4-1BB, a member of the tumor necrosis factor receptor superfamily, with the high-affinity IgE receptor" Blood 106:4241-4248 (2005).

N. Zhang et al., "Targeted and Untargeted CD137L Fusion Proteins for the Immunotherapy of Experimental Solid Tumors," Clinical Cancer Research 13(9):2758-2767 (Jan. 28, 2010).

Olofsson, et al., "CD137 is Expressed in Human Atherosclerosis and Promotes Development of Plaque inflammation in Hypercholesterolemic Mice" Circulation 117:1292-1301 (2008).

Osbourn, J., et al., "From rodent reagents to human therapeutics using antibody guided selection" METHODS 36:61-68 (May 1, 2005).

(56) References Cited

OTHER PUBLICATIONS

Oshimi et al., "Increased lysis of patient CD10-positive leukemic cells by T cells coated with anti-CD3 Fab' antibody cross-linked to anti-CD10 Fab' antibody," Blood. 77(5):1044-9 (1991).
Pace et al., "How to measure and predict the molar absorption coefficient of a protein," Protein Science, 1995, vol. 4, pp. 2411-1423.
Padlan, "A Possible Procedure for Reducing the Immunogenicity of Antibody Variable Domains While Preserving Their Ligand-Binding Properties," Mol Immunol, (19910000), vol. 28, pp. 489-498.
Padlan, "Anatomy of the Antibody Molecule," Molec Immun, 1994, vol. 113, No. 3, pp. 169-217.
Palazon er al., "Agonist Anti-CD 137 mAb Act on Tumor Endothelial Cells to Enhance Recruitment of Activated T Lymphocytes" Cancer Research 71:801-811 (2011).
Parker et al., "Antibody mimics based on human fibronectin type three domain engineered for thermostability and high-affinity binding to vascular endothelial growth factor receptor two," Protein Engineering, Design & Selection vol. 18 No. 9 pp. 435-444, 2005.
Pauly S. et al., "CD137 is expressed by follicular dendritic cells and costimulates B lymphocyte activation in germinal centers," J Leukoc Biol., 2002, vol. 72, No. 1, pp. 35-42.
The International Search Report and Written Opinion, dated Dec. 20, 2016, in related PCT Appl. No. PCT/EP2016/073041.
Pedersen et al., "A Naturally Occurring HER2 Carboxy-Terminal Fragment Promotes Mammary Tumor Growth and Metastasis," Mol Cell Biol, 2009, vol. 29, pp. 3319-3331.
Pessano et al., "The T3/T cell receptor complex: antigenic distinction between the two 20-kd T3 (T3-delta and T3-epsilon) subunits," Embo J. 4(2);337-44 (1985).
Petkova, S.B. et al., "Enhanced half-life of genetically engineered human IgG 1 antibodies in a humanized FcRn mouse model: potential application in humorally mediated autoimmune disease," Int'l. Immunol., 2006, vol. 18, No. 12, pp. 1759-1769.
Philippe et al., "Multiple myeloma—translation of trial results into reality," The Lancet, 20160707, vol. 388, Nr: 10040, pp. 111-113.
Pieris Pharmaceuticals, "Pieris Pharmaceuticals Presents Positive Data for Its Lead Bispecific Drug Candidate, PRS-343, at the 2016 CRI- CIMT-EATI-AACR International Cancer Immunotherapy Conference Novel 4-1BB/HER2 Bispecific Demonstrates Differentiation Over Conventional 4-1BB mAb and HER2 mAb Approaches," Sep. 26, 2016.
Pliickthun et al. The Pharmacology of Monoclonal Antibodies "Antibodies front_ *Escherichia coli*" (Antibodies front *Escherichia coli*). Rosenberg N loore.:269-315 (1994).
Ponsel et al., "High affinity, developability and functional size: the holy grail of combinatorial antibody library generation," Molecules, Jan. 1, 2011, vol. 16, Nr: 5, pp. 3675-3700.
Poppema, S.; Visser, L., "Preparation and Application of Monoclonal Antibodies: B Cell Panel and Paraffin Tissue Reactive Panel," Biotest Bulletin, 1987, vol. 3, pp. 131-139.
Queen et al., "A humanized antibody that binds to the interleukin 2 receptor," Proc Natl Acad Sci USA, 1989, vol. 86, pp. 10029-10033.
Rabu et al., "Production of Recombinant Human Trimeric CD137L (4-1BBL) Cross-Linking is Essential To Its T Cell Co-Stimulation Activity" J. Biol. Chem. 280:41472-41481 (2005).
Rajpal et al., "A general method for greatly improving the affinity of antibodies by using combinatorial libraries," Proceedings of the National Academy of Sciences (PNAS), Jun. 1, 2005, vol. 102, Nr: 24, pp. 8466-8471.
Ravetch, J.V.; Kinet, J.P., "Fc Receptors," Annu. Rev. Immunol., 1991, vol. 9, pp. 457-492.
Reusch et al., "A tetravalent bispecific TandAb (CD19/CD3), AFM11, efficiently recruits T cells for the potent lysis of CD19(+) tumor cells," MAbs. 7(3):584-604 (2015) (22 pages).
Riechmann et al., "Reshaping human antibodies for therapy," Nature, 1988, vol. 332, pp. 323-329.

Ridgway, et al., "Knobs-Into-Holes' Engineering of Antibody CH3 Domains for Heavy Chain Heterodimerization," Protein Engineering, Jan. 1, 1996, vol. 9, Nr: 7, pp. 617-621.
Riedle et al. "In vivo activation and expansion of T cells by a bi-specific antibody abolishes metastasis formation of human melanoma cells in SLID mice," Int J Cancer. 75(6):908-18 (1998).
Roguska et al., "A Comparison of Two Murine Monoclonal Antibodies Humanized By CDR-Grafting and Variable Domain Resurfacing," Protein Engineering, Jan. 1, 1996, vol. 9, Nr: 10, pp. 895-904.
Hornig et al., "Combining antibody-directed presentation of IL-15 and 4-1BBL in a trifunctional fusion protein for cancer mmunotherapy," Molecular Cancer Therapeutics, American Association for Cancer Research, vol. 13, Nr: 1, pp. 112-121, Jan. 1, 2014.
Hornig et al., "Evaluating combinations of costimulatory antibody-ligand fusion proteins for targeted cancer Immunotherapy" Can Immunol Immunotherapy:1369-1380 (May 17, 2013).
Huston, J.S., "[3] Protein Engineering of Single-Chain Fv Analogs and Fusion Proteins," Methods in Enzymol., vol. 203, pp. 46-88, 1991.
Hudson et al., "Engineered antibodies," Nat Med, vol. 9, pp. 129-134, 2003.
Hui et al., "T cell costimulatory receptor CD28 is a primary target for PD-1-mediated inhibition", Science, vol. 355, pp. 1428-1433, 2017.
Hunig, T., "The storm has cleared: lessons from the CD28 superagonist TGN1412 trial", Nat Rev Immunol, vol. 12, pp. 317-318, 2012.
Idusogie et al., "Mapping of the C1q Binding Site on Rituxan, a Chimeric Antibody with a Human IgG1 Fc," J. Immunol., vol. 164, pp. 4178-4184, 2000.
Ingle et al., "High CD21 expression inhibits internalization of anti-CD 19 antibodies and cytotoxicity of an anti-CD19-drug conjugate", Br J Haematol, vol. 140, pp. 46-58, 2008.
Inoue, S.Nambu T.Shimomura T., "The RAIG family member, GPRC5D, is associated with hard-keratinized structures", J Invest Dermatol., vol. 122, No. 3, pp. 565-573, 2004.
Jendeberg et al., "Engineering of Fc(1) and Fc(3) from human immunoglobulin G to analyse subclass specificity for staphylococcal protein A," J Immunol Methods, Feb. 14, 1997;201(1):25-34.
Jones et al., "Replacing the complementaritydetermining regions in a human antibody with those from a mouse," Nature, vol. 321, pp. 522-525, 1986.
Ju S.A et al., "Eradication of established renal cell carcinoma by a combination of 5-fluorouracil and anti-4-1BB monoclonal antibody in mice." Int J Cancer 122:2784-2790. (2008).
June, C.H.Ledbetter, J.A.Gillespie, M.M.Lindsten, T.Thompson, C.B., "T-cell proliferation involving the CD28 pathway is associated with cyclosporine-resistant interleukin 2 gene expression", Mol Cell Biol, vol. 7, pp. 4472-4481, 1987.
Irving et al., "Ribosome display and affinity maturation: from antibodies to single V-domains and steps towards cancer therapeutics," Journal of Immunological Methods, vol. 248, No. 1-2, pp. 31-45, 2001.
Kabat et al., Sequences of Proteins of Immunological Interest, National Institutes of Health, (1991), pp. 647-660.
Kabat et al. U.S. Dept. of Health and Human Services, Public Health Services, NIH Publ. No. 91-3242:3 "'Sequences of Proteins of Immunological Interest" (1983).
Kam, N.W. et al., "Carbon nanotubes as multifunctional biological transporters and near-infared agents for selective cancer cell destruction," Proc. Natl. Acad. Sci. USA, vol. 102, pp. 11600-11605, 2005.
Kamphorst et al., "Rescue of exhausted CD8 T cells by PD-1-targeted therapies is CD28-dependent," Science, vol. 355, Nr: 6332, pp. 1423-1427, Mar. 31, 2017.
Kashmiri, S., et al., "SDR grafting—a new approach to antibody humanization" Methods 136:25-34 (Jan. 1, 2005).
Kermer et al., "Combining antibody-directed presentation of IL-15 and 4-1BBL in a trifunctional fusion protein for Dancer immunotherapy," Molecular Cancer Therapeutics, 20140101 American Association for Cancer Research, vol. 13, Nr:1, pp. 112-121.
Kienzle et al., "CD137 (ILA/4-1BB), expressed by primary human monocytes, induces monocyte activation and apoptosis of B lymphocytes" International Immonology 12:73-82 (2000).

(56) References Cited

OTHER PUBLICATIONS

Kim et al., "4-1BB Engagement Costimulates NKT Cell Activation and Exacerbates NKT Cell Ligand-Induced Airway Hyper-responsivenss and Inflammation" J Immunol 180:2062-2068 (2008).
Kim, J.K. et al., "Localization of the site of the murine IgG1 molecule that is involved Li Wilding to tai 3 murine intestinal Fc receptor," J. Immunol., vol. 24, pp. 2429-2434, 1994.
Kim, Y. H. et al., "Mechanisms involved in synergistic anticancer effects of anti-4-1BB and cyclophosphamide therapy." Mol Cancer Ther 8:469-478 (2009).
Kindt et al., Kuby Immunology, W.H. Freeman and Co., p. 91, 2007.
Kipriyanov et al., "Bispecific CD3 × CD19 diabody for T cell-mediated lysis of malignant human B cells," Int J Cancer. 77(5)1763-72 (1998).
Kipriyanov et al., "Bispecific tandem diabody for tumor therapy with improved antigen binding and pharmacokinetics," J Mol Biol. 293(1)141-56 (1999).
Klein et al., "Progress in overcoming the chain association issue in bispecific heterodimeric IgG antibodies," MAbs. 4(6)1653-63 (2012).
Klein et al., "Epitope interactions of monoclonal antibodies targeting CD20 and their relationship to functional properties," mAbs, vol. 5, pp. 22-33, 2013.
Klimka et al., "Human anti-CD30 recombinant antibodies by guided phage antibody selection using cell panning," Br J Cancer, vol. 83, pp. 252-260, 2000.
Kontermann, "Dual targeting strategies with bispecific antibodies," MAbs. 4(2):182-97 (2012).
Kostelny et al., "Formation of a Bispecific Antibody By the Use of Leucine Zippers," J. Immunol., vol. 148, No. 5, pp. 1547-1553, Mar. 1, 1992.
Kwajah M.; Schwarz H., "CD137 ligand signaling induces human monocyte to dendritic cell differentiation," Eur J Immunol., 2010, vol. 40, No. 7, pp. 1938-1949.
Kwon et al., "cDNA sequences of two inducible T-cell genes" P Natl Acad Sci USA 86:1963-1967, Mar. 1989.
Langstein J. et al., "CD137 (ILA/4-1BB), a Member of the TNF Receptor Family, Induces Monocyte Activation via Bidirectional Signaling," J Immunol., 1998, vol. 160, No. 5, pp. 2488-2494.
Lavin et al., "Innate Immune Landscape in Early Lung Adenocarcinoma by Paired Single-Cell Analyses", Cell, May 4, 2017, vol. 169, pp. 750-765 e717.
Lee et al., "Combinatorial therapy for liver metastatic colon cancer: dendritic cell vaccine and low-dose agonistic anti-4-1BB antibody costimulatory signal" J Surg Res 169:e43-50 (2011).
Levitsky V. et al., "The clonal composition of a peptide-specific oligoclonal CTL repertoire selected in response to persistent EBV infection is stable over time." J Immunol 161:594-601 (1998).
Li et al., "Inhibitory Fcγ Receptor Engagement Drives Adjuvant and Anti-Tumor Activities of Agonistic CD40 Antibodies" Science 333:1030-1034 (2011).
Li et al., "Optimization of humanized IgGs in glycoengineered Pichia pastoris," Nat Biotech, vol. 24, pp. 210-215, Jan. 22, 2006.
Liljeblad, Mathias et al., "Analysis of agalacto-IgG in rheumatoid arthritis using surface plasmon resonance" Glycocon.Jugate J 17:323-329 (Jul. 14, 2000).
Lin et al., "Fc-dependent expression of CD137 on human NK cells: insights into agonistic effects of anti-CD137 monoclonal antibodies" Blood 112:699-707 (2008).
Linsley et al., "T-Cell Antigen CD28 Mediates Adhesion With B Cells By Interacting With Activation Antigen B7/BB-1," Proceedings of the National Academy of Sciences (PNAS), Jul. 1, 1990, vol. 87, pp. 5031-5035.
Liu et al., "Efficient inhibition of human B-cell lymphoma in SCID mice by synergistic antitumor effect of human 4-1BB ligand/anti-CD20 fusion proteins and anti-CD3/anti-CD20 diabodies," Journal of immunotherapy, Jun. 1, 2010, vol. 33, Nr: 5, pp. 500-509.
Lonberg, "Fully human antibodies from transgenic mouse and phage display platforms" Current Opin Immunol 20:450-459, 2008.
Lonberg, "Human antibodies from transgenic animals," Nat Biotech, (20050000), vol. 23, pp. 1117-1125.
Luiten et al., "Chimeric bispecific OC/TR monoclonal antibody mediates lysis of tumor cells expressing the folate-binding protein (MOv18) and displays decreased immunogenicity in patients," J Immunother. 20(6):496-504 (1997).
Lum et al., "CD20-Targeted T Cells after Stem Cell Transplantation for High Risk and Refactory Non-Hodgkin's Lymphoma," Biology of Blood and Marrow Transplantation, Mar. 22, 2013, vol. 19, Nr: 6, pp. 925-933.
Lum et al., "Targeting CD138-/CD20+ Clonogenic Myeloma Precursor Cells Decreases These Cells and Induces Transferable Antimyeloma Immunity," Biology of Blood and Marrow Transplantation, Jan. 28, 2016, vol. 22, Nr: 5, pp. 869-878.
MacCallum et al., "Antibody-antigen interactions: contact analysis and binding site topography," J. Mol. Biol., (19960000), vol. 262, pp. 732-745.
MacEwan et. al. et al., "TNF ligands and receptors—a matter of life and death." Brit J Pharmacol 135(4):855-875, Feb. 2002.
Manzke, O. et al., "Locoregional Treatment of Low-Grade B-Cell Lymphoma With CD3 XCD19 Bispecific Antibodies and CD28 Costimulation: II Assessment of Cellular Immune Responses," Int. J. Cancer, (2001), vol. 91, pp. 516-522.
Mariuzza et al., "The Structural Basis of Antigen-Antibody Recognition," Annual Review of Biophysics and Biophysical Chemistry, vol. 16:139-159, Jun. 1987.
Marshall J., "Carcinoembryonic Antigen-Based Vaccines," Semin Oncol., (20030000), vol. 30, No. 8, pp. 30-36.
Mather et al., "Culture of Testicular Cells in Hormone-Supplemented Serum-Free Medium," Annals N.Y. Acad Sci, 1982, vol. 383, pp. 44-68.
Mather, "Establishment and Characterization of Two Distinct Mouse Testicular Epithelial Cell Lines," Biol Reprod, 1980, vol. 23, pp. 243-251.
McCafferty, J., et al., "Phage Antibodies: Filamentous Phage Displaying Antibody Variable Domains" Nature 348:552-554 (Dec 6. 1990).
Melero et al., "Monoclonal Antibodies Against the 4-1BB T-cell Activation Molecule Eradicate Established Tumors" Nature Medicine 3(6):682-685 (1997).
Melero et al., "NK1.1 Cells Express 4-1BB (CDw137) Costimulatory Molecule and are Required for Tumor Immunity Elicited by Anti-4-1BB Monoclonal Antibodies" Cellular Immunology 190:167-172 (1998).
Merchant et al., "An efficient route to human bispecific IgG" Nat Biotechnol 16(7):677-681 (1998).
Miller et al., "Design, construction, and in vitro analyses of multivalent antibodies," J Immunol. 170(9):4854-61 (2003).
Milstein; Cuello, "Hybrid hybridomas and their use in immunohistochemistry," Nature, 1983, vol. 305, p. 537.
Moore et al., "A novel bispecific antibody format enables simultaneous bivalent and monovalent co-engagement of distinct target antigens," MAbs. 3(6):546-57 (2011).
Moore et al.," Application of dual affinity retargeting molecules to achieve optimal redirected T-cell killing of B-cell lymphoma", Blood, (2011), vol. 117, pp. 4542-4551 (11 pages).
Morales-Kastresana, A. et al., "Combined immunostimulatory monoclonal antibodies extend survival in an aggressive transgenic hepatocellular carcinoma mouse model." Clin Cancer Res 19:6151-6162 (2013).
Morales-Kastresana, A., et al., "Essential complicity of perforin-granzyme and FAS-L mechanisms to achieve tumor rejection following treatment with anti-CD137 mAb" J Immunother Cancer 1(3):1-6 (May 29, 2013).
Morea, V. et al., "Antibody Modeling: Implications for Engineering and Design," Methods, vol. 20, No. 3, pp. 267-279, 2000.
Morrison et al., "Chimeric human antibody molecules: Mouse antigen-binding domains with human constant region domains," Proc Natl Acad Sci, 1984, vol. 81, pp. 6851-6855.
Morrison, "Genetically Engineered Antibody Molecules," Adv Immunol, 1988, vol. 44, pp. 65-92.
Mueller et al., "Activity of soluble OX40 ligand is enhanced by oligomerization and cell surface immobilization" FEBS J. 275:2296-2304 (2008).

(56) References Cited

OTHER PUBLICATIONS

Müller et al., "A novel antibody-4-1BBL fusion protein for targeted costimulation in cancer immunotherapy," Journal of Immunotherapy, vol. 31, Nr: 8, pp. 714-722. (Oct. 1, 2008).
Murillo et al., "In vivo depletion of DC impairs the anti-tumor effect of agonistic anti-CD137 mAb" Eur. J. Immunol. 39:2424-2436 (2009).
Murray et al., "CD28-mediated pro-survival signaling induces chemotherapeutic resistance in multiple myeloma," Blood, Jun. 12, 2014, vol. 123, Nr: 24, pp. 3770-3779.
Nagorsen et al., "Immunomodulatory therapy of cancer with T cell-engaging BiTE antibody blinatumomab," Exp Cell Res. 317(9):1255-60 (2011).
Nap et al., "Specificity and Affinity of Monoclonal Antibodies against Carcinoembryonic Antigen," Cancer Res., 1992, vol. 52, No. 8, pp. 2329-2339.
Nap et al., "Immunohistochemistry of Carcino-Embryonic Antigen in the Embryo, Fetus and Adult," Tumour Biol., 1988, vol. 9, No. 2-3, pp. 145-153.
Narazaki et al., "CD137 agonist antibody prevents cancer recurrence: contribution of CD137 on both hematopoietic and nonhematopoietic cells" Blood 115:1941-1948 (2010).
Necela et al., "Folate Receptor-α (FOLR1) Expression and Function in Triple Negative Tumors," PloS One, Mar. 27, 2015, vol. 10, No. 3, p. e0127133.
Neumaier et al., "Monoclonal Antibodies for Carcinoembryonic Antigen (CEA) as a Model System: Identification of Two Novel CEA-Related Antigens in Meconium and Colorectal Carcinoma. Tissue by Western Blots and Differential Immunoaffinity Chromatography" J Immunol 135(5):3604-3609 (Nov 5. 1985).
N. Hornig et al., "Combination of a Bispecific Antibody and Costimulatory Antibody-Ligand Fusion Proteins for Targeted Cancer Immunotherapy," Journal of Immunotherapy 35(5):418-429 (Jun. 1, 2012).
Aggarwal et al., "Signalling pathways of the TNF superfamily: a double-edged sword" Nat Rev Immunol 3(9):745-756 (Sep. 2003).
Anido et al., "Biosynthesis of tumorigenic HER2 C-terminal fragments by alternative initiation of translation, "EMBO J, vol. 25, pp. 3234-3244, 2006.
Ascierto P. et al., "Clinical Experiences With Anti-CD137 and Anti-PD1 Therapeutic Antibodies" Seminars in Oncology 27(5):508-516 (Oct. 2010).
Atwell et al., "Stable heterodimers from remodeling the domain interface of a homodimer using a phage display ibrary," J Mol Biol. 270(1):26-35 (1997).
Ausubel et al., "Current Protocols in Molecular Biology," Greene and Wiley Interscience, New York. (1987).
Bacher P. et al., "Antigen-specific expansion of human regulatory T cells as a major tolerance mechanism against mucosal fungi," Mucosal Immunol., (20140000), vol. 7, No. 4, pp. 916-928.
Baessler T., "CD137 ligand mediates opposite effects in human and mouse NK cells and impairs NK-cell reactivity against human acute myeloid leukemia cells," Blood, vol. 115, No. 15, pp. 3058-3069, 2010.
Bahlis et al., "CD28-mediated regulation of multiple myeloma cell proliferation and survival", Blood, vol. 109, No. 11, pp. 5002-5010, 2007.
Banner et al., "Crystal Structure of the Soluble Human 55 kd TNF Receptor-Human TNFβ Complex: Implications for TNF Receptor Activation" Cell 73:431-445 (1993).
Bartkowiak, T.; Curran, M. A., "4-1BB Agonists: Multi-Potent Potentiators of Tumor Immunity", Front Oncol, vol. 5, p. 117, 2015.
Baudino et al., "Crucial Role of Aspartic Acid at Position 265 in the CH2 Domain for Murine IgG2a and IgG2b Fc-Associated Effector Functions," J. Immunol., vol. 181, pp. 6664-6669, 2008.
Bauer et al., "Targeted Bioactivity of Membrane-Anchored TNF by an Antibody-Derived TNF Fusion Protein" J Immunol 172(6):3930-3939 (2004).
Baumann et al., "Functional expression of CD134 by neutrophils" Eur. J. Immunol. 34:2268-2275 (2004).

Berinstein N. L.,"Carcinoembryonic Antigen as a Target for Therapeutic Anticancer Vaccines: A Review," J Clin Oncol., vol. 20, pp. 2197-2207, 2002.
Skerra, "Review Lipocalins as a scaffold," Biochim Biophys Acta, vol. 1482, pp. 337-350, 2000.
Bodmer et al., "The molecular architecture of the TNF superfamily" Trends Biochem Sci 27:19-26 (2002).
Boomer, "An Enigmatic Tail of CD28 Signaling," Cold Spring Harbor Perspectives in Biology, Aug. 1, 2010, vol. 2, Nr: 8, pp. a002436.
Booy et al., "Monoclonal and bispecific antibodies as novel therapeutics," Arch Immunol Ther Exp(Warsz). 54(2):85-101 (2006).
Bosch et al., "MCSP/CD3-bispecific single-chain antibody construct engages CD4+ and CD8+ T cells for lysis of MCSP-expressing human uveal melanoma cells," AACR 101st Annual Meeting. Apr. 17-21, Washington, DC. 70(8 Suppl) Abstract 5621 (2010).
Bowie, J. U. et al., "Deciphering the message in protein sequences: tolerance to amino acid substitutions," Science, vol. 247, pp. 1306-1310, 1990.
Brauner-Osbomea et al., "Cloning and characterization of a human orphan family C G-protein coupled receptor GPRC5D," Biochimica Et Biophysica Acta. Gene Structure and Expression, vol. 1518, Nr: 3, pp. 237-248, 2001.
Bremer et al., "Target Cell-Restricted and -Enhanced Apoptosis Induction By A scFv:sTRAIL Fusion Protein With Specificity for the Pancarcinoma-Associated Antigen EGP2" Int. J. Cancer 109:281-290(2004).
Bremer et al., "Targeting of the Tumor Necrosis Factor Receptor Superfamily for Cancer Immunotherapy" ISRN Oncology 2013:1-25 (2013).
Brennan et al., "Preparation of bispecific antibodies by chemical recombination of monoclonal immunoglobulin G1 fragments," Science, (19850000), vol. 229, p. 81.
Brodeur et al., "Mouse-Human Myeloma Partners for the Production of Heterhybridomas," Monoclonal Antibody Production Techniques and Applications New York:Marcel Dekker. 1 nc.:51-63 (1987).
Broil et al., "CD137 Expression in Tumor Vessel Walls High Correlation With Malignant Tumors" Am. J. Chin. Pathol 115:543-549, 2001.
Bruggemann et al., "Comparison of the effector functions of human immunoglobulins using a matched set of chimeric antibodies," J Exp Med, vol. 166, pp. 1351-1361, 1987.
Buechele et al., "4-1BB ligand modulates direct and Rituximab-induced NK-cell reactivity in chronic lymphocytic eukemia" J Immunol 42:737-748 (2012).
Buhmann et al., "Immunotherapy with FBTA05 (Bi20), a trifunctional bispecific anti-CD3 × anti-CD20 antibody and donor lymphocyte infusion (DLI) in relapsed or refractory B-cell lymphoma after allogeneic stem cell transplantation study protocol of an investigator-driven, open-label, non-randomized, uncontrolled, dose-escalating Phase I/II-trial," Journal of Translational Medicine, vol. 11, Nr: 1, p. 160, Jul. 2013.
Burton, "Immunoglobulin G: functional," Mol. Immunol., vol. 22, pp. 161-206, 1985.
Capel, P.J. et al., "Heterogeneity of Human IgG Fc Receptors," Immunomethods, vol. 4, pp. 25-34, 1994.
Carreno et al., "The B7 Family of Ligands and Its Receptors: New Pathways for Costimulation and Inhibition of Immune Responses," Annual Review of Immunology, Jan. 1, 2002, vol. 20, pp. 29-53.
Carter, "Bispecific human IgG by design" J Immunol Methods 248(1-2):7-15 (Feb. 1, 2001).
Carter, R.H et al., "Role of CD19 signal transduction in B cell biology," Immunol. Res., (2002), vol. 26, pp. 45-54.
Chan et al., "Variable region domain exchange in human IgGs promotes antibody complex formation with accompanying structural changes and altered effector functions," Mol Immunol. 41(5):527-38 (2004).
Chang et al., "Affinity Maturation of an Epidermal Growth Factor Receptor Targeting Human Monoclonal Antibody ER414 by CDR Mutation," Immune Network, Jan. 1, 2012, The Korean Society for Immunology, vol. 12, Nr: 4, pp. 155.

(56) References Cited

OTHER PUBLICATIONS

Chau I. et al., "The Value of Routine Serum Carcino-Embryonic Antigen Measurement and Computed Tomography in the Surveillance of Patients After Adjuvant Chemotherapy for Colorectal Cancer," J Clin Oncol., vol. 22, pp. 1420-1429, 2004.
Chelius et al., "Identification and Characterization of Deamidation Sites in the Conserved Regions of Human mmunoglobulin Gamma Antibodies," Anal. Chem., 77, 18, 6004-6011, Aug. 15, 2005.
Cui et al., "Chemically programmed bispecific antibodies that recruit and activate T cells," J Biol Chem. 287 (34):28206-14 (2012) (10 pages).
Chen et al., "Selection and Analysis of an Optimized Anti-VEGF Antibody: Crystal Structure of an Affinity-matured Fab in Complex with Antigen," J Mol Biol, (1999), vol. 293, pp. 865-881.
Chen et al., "Molecular mechanisms of T cell co-stimulation and co-inhibition," Nature Reviews Immunology, Apr. 1, 2013,vol. 13, Nr: 4, pp. 227-242.
Cho S.F. Anderson K.C. Tai Y.T., "Targeting B Cell Maturation Antigen (BCMA) in Multiple Myeloma: Potential Uses of BCMA-Based Immunotherapy", Front Immunol., vol. 9, p. 1821, 2018.
Choi et al., "4-1BB Functions as a Survival Factor in Dendritic Cells" J Immunol 182:4107-4115(2009).
Chothia et al., "Canonical structures for the hypervariable regions of immunoglobulins," J. Mol. Biol., vol. 196, pp. 901-917, 1987.
Clackson et al., "Making antibody fragments using phage display libraries" Nature 352(6336):624-628 (Aug. 15. 1991).
Clynes et al., "Fc receptors are required in passive and active immunity to melanoma," Proc Natl Acad Sci USA, vol. 95, pp. 652-656, 1998.
Cohen et al., "GPRC5D is a promising marker for monitoring the tumor load and to target multiple myeloma cells," Hematology, Nov. 1, 2013, vol. 18, Nr: 6, pp. 348-351.
Cole S.L. et al., "Involvement of the 4-1BB/4-1BBL Pathway in Control of Monocyte Numbers by Invariant NKT Cells," J. Immunol., vol. 192, No. 8, pp. 3898-3907, 2014.
Conry, R.M. et al., "Phase I trial of an anti-CD19 deglycosylated ricin A chain immunotoxin in non-Hodgkin'lymphoma: effect of an intensive schedule of administration," J. Immunother. Emphasis Tumor Immunol., (1995), vol. 18, pp. 231-241.
Cragg et al., "Complement-mediated lysis by anti-CD20 mAb correlates with segregation into lipid lafts," Blood, vol. 101, pp. 1045-1052, 2003.
Cragg et al., "Antibody specificity controls in vivo effector mechanisms of anti-CD20 reagents," Blood, vol. 103, pp. 2738-2743, 2004.
Croft et al., "The significance of OX40 and OX40L to T-cell biology and immune disease" Immunological Reviews 229:173-191,(2009).
Cuadros C. et al., "Vaccination with dendritic cells pulsed with apoptotic tumors in combination with anti-OX40 and anti-4-1BB monoclonal antibodies induces T cell-mediated protective immunity in Her-2/neu transgenic mice." Int J Cancer 116:934-943 (2005).
Cunningham et al., "High-Resolution Epitope Mapping of hGH-Receptor Interactions by Alanine-Scanning Mutagenesis," Science, vol. 244, pp. 1081-1085, 1989.
Curran M. A. et al., "Combination CTLA-4 blockade and 4-1BB activation enhances tumor rejection by increasing T-cell infiltration, proliferation, and cytokine production." PLoS One 6:e19499. (2011).
Dai et al., "Curing Mice with Large Tumors by Locally Delivering Combinations of Immunomodulatory Antibodies," Clinical Cancer Research, Mar. 1, 2015, vol. 21, Nr: 5, pp. 1127-1138.
Dall'Acqua et al., "Antibody humanization by framework shuffling" Methods 36(1):43-60, (Jan. 17, 2005).
Dall'Acqua, W.F. et al., "Properties of human IgG1s engineered for enhanced binding to the neonatal Fc receptor (FcRn)," J. Biol. Chem., vol. 281, pp. 23514-23524, 2006.
Daugherty et al., "Quantitative analysis of the effect of the mutation frequency on the affinity maturation of single chain Fv antibodies," Proceedings of the National Academy of Sciences (PNAS), vol. 97, Nr: 5, pp. 2029-2034, 2000.

De Haas, M. et al., "Fc gamma receptors of phagocytes," J Lab Clin Med. Oct. 1995;126(4):330-41.
Diehl et al., "In Vivo Triggering Through 4-1BB Enables Th-Independent Priming of CTL in the Presence of an Intact DD28 Costimulatory Pathway" J Immunol 168:3755-3762 (2002).
Dubrot et al., "Treatment with anti-CD137 mAbs causes intense accumulations of liver T cells without selective antitumor immunotherapeutic effects in this organ" Cancer Immunol Immunother 59:1223-1233 (2010).
Duncan, et al., "The binding site for C1q on IgG," Nature, vol. 322, pp. 738-740, 1988.
Edelman et al., "The covalent structure of an entire gammaG immunoglobulin molecule," Proc Natl Acad Sci USA, May 1969;63(1):78-85.
Engelhardt et al., "CTLA-4 overexpression inhibits T cell responses through a CD28-B7-dependent mechanism", J Immunol, vol. 177, pp. 1052-1061, 2006.
Esensten et al., "CD28 Costimulation: From Mechanism to Therapy," Immunity, May 17, 2016, vol. 44, Nr: 5, pp. 973-988.
Fingl et al. Basis of Therapeutics, "Ch. 1—General Principles" Fifth edition, New York:Macmillan Publishing Co., Inc., :1-46 (1975).
Flamini et al., "Free DNA and carcinoembryonic antigen serum levels: an important combination for diagnosis of colorectal cancer," Clin Cancer Res, vol. 12, No. 23, pp. 6985-6988, 2006.
Futagawa et al., "Expression and function of 4-1BB and 4-1BB ligand on murine dendritic cells" International Immonology 14:275-286 (2002).
Gao et al., "Comparative Transcriptome Analysis of Fetal Skin Reveals Key Genes Related to Hair Follicle Morphogenesis in Cashmere Goats", PLoS One, (20160000), vol. 11, No. 3, p. e0151118.
Gaugitsch et al., "A novel transiently expressed, integral membrane protein linked to cell activation. Molecular cloning via the rapid degradation signal AUUUA" J Biol Chem. 267(16):11267-11273 (Jun. 5, 1992).
Gazzano-Santoro et al., "A non-radioactive complement-dependent cytotoxicity assay for anti-CD20 monoclonal antibody," J Immunol Methods, vol. 202, p. 163, 1996.
Gebauerskerra, "Engineered protein scaffolds as next-generation antibody therapeutics", Curr Opin Chem Biol, vol. 13, pp. 245-255, 2009.
Gerngross, "Advances in the production of human therapeutic proteins in yeasts and filamentous fungi," Nat Biotech, vol. 22, pp. 1409-1414, 2004.
Gessner, J.E. et al., "The IgG Fc receptor family," Ann. Hematol., vol. 76, pp. 231-248, 1998.
Gold. P. et al.. "Specific carcinoembryonic antigens of the human digestive system" J Exp Med 122(3)1467-481 (Sep. 1, 1965).
Gold et al., "Demonstration of Tumor-Specific Antigens in Human Colonic Carcinomata By Mmunological Tolerance and Absorption Techniques," J Exp Med., vol. 121, pp. 439-462, 1965.
Goldenberg D M., "Cancer imaging with CEA antibodiesi historical and current perspectives," The International Journal of Biological Markers, vol. 7, pp. 183-188, 1992.
Goodwin et al., "Molecular Cloning of a Ligand for the Inducible T Cell Gene 4-1BB: A Member of an Emerging Family of Cytokines With Homology To Tumor Necrosis Factor," Eur J Immunol, Oct. 1993;23(10):2631-41.
Graff et al., "Directed evolution of an anti-carcinoembryonic antigen scFv with a 4-day monovalent dissociation halftime at 37 degrees C" Protein Eng. Des. Scl. 17(4)1293-304 (Jun. 2004).
Graham et al., "Characteristics of a human cell line transformed by DNA from human adenovirus type 5," J Gen Virol, vol. 36, p. 59-72, 1977.
Grevys, A. et al., "Fc Engineering of Human IgG1 for Altered Binding to the Neonatal Fc Receptor Affects Fc Effector Functions," J. Immunol., vol. 194, pp. 5497-5508, 2015.
Gruber et al., "Efficient tumor cell lysis mediated by a bispecific single chain antibody expressed in *Escherichia coli*," J. Immunol., vol. 152, p. 5368, 1994.

(56) References Cited

OTHER PUBLICATIONS

Gunasekaran K. et al., "Enhancing antibody Fc heterodimer formation through electrostatic steering effects applications to bispecific molecules and monovalent IgG," J Biol. Chem., vol. 285, No. 25, pp. 19637-19646, 2016.
Guo Z. et al., "Combined TIM-3 blockade and CD137 activation affords the long-term protection in a murine model of ovarian cancer." J Transl Med 11:215 (2013).
Guyer, R.L. et al., "Immunoglobulin Binding by Mouse Intestinal Epithelial Cell Receptors," J. Immunol., vol. 117, pp. 587-593, 1976.
Hammarstrom S., "The carcinoembryonic antigen (CEA) family: structures, suggested functions and expression in normal and malignant tissues," Semin Cancer Biol., vol. 9, No. 2, pp. 67-81, 1999.
Harlow and Lane Antibodies: A Laboratory Manual Cold Spring Harbor, N.Y.:Cold Spring Harbor Laboratory, vol. Chap. 14 (1988).
Heeley, "Mutations Flanking the Polyglutamine Repeat in the Modulatory Domain of Rat Glucocorticoid Receptor Lead to an Increase in Affinity for Hormone," Endocr Res, vol. 28, pp. 217-229, 2002.
Heinisch et al., "CD137 activation abrogates granulocytemacrophage colony-stimulating factor-mediated anti-apoptosis in neutrophils" Eur. J. Immunol. 30:3441-3346 (2000).
Heinisch I.V., "Functional CD137 receptors are expressed by eosinophils from patients with IgE-mediated allergic responses but not by eosinophils from patients with non-IgE-mediated eosinophilic disorders," J Allergy Clin Immunol., vol. 108, No. 1, pp. 21-28, 2001.
Hekman, A. et al., "Initial experience with treatment of human B cell lymphoma with anti-CD19 monoclonal antibody," Cancer Immunology, Immunotherapy vol. 32, pp. 364-372, (1991).
Hellstrom et al., "Strong antitumor activities of IgG3 antibodies to a human melanoma-associated ganglioside," Proc Natl Acad Sci USA, vol. 82, pp. 1499-1502, 1985.
Hellstrom et al., "Antitumor effects of L6, an IgG2a antibody that reacts with most human carcinomas," Proc Natl Acad Sci USA, vol. 83, pp. 7059-7063, 1986.
Hinner et al., "Abstract B016: Costimulatory T-cell engagement by PRS-343, a CD137 (4-1BB)/HER2 bispecific, leads to tumor growth inhibition and TIL expansion in humanized mouse model," Nov. 2016Cancer Immunology Research 4(11 Supplement):B016-B016.
Holger, "Affinity maturation by random mutagenesis and phage display," Antibody Engineering vol. 1, pp. 397-409, 2010.
Holliger et al., "Specific killing of lymphoma cells by cytotoxic T-cells mediated by a bispecific diabody," Protein Engineering, Design and Selection, vol. 9, Issue 3, Mar. 1996, pp. 299-305.
Hollinger et al., "Diabodies": small bivalent and bispecific antibody fragments, Proc Natl Acad Sci USA, vol. 90, pp. 6444-6448, 1993.
Honeychurch et al., "Bispecific Ab therapy of B-cell lymphoma: target cell specificity of antibody derivatives appears critical in determining therapeutic outcome," Cancer Immunol Immunother, 45(3-4):171-3 (1997).
Hoogenboom et al., "Overview of Antibody Phage-Display Technology and Its Applications" Methods Mol. Biol. 178, pp. 1-37, Feb. 2002.
Shields et al., "High Resolution Mapping of the Binding Site on Human IgG1 for FcgRI, FcgRII, FcgRIII, and FcRn and Design of IgG1 Variants with Improved Binding to the FcgR," J. Biol. Chem., vol. 276, pp. 6591-6604, Mar. 2, 2001.
Shindo, Y., et al., "Combination Immunotherapy with 4-1BB Activation and PD-1 Blockade Enhances Antitumor Efficacy in a Mouse Model of Subcutaneous Tumor" Anticancer Res 35(1):129-136 (Jan. 1, 2015).
Silacci et al., "Design, construction, and characterization of a large synthetic human antibody phage display library" Proteomics 5(9):2340-50 (2005).
Silverman et al., "Multivalent avimer proteins evolved by exon shuffling of a family of human receptor domains," Nature Biotechnology, vol. 23, No. 12, pp. 1556-1561, Nov. 20, 2005.
Simeone et al., "Immunomodulating antibodies in the treatment of metastatic melanoma: The experience with anti-CTLA-4, anti-CD137, and anti-PD1" Journal of Immunotoxicology 9:241-247, 2012.
Singer et al., Genes and Genomes, 1, 1998, pp. 63-64. (The English abstract included.).
Skerra, "Lipocalins as a scaffold," Biochim Biophys Acta, vol. 1482, pp. 337-350, 2000.
Snell et al., "T-cell intrinsic effects of GITR and 4-1BB during viral infection and cancer immunotherapy" Immunological Reviews 244:197-217, 2011.
Stadler et al., "Elimination of large tumors in mice by mRNA-encoded bispecific antibodies," Nature Medicine, vol. 23, pp. 815-817, Jun. 12, 2017.
Stagg et al., "Anti-ErbB-2 mAb therapy requires type I and II interferons and synergizes with anti-PD-1 or anti-CD137 mAb therapy" Proc. Nall. Acad. Sci. USA 108:7142-7147, Apr. 26, 2011.
Steidl et al., "In vitro affinity maturation of human GM-CSF antibodies by targeted CDR-diversification," Molecular Immunology, vol. 46, Nr: 1, pp. 135-144, Nov. 1, 2008.
Stubenrauch et al., "Impact of molecular processing in the hinge region of therapeutic IgG4 antibodies on disposition profiles in cynomolgus monkeys," Drug Metab Dispos. 38(1):84-91, 2010.
Stumpp et al., "DARPins: A new generation of protein therapeutics," Drug Discovery Today, Aug. 1, 2008 Elsevier, vol. 13, Nr: 15-16, pp. 695-701, Aug. 2008.
Sun et al., "Anti-CD20/CD3 T cell-dependent bispecific antibody for the treatment of B cell malignancies," Science Translational Medicine, vol. 7, Nr: 287, pp. 287ra70, May 13, 2015.
Suntharalingam et al., "Cytokine Storm in a Phase 1 Trial of the Anti-CD28 Monoclonal Antibody TGN1412," N Engl J Med, vol. 355, pp. 1018-1028, Aug. 14, 2006.
Tai et al., "Induction of autoimmune disease in CTLA-4-/- mice depends on a specific CD28 motif that is required for in vivo costimulation". Proc Natl Acad Sci USA, vol. 104, pp. 13756-13761, Jul. 11, 2007.
Tan et al., "Superhumanized" Antibodies: Reduction of Immunogenic Potential by Complementarity-Determining Region Grafting with Human Germline Sequences: Application to an Anti-CD28, J. Immunology, vol. 169, pp. 1119-1125, 2002.
Teng et al., "CD1d-Based Combination Therapy Eradicates Established Tumors in Mice" J Immunol 183:1911-1920 (2009).
Thompson, et al., "CD28 activation pathway regulates the production of multiple T-cell-derived lymphokines/cytokines". Proc Natl Acad Sci USA, vol. 86, pp. 1333-1337, Feb. 1989.
Tirosh et al., "Dissecting the multicellular ecosystem of metastatic melanoma by single-cell RNA-seq," Science, Apr. 8, 2016, vol. 352, Issue 6282, pp. 189-196.
Torisu-Itakura et al., "Redirected lysis of human melanoma cells by a MCSP/CD3-bispecific BiTE antibody that angages patient-derived T cells," J Immunother. 34(8):597-605, Oct. 2011.
Traunecker et al., "Bispecific single chain molecules (Janusins) target cytotoxic lymphocytes on HIV infected cells," EMBO J., vol. 10, p. 3655-3659, 1991.
Tutt et al., "Trispecific F(ab')3 derivatives that use cooperative signaling via the TCR/CD3 complex and CD2 to activate and redirect resting cytotoxic T cells," J Immunol 147(1):60-9, Jul. 1, 1991.
UniProt, Database accession No. F6W5G6, Jul. 27, 2011.
UniProt, Database accession No. P00533, Nov. 1, 1997.
UniProt, Database accession No. P06731, Jan. 11, 2011.
UniProt, Database accession No. P08637, Aug. 1, 1990.
UniProt, Database accession No. P11836, Oct. 1, 1989.
UniProt, Database accession No. P15391, Nov. 13, 2007.
UniProt, Database accession No. P20138, Oct. 17, 2006.
UniProt, Database accession No. P20334, Feb. 1, 1991.
UniProt, Database accession No. P97321, May 1, 1997.
UniProt, Database accession No. Q6UVK1, May 18, 2020.
UniProt, Database accession No. Q07011, Feb. 1, 1995.
UniProt, Database accession No. Q12884, Mar. 23, 2010.
UniProt, Database accession No. Q15116, Apr. 17, 2007.
UniProt, Database accession No. Q92838, Jul. 15, 1999.

(56) References Cited

OTHER PUBLICATIONS

Urlaub et al., "Isolation of Chinese hamster cell mutants deficient in dihydrofolate reductase activity," Proc Natl Acad Sci USA, vol. 77, p. 4216-4220, Jul. 1980.
Van De Winkel et al., "Biology of Human Immunoglobulin G Fc Receptors," Biol., vol. 49, pp. 511-524, 1991.
Van Dijkvan De Winkel, "Human antibodies as next generation therapeutics," Curr Opin Pharmacol, vol. 5, pp. 368-374, Aug. 2001.
Van Muijen, Goos N.P., et al., "Establishment and characterization of a human melanoma cell line (MV3) which is nighly metastatic in nude mice" Int J Cancer 48(1):85-91 (Apr. 22, 1991).
Verhoeyen et al., "Reshaping human antibodies: grafting an antilysozyme activity," Science, vol. 239, pp. 1534-1536, Mar. 25, 1988.
Vlasfeld, L.T. et al., "Treatment of low-grade non-Hodgkin's lymphoma with continuous infusion of low-dose recombinant interleukin-2 in combination with the B-cell-specific monoclonal antibody CLB-CD19," Cancer Immunol. Immunother., (1995), vol. 40, pp. 37-47.
Von Kempis et al., "Differentiation-dependent and stimulus-specific expression of ILA, the human 4-1BB-homologue, in cells of mesenchymal origin" Osteoarthritis and Cartilage 5:394-406 (1997).
Wagener, C. et al., "Monoclonal antibodies for carcinoembryonic antigen and related antigens as a model system: a systematic approach for the determination of epitope specificities of monoclonal antibodies" J Immunol 130(5):2308-2315 (May 1, 1983).
Wei, H. et al., "Combinatorial PD-1 bloackade and CD137 activation has therapeutic efficacy in murine cancer models and synergizes with cisplatin." PLoS One 8:e84927 (Dec. 19, 2013).
Weidle, U., et al., "The intriguing options of multispecific antibody formats for treatment of cancer" Cancer Genomics Proteomics 10(1):1 -18 (Jan. 31, 2013).
Wen T. et al., "4-1BB Ligand-Mediated Costimulation of Human T Cells Induces CD4 and CD8 T Cell Expansion, Cytokine Production, and the Development of Cytolytic Effector Function," J. Immunol., vol. 168, pp. 4897-4906, 2002.
WHO Drug Infromation, vol. 22, No. 2, p. 124, 2008.
WHO Drug Information, vol. 23, No. 2, p. 176, 2009.
Wikman et al., "Selection and characterization of HER2/neu-binding affibody ligands," Protein Eng. Des. Sel., vol. 17, pp. 455-462, Jun. 18, 2004.
Wilcox et al., "Cutting Edge: Expression of Functional CD137 Receptor by Dendritic Cells" J Immunol 168:4262-4267, (2002).
Wilcox et al., "Ligation of CD137 receptor prevents and reverses established anergy of CD8+ cytolytic T lymphocytes in vivo" Blood 103: 177-184 (2004).
Wolf et al., "BiTEs:bispecific antibody constructs with unique anti-tumor activity," Drug Discovery Today, 10(18):1237-44, Sep. 15, 2005.
Won et al., "The Structure of the Trimer of Human 4-1BB Ligand Is Unique among Members of the Tumor Necrosis Factor Superfamily," Mar. 19, 2010, The Journal of Biological Chemistry 285, 9202-9210.
Wright et al., "Effect of glycosylation on antibody function: implications for genetic engineering," TIBTECH, vol. 15, pp. 26-32, Jan. 1997.
Wyzgol et al., "Trimer Stabilization, Oligomerization, and Antibody-Mediated Cell Surface Immobilization Improve the Activity of Soluble Trimers of CD27L, CD40L, 41BBL, and Glucocorticoid-Induced TNF Receptor Ligand1" The Journal of Immunology 183:1851-1861 (2009).
Xu et al., "Abstract 957: Design of CD19-4-1BBL, a novel CD19-targeted 4-1BB ligand for combination therapy with CD20 T-cell bispecific antibodies and CD20 antibodies," Cancer Res Jul. 1, 2018 (78) (13 Supplement) 957.
Yang et al., "CDR Walking Mutagenesis for the Affinity Maturation of a Potent Human ANTI-HIV-1 Antibody Into the Picomolar Range," Journal of Molecular Biology, vol. 254, pp. 392-403, 1995.
Yazaki et al., "Expression of recombinant antibodies in mammalian cell lines" Methods Molec Biol 248:255-268 2004).

Yokosuka et al., "Programmed cell death 1 forms negative costimulatory microclusters that directly inhibit T cell receptor signaling by recruiting phosphatase SHP2," J Exp Med (2012) 209 (6): 1201-1217, May 28, 2012.
Zahnd et al., "A Designed Ankyrin Repeat Protein Evolved to Picomolar Affinity to Her2," J. Mol. Biol., 2007, vol. 369, pp. 1015-1028.
Zhang et al., "Anti-Tumor Effect Mediated by Peripheral Blood-Derived Human Dendritic Cells in vitro," Cell Mol Immunol., 2004, vol. 1, No. 1, pp. 71-76.
Zhang et al., "CD137 Promotes Proliferation and Survival of Human B Cells" J Immunol 184:787-795 (2010).
Zhang et al., "Targeted and Untargeted CD137L Fusion Proteins for the Immunotherapy of Experimental Solid Tumors," Clinical Cancer Research, Association for Cancer Research, vol. 13, Nr: 9, pp. 2758-2767, May 2007.
Zheng et al., "Landscape of Infiltrating T Cells in Liver Cancer Revealed by Single-Cell Sequencing", Cell, 2017, vol. 169, pp. 1342-1356 e1316.
Zhou et al., Mammalian Cell Cultures for Biologies Manufacturing, 2014.
Zhu et al., "Identification of heavy chain residues in a humanized anti-CD3 antibody important for efficient antigen binding and T cell activation," J Immunol. 155(4): 1903-10 (1995).
Filpula et al., "Antibody engineering and modification technologies," Biomolecular Engineering, vol. 24, Issue 2, Jun. 2007, pp. 201-215.
Hoffman et al., "Blinatumomab, a bi-specific anti-CD19/CD3 BiTE® antibody for the treatment of acute lymphoblastic eukemia: perspectives and current pediatric applications," Front. Oncol., vol. 4 | Article 63, pp. 1-5, Mar. 31, 2014.
International Search Report and Written Opinion, dated May 16, 2018, in PCT Appl. No. PCT/EP2018/050024.
International Search Report and Written Opinion, dated Mar. 14, 2018, in PCT Appl. No. PCT/EP2017/083222.
The English transaltion of the Japanese Office Action, dated Mar. 23, 2021, in the related Japanese Patent Appl. Mo. 2019-219527.
Jiang et al., "Research on the preparation and biological activity of genetically engineered antibody anti-CD19 (Fab)-LDM," Chinese Pharmacological Bulletin, vol. 29, No. 10, pp. 1363-1368, Nov. 7, 2013. (The English abstract included).
Li et al., "Preparation of a Humanized Anti2CD3 Antibody Containing Mutated Constant Region and Its Biological Activity," Chinese Journal of Biochemistry and Molecular Biology, vol. 20(1), pp. 28-33, Feb. 2004.
Morris et al., "Development and Characterization of Recombinant Human Fc:OX40L fusion protein linked via a coiled-coil trimerization domain," Mol Immunol. May 2007; 44(12): 3112-3121.
Notice of Reasons for Rejection for Japanese Patent Application No. 2018-516827, dated Sep. 15, 2020.
The Chinese Office Action, dated Jan. 6, 2021, in the related Chinese Patent Appl. No. 201680056947.1.
US NIH et al., "ClinicalTrials Identifier—NCT00309023—Urelumab" Study of BMS-663513 in Patients With Advanced Cancer: 1-6 (Oct. 12, 2015).
US NIH, "Clinical Trials Identifier—NCT00612664—Urelumab" Phase II, 2nd Line Melanoma—RAND Monotherapy: 1-6 (Oct. 12, 2015).
Vinay, D. et al., "4-1BB signaling beyond T cells" Cell Mol Immunol 8(4):281-284 (Jul. 1, 2011).
World Health Organization et al., "International Nonproprietary Names for Pharmaceutical Substances (INN)—obinutuzumab" WHO Drug Information 25(1):75-76 (Mar. 1, 2011).
World Health Organization et al., "Proposed International Nonproprietary Names—obinutuzumabum" WHO Drug Information 26(4):453 (Jan. 10, 2013).
Yazawa et al., "Immunotherapy using unconjugated CD 19 monoclonal antibodies in animal models for B lymphocyte malignancies and autoimmune disease," PNAS, vol. 102, No. 42, pp. 15178-15183, Oct. 18, 2005.
Ali et al., "Transferrin Trojan Horses as a Rational Approach for the Biological Delivery of Therapeutic Peptide Domains," J. Biol. Chem, vol. 274, pp. 24066-24073, Aug. 20, 1999.

(56) References Cited

OTHER PUBLICATIONS

Binz et al., "Designing Repeat Proteins: Well-expressed, Soluble and Stable Proteins from Combinatorial Libraries of Consensus Ankyrin Repeat Proteins," J. Biol. Chem, vol. 274, pp. 24066-24073, Jul. 10, 2003.
Acuto, O.Michel, F., "CD28-mediated co-stimulation: a quantitative support for TCR signalling", Nat Rev Immunol, vol. 3, pp. 939-951, Dec. 2003.
Atamaniuk et al., "Overexpression of G protein-coupled receptor 5D in the bone marrow is associated with poor prognosis in patients with multiple myeloma," European Journal of Clinical Investigation, vol. 42, Nr: 9, pp. 353-960, Sep. 1, 2012.
Banfield et al., "V L :V H Domain Rotations in Engineered Antibodies: Crystal Structures of the Fab Fragments FromTwo Murine Antitumor Antibodies and Their Engineered Human Constructs," Proteins, vol. 29, No. 2, pp. 161-171, Apr. 1997.
Brauner-Osbornea et al., "Cloning and characterization of a human orphan family C G-protein coupled receptor GPRC5D," Biochimica et Biophysica Acta. Gene Structure and Expression, vol. 1518, Nr: 3, pp. 237-248, Apr. 16, 2001.
Bremer et al., "Targeting of the Tumor Necrosis Factor Receptor Superfamily for Cancer Immunotherapy" ISRN Oncology 2013:1-25, May 2013.
DATABASE Geneseq_Accession No. BBD25791, Anti-CD137/4-1BB Ab heavy chain variable region, SEQ 11. (2014).
DATABASE Geneseq_Accession No. BBD25792, Anti-CD137/4-1BB Ab light chain variable region, SEQ 12. (2014).
DATABASE Geneseq Accession No. AZT47926, Anti-FAP antibody (4B9) light chain variable region, SEQ ID 265. (2012).
DATABASE Geneseq Accession No. AZT47928, Anti-FAP antibody (4B9) heavy chain variable region, SEQ ID 267. (2012).
Fraser, J.D.Irving, B.A.Crabtree, G.R.Weiss, A., "Regulation of interleukin-2 gene enhancer activity by the T cell accessory molecule CD28", Science, vol. 251, pp. 313-316, Jan. 18, 1991.
Gennaro. Remington's Pharmaceutical Sciences 18th Edition:1321, 1326, 1634-1637 (1990).
Jennifer Lippincott-Schwartz, "Current Protocols in Cell Biology," Chapter 16, Antibodies as Cell Biological Tools (2002) 16.0.1-16.0.2.
Lombardi et al., "Molecular characterization of human multiple myeloma cell lines by integrative genomics: insights into the biology of the diseas", Genes Chromosomes Cancer, vol. 46, No. 3, pp. 226-238, Dec. 14, 2006.
Lonberg, "Human antibodies from transgenic animals," Nat Biotech, vol. 23, pp. 1117-1125, Sep. 7, 2005.
Maniatis et al., "Preface, Contents, and List of References" Molecular Cloning: A Laboratory Manual, 1st edition, Cold Spring Harbor:Cold Spring Harbor Laboratory Press pp. iii-x; 507-520 (1983).
Brodeur et al., "Monoclonal Antibody Production Techniques and Applications," New York:Marcel Dekker. Inc.:51-63 (1987).
Morris, Methods in Molec Biol "Epitope Mapping Protocols" Totowa, NJ. Humana Press, vol. 66 (1996).
Nucleotide, Database accession No. NP_004451.2, URL: NCBI, 2020.
Nucleotide, Database accession No. NP_032012.1, URL: NCBI, 2020.
Remington's Pharmaceutical Sciences, Mack Printing Company, (1990), pp. 1289-1329.
Rodrigues, M., et al., "Engineering a Humanized Bispecific F(ab')2 Fragment for Improved Binding TOT Cells" Int J Cancer Suppl 7):45-50 (1992).
Romer et al., "Preculture of PBMCs at high cell density increases sensitivity of T-cell responses, revealing cytokine release by CD28 superagonist TGN1412," Blood, vol. 118, No. 26, Dec. 22, 2011.
Ross et al., "Isolation and chemical characterization of a melanoma-associated proteoglycan antigen," Arch. Biochem. Biophys., vol. 225, pp. 370-38, Aug. 1983.
Roux et al., "Comparisons of the Ability of Human IgG3 Hinge Mutants, IgM, IgE, and IgA2, to Form Small Immune Complexes: A Role for Flexibility and Geometry," J Immunol., vol. 161, pp. 4083-4090, Jun. 11, 1998.
Sakuishi et al., "Targeting Tim-3 and PD-1 pathways to reverse T cell exhaustion and restore antitumor immunity," J Exp Med. 207(10):2187-94, Sep. 6, 2010.
Sambrook et al., Molecular cloning: A laboratory manual, Cold Spring Harbor Laboratory Press, (1989).
Schaefer et al., "Immunoglobulin domain crossover as a generic approach for the production of bispecific IgG antibodies," Proc Natl Acad Sci USA. 108(27):11187-92, Jul. 5, 2011.
Schwarz et al., "ILA, the Human 4-1BB Homologue, Is Inducible in Lymphoid and Other Cell Lineages" Blood 85:1043-1052, Feb. 12, 1995.
Segal et al., "Results From an Integrated Safety Analysis of Urelumab, an Agonist Anti-CD137 Monoclonal Antibody", Clin. Cancer Res., Oct. 18, 2016.
Seimetz et al., "Development and approval of the trifunctional antibody catumaxomab (anti-EpCAM × anti-CD3) as a targeted cancer immunotherapy," Cancer Treat Rev. 36(6):458-67, 2010.
Shao, Z. et al., "CD137 ligand, a member of the tumor necrosis factor family, regulates immune responses via reverse signal transduction." J Leukoc Biol 89:21-29, Jan. 2011.
Shi, W. et al., "Augmented antitumor effects of radiation therapy by 4-1BB antibody (BMS-69492) treatment." Anticancer Res 26:3445-3453 (2006).
The English translation of the Chinese Office Action, dated Sep. 3, 2021, in the related Chinese Patent Appl. No. 201880011647.0.
Li et al., "Structure design of bispecific antibodies and progress in the assembly process," Chinese Journal of New Drugs 2014, 23(20), pp. 2430-2436 (The English abstract included.).
Claus et al., "Tumor-targeted 4-1BB agonists for combination with T cell bispecific antibodies as off-the-shelf therapy," Sci. Transl. Med. 11, eaav5989, Jun. 12, 2019.
Hutchings et al., "Phase 1 Study of CD19 Targeted 4-1BBL Costimulatory Agonist to Enhance T Cell (Glofitamab Combination) or NK Cell Effector Function (Obinutuzumab Combination) in Relapsed/Refractory B Cell Lymphoma," (2020) Blood. 136(Suppl. 1). p. 16-17, Nov. 5, 2020.
Hinner et al., "Costimulatory T cell engagement via a novel bispecific anti-CD137/anti-HER2 protein," J Immunother Cancer. 2015; 3(Suppl 2): P187.
Jiang et al., "Study on the construction and expression of the human 4-1BBL extracellular domain/anti-CD20 Fab' fusion protein," Chinese Journal of Biotechnology, vol. 24, No. 3, pp. 376-380. (The English abstract).
Zheng, "Cellular and Molecular Biology of Cancer," Shanghai Science and Technology Press, p. 316, 1st edition in Feb. of 2011, published on Feb. 28, 2011. (The Concise Explanation of the Relevance of the Reference included.).

* cited by examiner

HUMANIZED ANTI-HUMAN CD19 ANTIBODIES AND METHODS OF USE

CROSS-REFERENCE TO RELATED APPLICATIONS

This application is a National Stage Application of PCT/EP2016/073412 filed Sep. 30, 2016, which claims priority from European Patent Application No. 15187820.4, filed on Oct. 1, 2015. The priority of said PCT and European Patent Application are claimed. Each of prior mentioned applications is hereby incorporated by reference herein in its entirety.

FIELD OF THE INVENTION

The present invention relates to humanized antibodies against human CD19 (anti-human CD19 antibody), methods for their production, pharmaceutical compositions containing these antibodies, and uses thereof.

BACKGROUND

Human CD19 is a 95 kDa transmembrane protein (B-cell co-receptor) exclusively expressed on B-cells and on follicular dendritic cells. CD 19 is found in association with CD21 and CD81. CD19 and CD21 are required for normal B-cell differentiation (Carter, R. H., et al., Immunol. Res. 26 (2002) 45-54). Antibodies against CD19 have been used in several clinical trials (see e. g. Hekman, A., et al., Cancer Immunol. Immunother. 32 (191) 364-372; Vlasfeld, L. T., et al., Cancer Immunol. Immunother. 40 (1995) 37-47; Conry, R. M., et al., J. Immunother. Emphasis Tumor Immunol. 18 (1995) 231-241; Manzke, O., et al., Int. J. Cancer 91 (2001) 516-522).

Antibodies against CD19 are e.g. mentioned in WO 2004/106381, WO 2005/012493, WO 2006/089133, WO 2007/002223, WO 2006/133450, WO 2006/121852, WO 2003/048209, U.S. Pat. No. 7,109,304, US 2006/0233791, US 2006/0280738, US 2006/0263357, US 2006/0257398, EP 1648512, EP 1629012, US 2008/0138336, WO 2008/022152 and in Bruenke, J., et al., Br. J. Hematol. 130 (2005) 218-228; Vallera, D. A., et al., Cancer Biother. Radiopharm. 19 (2004) 11-23; Ghetie, M. A., et al., Blood 104 (2004) 178-183; Lang, P., et al., Blood 103 (2004) 3982-3985; Loeffler, A., et al., Blood 95 (2000) 2098-2103; Le Gall, F., et al., FEBS Lett. 453 (1999) 164-168; Li, Q., et al., Cancer Immunol. Immunother. 47 (1998) 121-130; Eberl, G., et al., Clin. Exp. Immunol. 114 (1998) 173-178; Pietersz, G. A., et al., Cancer Immunol. Immunother. 41 (1995) 53-60; Myers, D. E., et al., Leuk. Lymphoma. 18 (1995) 93-102; Bejcek, B. E., et al., Cancer Res. 55 (1995) 2346-2351; Hagen, I. A., et al, Blood 85 (1995) 3208-3212; Vlasfeld, L. T., et al., Cancer Immunol. Immunother. 40 (1995) 37-47; Rhodes, E. G. et al., Bone Marrow Transplant. 10 (1992) 485-489; Zola, H., et al., Immunol. Cell Biol. 69 (1991) 411-422; Watanabe, M., et al., Cancer Res. 50 (1990) 3245-3248; Uckun, F. M., et al., Blood 71 (1988) 13-29; Pezzutto, A., et al.; J Immunol. 138 (1987) 2793-2799. Monoclonal antibody SJ25-C1 is commercially available (Product No. 4737, Sigma-Aldrich Co. USA, SEQ ID NO: 21 to 24). Antibodies with increased affinity to the FcγRIIIA are mentioned in WO 2008/022152.

Antibody against CD19 can have inhibitory or stimulating effects on B-cell activation. Binding of CD19 antibodies to mitogen-stimulated B-cells inhibits the subsequent rise in $Ca^{2+}$ and the resulting activation and proliferation of these cells and B-cell proliferation and differentiation can either be inhibited or enhanced by CD19 antibody depending on the mitogenic stimulus used and the degree of crosslinking by the antibody.

In WO 2004/106381 pharmaceutical compositions comprising bispecific anti-CD3, anti-CD19 antibody constructs for the treatment of B-cell related disorders are reported. Anti-CD19 antibodies are reported in WO 2005/012493. In WO 2006/089133 anti-CD19 antibodies and uses in oncology are reported. Anti-CD19 antibodies and their uses are reported in WO 2007/002223. In WO 2006/133450 anti-CD19 antibody therapy for the transplantation is reported.

In WO 2011/147834 antibodies against CD19 and uses thereof are reported.

SUMMARY

Herein are provided antibodies against (human) CD19 which are useful as a therapeutic agent for treatment of an autoimmune disease, rheumatoid arthritis, lupus, psoriasis, or a bone disease or for tumor treatment.

The invention is based, in part, on the finding that for removing multiple deamidation hotspots in a humanized anti-human CD19 antibody a single mutation is sufficient.

The antibodies as reported herein have properties causing a benefit for a patient suffering from a disease associated with pathologic increase of B-cells.

One aspect as reported herein is an antibody that specifically binds to human CD19, wherein the antibody comprises
(a) HVR-H1 comprising the amino acid sequence of SEQ ID NO: 03,
(b) HVR-H2 comprising the amino acid sequence of SEQ ID NO: 11,
(c) HVR-H3 comprising the amino acid sequence of SEQ ID NO: 05,
(d) HVR-L1 comprising the amino acid sequence of SEQ ID NO: 20 or 28,
(e) HVR-L2 comprising the amino acid sequence of SEQ ID NO: 07, and
(f) HVR-L3 comprising the amino acid sequence of SEQ ID NO: 08.

In one embodiment the antibody is a monoclonal antibody.

In one embodiment the antibody is a human, humanized or chimeric antibody.

In one embodiment the antibody is an antibody fragment that specifically binds to human CD19.

In one embodiment the antibody comprises
(a) a VH sequence having at least 95% sequence identity to the amino acid sequence of SEQ ID NO: 09 and a VL sequence having at least 95% sequence identity to the amino acid sequence of SEQ ID NO: 19, or
(b) a VH sequence having at least 95% sequence identity to the amino acid sequence of SEQ ID NO: 09 and a VL sequence having at least 95% sequence identity to the amino acid sequence of SEQ ID NO: 27, or
(c) a VH sequence and a VL sequence as in (a) or (b).

In one embodiment the antibody is a bispecific antibody that specifically binds to human CD19 and a second different antigen.

One aspect as reported herein is a pharmaceutical formulation comprising the antibody as reported herein and a pharmaceutically acceptable carrier.

One aspect as reported herein is the antibody as reported herein for the treatment of B-cell malignancies. In one embodiment the B-cell malignancy is selected from the group consisting of CLL, NHL and DLBCL.

One aspect as reported herein is the antibody as reported herein for use as a medicament.

In one embodiment the medicament is for the treatment of a B-cell cancer, an inflammatory disease, an autoimmune disease, rheumatoid arthritis, lupus, psoriasis, or a bone disease. In one embodiment the medicament is for the depletion of B-cells.

One aspect as reported herein is the antibody as reported herein for use in treating a B-cell cancer, an inflammatory disease, an autoimmune disease, rheumatoid arthritis, lupus, psoriasis, or a bone disease.

One aspect as reported herein is the antibody as reported herein for use in depleting B-cells.

One aspect as reported herein is the use of the antibody as reported herein in the manufacture of a medicament. In one embodiment the medicament is for the treatment of a B-cell cancer, an inflammatory disease, an autoimmune disease, rheumatoid arthritis, lupus, psoriasis, or a bone disease. In one embodiment the medicament is for the depletion of B-cells.

One aspect as reported herein is a method of treating an individual having a B-cell cancer comprising administering to the individual an effective amount of the antibody as reported herein.

One aspect as reported herein is a method of depleting B-cells in an individual comprising administering to the individual an effective amount of the antibody as reported herein.

One aspect as reported herein is a method for the manufacture of a medicament for the treatment of a disease comprising an antibody as reported herein. In one embodiment the disease is a B-cell cancer, an inflammatory disease, an autoimmune disease, rheumatoid arthritis, lupus, psoriasis, or a bone disease.

One aspect as reported herein is an isolated nucleic acid encoding the antibody as reported herein.

One aspect as reported herein is a host cell comprising the nucleic acid as reported herein.

One aspect as reported herein is a method of producing an antibody comprising culturing the host cell comprising the nucleic acid encoding the antibody so that the antibody is produced, recovering the antibody from the cell or the cultivation medium and purifying the antibody.

One aspect as reported herein is an immunoconjugate comprising the antibody as reported herein and a cytotoxic agent.

DETAILED DESCRIPTION OF EMBODIMENTS OF THE INVENTION

I. Definitions

An "acceptor human framework" for the purposes herein is a framework comprising the amino acid sequence of a light chain variable domain (VL) framework or a heavy chain variable domain (VH) framework derived from a human immunoglobulin framework or a human consensus framework, as defined below. An acceptor human framework "derived from" a human immunoglobulin framework or a human consensus framework may comprise the same amino acid sequence thereof, or it may contain amino acid sequence changes. In some embodiments, the number of amino acid changes are 10 or less, 9 or less, 8 or less, 7 or less, 6 or less, 5 or less, 4 or less, 3 or less, or 2 or less. In some embodiments, the VL acceptor human framework is identical in sequence to the VL human immunoglobulin framework sequence or human consensus framework sequence.

"Affinity" refers to the strength of the sum total of non-covalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant ($k_d$). Affinity can be measured by common methods known in the art, including those described herein.

An "affinity matured" antibody refers to an antibody with one or more alterations in one or more hypervariable regions (HVRs), compared to a parent antibody which does not possess such alterations, such alterations resulting in an improvement in the affinity of the antibody for antigen.

The terms "anti-human CD19 antibody" and "an antibody that specifically binds to human CD19" refer to an antibody that is capable of binding human CD19 with sufficient affinity such that the antibody is useful as a diagnostic and/or therapeutic agent in targeting human CD19. In one embodiment, the extent of binding of an anti-human CD19 antibody to an unrelated, non-CD19 protein is less than about 10% of the binding of the antibody to human CD19 as measured, by Surface Plasmon Resonance. In certain embodiments, an antibody that specifically binds to human CD19 has a dissociation constant ($K_D$) of $10^{-8}$ M or less.

The term "antibody" herein is used in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity.

The term "antibody-dependent cellular cytotoxicity (ADCC)" is a function mediated by Fc receptor binding and refers to lysis of target cells by an antibody as reported herein in the presence of effector cells. ADCC is measured in one embodiment by the treatment of a preparation of CD19 expressing erythroid cells (e.g. K562 cells expressing recombinant human CD19) with an antibody as reported herein in the presence of effector cells such as freshly isolated PBMC (peripheral blood mononuclear cells) or purified effector cells from buffy coats, like monocytes or NK (natural killer) cells. Target cells are labeled with $^{51}$Cr and subsequently incubated with the antibody. The labeled cells are incubated with effector cells and the supernatant is analyzed for released $^{51}$Cr. Controls include the incubation of the target endothelial cells with effector cells but without the antibody. The capacity of the antibody to induce the initial steps mediating ADCC is investigated by measuring their binding to Fcγ receptors expressing cells, such as cells, recombinantly expressing FcγRI and/or FcγRIIA or NK cells (expressing essentially FcγRIIIA). In one preferred embodiment binding to FcγR on NK cells is measured.

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')$_2$; diabodies; linear antibodies; single-chain antibody molecules (e.g. scFv); and multispecific antibodies formed from antibody fragments.

The term "chimeric" antibody refers to an antibody in which a portion of the heavy and/or light chain is derived from a particular source or species, while the remainder of the heavy and/or light chain is derived from a different source or species.

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., $IgG_1$, $IgG_2$, $IgG_3$, $IgG_4$, $IgA_1$, and $IgA_2$. The heavy chain constant domains that correspond to the different classes of immunoglobulins are called α, δ, ε, γ, and μ, respectively.

The term "cytotoxic agent" as used herein refers to a substance that inhibits or prevents a cellular function and/or causes cell death or destruction. Cytotoxic agents include, but are not limited to, radioactive isotopes (e.g., $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu); chemotherapeutic agents or drugs (e.g., methotrexate, adriamicin, vinca alkaloids (vincristine, vinblastine, etoposide), doxorubicin, melphalan, mitomycin C, chlorambucil, daunorubicin or other intercalating agents); growth inhibitory agents; enzymes and fragments thereof such as nucleolytic enzymes; antibiotics; toxins such as small molecule toxins or enzymatically active toxins of bacterial, fungal, plant or animal origin, including fragments and/or variants thereof; and the various antitumor or anti-cancer agents disclosed below.

The term "complement-dependent cytotoxicity (CDC)" refers to lysis of cells induced by the antibody as reported herein in the presence of complement. CDC is measured in one embodiment by the treatment of CD19 expressing human endothelial cells with an antibody as reported herein in the presence of complement. The cells are in one embodiment labeled with calcein. CDC is found if the antibody induces lysis of 20% or more of the target cells at a concentration of 30 μg/ml. Binding to the complement factor C1q can be measured in an ELISA. In such an assay in principle an ELISA plate is coated with concentration ranges of the antibody, to which purified human C1q or human serum is added. C1q binding is detected by an antibody directed against C1q followed by a peroxidase-labeled conjugate. Detection of binding (maximal binding $B_{max}$) is measured as optical density at 405 nm (OD405) for peroxidase substrate ABTS® (2,2'-azino-di-[3-ethylbenzthiazoline-6-sulfonate (6)]).

"Effector functions" refer to those biological activities attributable to the Fc region of an antibody, which vary with the antibody class. Examples of antibody effector functions include: C1q binding and complement dependent cytotoxicity (CDC); Fc receptor binding; antibody-dependent cell-mediated cytotoxicity (ADCC); phagocytosis; down regulation of cell surface receptors (e.g. B cell receptor); and B cell activation.

Fc receptor binding dependent effector functions can be mediated by the interaction of the Fc-region of an antibody with Fc receptors (FcRs), which are specialized cell surface receptors on hematopoietic cells. Fc receptors belong to the immunoglobulin superfamily, and have been shown to mediate both the removal of antibody-coated pathogens by phagocytosis of immune complexes, and the lysis of erythrocytes and various other cellular targets (e.g. tumor cells) coated with the corresponding antibody, via antibody dependent cell mediated cytotoxicity (ADCC) (see e.g. Van de Winkel, J. G. and Anderson, C. L., J. Leukoc. Biol. 49 (1991) 511-524). FcRs are defined by their specificity for immunoglobulin isotypes: Fc receptors for IgG antibodies are referred to as FcγR. Fc receptor binding is described e.g. in Ravetch, J. V. and Kinet, J. P., Annu. Rev. Immunol. 9 (1991) 457-492; Capel, P. J., et al., Immunomethods 4 (1994) 25-34; de Haas, M., et al., J. Lab. Clin. Med. 126 (1995) 330-341; and Gessner, J. E., et al., Ann. Hematol. 76 (1998) 231-248.

Cross-linking of receptors for the Fc-region of IgG antibodies (FcγR) triggers a wide variety of effector functions including phagocytosis, antibody-dependent cellular cytotoxicity, and release of inflammatory mediators, as well as immune complex clearance and regulation of antibody production. In humans, three classes of FcγR have been characterized, which are:

FcγRI (CD64) binds monomeric IgG with high affinity and is expressed on macrophages, monocytes, neutrophils and eosinophils. Modification in the Fc-region IgG at least at one of the amino acid residues E233-G236, P238, D265, N297, A327 and P329 (numbering according to EU index of Kabat) reduce binding to FcγRI. IgG2 residues at positions 233-236, substituted into IgG1 and IgG4, reduced binding to FcγRI by $10^3$-fold and eliminated the human monocyte response to antibody-sensitized red blood cells (Armour, K. L., et al., Eur. J. Immunol. 29 (1999) 2613-2624).

FcγRII (CD32) binds complexed IgG with medium to low affinity and is widely expressed. This receptor can be divided into two sub-types, FcγRIIA and FcγRIIB. FcγRIIA is found on many cells involved in killing (e.g. macrophages, monocytes, neutrophils) and seems able to activate the killing process. FcγRIIB seems to play a role in inhibitory processes and is found on B-cells, macrophages and on mast cells and eosinophils. On B-cells it seems to function to suppress further immunoglobulin production and isotype switching to, for example, the IgE class. On macrophages, FcγRIIB acts to inhibit phagocytosis as mediated through FcγRIIA. On eosinophils and mast cells the B-form may help to suppress activation of these cells through IgE binding to its separate receptor. Reduced binding for FcγRIIA is found e.g. for antibodies comprising an IgG Fc-region with mutations at least at one of the amino acid residues E233-G236, P238, D265, N297, A327, P329, D270, Q295, A327, R292, and K414 (numbering according to EU index of Kabat).

FcγRIII (CD16) binds IgG with medium to low affinity and exists as two types. FcγRIIIA is found on NK cells, macrophages, eosinophils and some monocytes and T cells and mediates ADCC. FcγRIIIB is highly expressed on neutrophils. Reduced binding to FcγRIIIA is found e.g. for antibodies comprising an IgG Fc-region with mutation at least at one of the amino acid residues E233-G236, P238, D265, N297, A327, P329, D270, Q295, A327, S239, E269, E293, Y296, V303, A327, K338 and D376 (numbering according to EU index of Kabat).

Mapping of the binding sites on human IgG1 for Fc receptors, the above mentioned mutation sites and methods for measuring binding to FcγRI and FcγRIIA are described in Shields, R. L., et al. J. Biol. Chem. 276 (2001) 6591-6604.

An "effective amount" of an agent, e.g., a pharmaceutical formulation, refers to an amount effective, at dosages and for periods of time necessary, to achieve the desired therapeutic or prophylactic result.

The term "Fc receptor" as used herein refers to activation receptors characterized by the presence of a cytoplasmatic ITAM sequence associated with the receptor (see e.g. Ravetch, J. V. and Bolland, S., Annu. Rev. Immunol. 19 (2001) 275-290). Such receptors are FcγRI, FcγRIIA and FcγRIIIA. The term "no binding of FcγR" denotes that at an antibody concentration of 10 μg/ml the binding of an antibody as reported herein to NK cells is 10% or less of the binding found for anti-OX40L antibody LC.001 as reported in WO 2006/029879.

While IgG4 shows reduced FcR binding, antibodies of other IgG subclasses show strong binding. However Pro238, Asp265, Asp270, Asn297 (loss of Fc carbohydrate), Pro329 and 234, 235, 236 and 237 Ile253, Ser254, Lys288, Thr307, Gln311, Asn434, and His435 are residues which provide if altered also reduce FcR binding (Shields, R. L., et al. J. Biol. Chem. 276 (2001) 6591-6604; Lund, J., et al., FASEB J. 9 (1995) 115-119; Morgan, A., et al., Immunology 86 (1995) 319-324; and EP 0 307 434). In one embodiment the antibody as reported herein is of IgG1 or IgG2 subclass and comprises the mutation PVA236, GLPSS331, and/or L234A/L235A. In one embodiment the antibody as reported herein is of IgG4 subclass and comprises the mutation L235E. In one embodiment the antibody further comprises the mutation S228P.

The term "Fc region" herein is used to define a C-terminal region of an immunoglobulin heavy chain that contains at least a portion of the constant region. The term includes native sequence Fc regions and variant Fc regions. In one embodiment, a human IgG heavy chain Fc region extends from Cys226, or from Pro230, to the carboxyl-terminus of the heavy chain. However, the C-terminal lysine (Lys447) of the Fc region may or may not be present. Unless otherwise specified herein, numbering of amino acid residues in the Fc region or constant region is according to the EU numbering system, also called the EU index, as described in Kabat, E. A. et al., Sequences of Proteins of Immunological Interest, 5th ed., Public Health Service, National Institutes of Health, Bethesda, Md. (1991), NIH Publication 91-3242.

The antibodies as reported herein comprise as Fc-region, in one embodiment an Fc-region derived from human origin. In one embodiment the Fc-region comprises all parts of the human constant region. The Fc-region of an antibody is directly involved in complement activation, C1q binding, C3 activation and Fc receptor binding. While the influence of an antibody on the complement system is dependent on certain conditions, binding to C1q is caused by defined binding sites in the Fc-region. Such binding sites are known in the state of the art and described e.g. by Lukas, T. J., et al., J. Immunol. 127 (1981) 2555-2560; Brunhouse, R., and Cebra, J. J., Mol. Immunol. 16 (1979) 907-917; Burton, D. R., et al., Nature 288 (1980) 338-344; Thommesen, J. E., et al., Mol. Immunol. 37 (2000) 995-1004; Idusogie, E. E., et al., J. Immunol. 164 (2000) 4178-4184; Hezareh, M., et al., J. Virol. 75 (2001) 12161-12168; Morgan, A., et al., Immunology 86 (1995) 319-324; and EP 0 307 434. Such binding sites are e.g. L234, L235, D270, N297, E318, K320, K322, P331 and P329 (numbering according to EU index of Kabat; Unless otherwise specified herein, numbering of amino acid residues in the Fc-region or constant region is according to the EU numbering system, also called the EU index, as described in Kabat, E. A. et al., Sequences of Proteins of Immunological Interest, 5th ed., Public Health Service, National Institutes of Health, Bethesda, Md. (1991), NIH Publication 91-3242). Antibodies of subclass IgG1, IgG2 and IgG3 usually show complement activation, C1q binding and C3 activation, whereas IgG4 do not activate the complement system, do not bind C1q and do not activate C3. An "Fc-region of an antibody" is a term well known to the skilled artisan and defined on the basis of papain cleavage of antibodies. In one embodiment the Fc-region is a human Fc-region. In one embodiment the Fc-region is of the human IgG4 subclass comprising the mutations S228P and/or L235E (numbering according to EU index of Kabat). In one embodiment the Fc-region is of the human IgG1 subclass comprising the mutations L234A and L235A (numbering according to EU index of Kabat).

"Framework" or "FR" refers to variable domain residues other than hypervariable region (HVR) residues. The FR of a variable domain generally consists of four FR domains: FR1, FR2, FR3, and FR4. Accordingly, the HVR and FR sequences generally appear in the following sequence in VH (or VL): FR1-H1(L1)-FR2-H2(L2)-FR3-H3(L3)-FR4.

The terms "full length antibody", "intact antibody," and "whole antibody" are used herein interchangeably to refer to an antibody having a structure substantially similar to a native antibody structure or having heavy chains that contain an Fc region as defined herein.

The terms "host cell", "host cell line", and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

A "human consensus framework" is a framework which represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat, E. A. et al., Sequences of Proteins of Immunological Interest, 5th ed., Bethesda Md. (1991), NIH Publication 91-3242, Vols. 1-3. In one embodiment, for the VL, the subgroup is subgroup kappa I as in Kabat et al., supra. In one embodiment, for the VH, the subgroup is subgroup III as in Kabat et al., supra.

A "humanized" antibody refers to a chimeric antibody comprising amino acid residues from non-human HVRs and amino acid residues from human FRs. In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

The term "hypervariable region" or "HVR", as used herein, refers to each of the regions of an antibody variable domain comprising the amino acid residue stretches which are hypervariable in sequence ("complementarity determining regions" or "CDRs") and/or form structurally defined loops ("hypervariable loops"), and/or contain the antigen-contacting residues ("antigen contacts"). Generally, antibodies comprise six HVRs; three in the VH (H1, H2, H3), and three in the VL (L1, L2, L3).

HVRs include
(a) hypervariable loops occurring at amino acid residues 26-32 (L1), 50-52 (L2), 91-96 (L3), 26-32 (H1), 53-55 (H2), and 96-101 (H3) (Chothia, C. and Lesk, A. M., J. Mol. Biol. 196 (1987) 901-917);
(b) CDRs occurring at amino acid residues 24-34 (L1), 50-56 (L2), 89-97 (L3), 31-35b (H1), 50-65 (H2), and 95-102 (H3) (Kabat, E. A. et al., Sequences of Proteins of Immunological Interest, 5th ed. Public Health Service, National Institutes of Health, Bethesda, Md. (1991), NIH Publication 91-3242.);

(c) antigen contacts occurring at amino acid residues 27c-36 (L1), 46-55 (L2), 89-96 (L3), 30-35b (H1), 47-58 (H2), and 93-101 (H3) (MacCallum et al. J. Mol. Biol. 262: 732-745 (1996)); and (d) combinations of (a), (b), and/or (c), including amino acid residues 46-56 (L2), 47-56 (L2), 48-56 (L2), 49-56 (L2), 26-35 (H1), 26-35b (H1), 49-65 (H2), 93-102 (H3), and 94-102 (H3).

Unless otherwise indicated, HVR residues and other residues in the variable domain (e.g., FR residues) are numbered herein according to Kabat et al., supra.

An "immunoconjugate" is an antibody conjugated to one or more heterologous molecule(s), including but not limited to a cytotoxic agent.

An "individual" or "subject" is a mammal. Mammals include, but are not limited to, domesticated animals (e.g. cows, sheep, cats, dogs, and horses), primates (e.g., humans and non-human primates such as monkeys), rabbits, and rodents (e.g., mice and rats). In certain embodiments, the individual or subject is a human.

An "isolated" antibody is one which has been separated from a component of its natural environment. In some embodiments, an antibody is purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC). For review of methods for assessment of antibody purity, see, e.g., Flatman, S. et al., J. Chromatogr. B 848 (2007) 79-87.

An "isolated" nucleic acid refers to a nucleic acid molecule that has been separated from a component of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

"Isolated nucleic acid encoding an anti-human CD19 antibody" refers to one or more nucleic acid molecules encoding antibody heavy and light chains (or fragments thereof), including such nucleic acid molecule(s) in a single vector or separate vectors, and such nucleic acid molecule(s) present at one or more locations in a host cell.

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

A "naked antibody" refers to an antibody that is not conjugated to a heterologous moiety (e.g., a cytotoxic moiety) or radiolabel. The naked antibody may be present in a pharmaceutical formulation.

"Native antibodies" refer to naturally occurring immunoglobulin molecules with varying structures. For example, native IgG antibodies are heterotetrameric glycoproteins of about 150,000 daltons, composed of two identical light chains and two identical heavy chains that are disulfide-bonded. From N- to C-terminus, each heavy chain has a variable region (VH), also called a variable heavy domain or a heavy chain variable domain, followed by three constant domains (CH1, CH2, and CH3), whereby between the first and the second constant domain a hinge region is located. Similarly, from N- to C-terminus, each light chain has a variable region (VL), also called a variable light domain or a light chain variable domain, followed by a constant light (CL) domain. The light chain of an antibody may be assigned to one of two types, called kappa (κ) and lambda (λ), based on the amino acid sequence of its constant domain.

The term "package insert" is used to refer to instructions customarily included in commercial packages of therapeutic products, that contain information about the indications, usage, dosage, administration, combination therapy, contraindications and/or warnings concerning the use of such therapeutic products.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, Calif., or may be compiled from the source code. The ALIGN-2 program should be compiled for use on a UNIX operating system, including digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction X/Y where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

The term "pharmaceutical formulation" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

The term "CD19", as used herein, refers to human B-lymphocyte antigen CD19 (alternative name(s) are: Differentiation antigen CD19, B-lymphocyte surface antigen B4, T-cell surface antigen Leu-12; UniProtKB P15391-1 (isoform 1; SEQ ID NO: 33) and P15391-2 (isoform 2; SEQ ID NO: 34)). The term encompasses "full-length" unprocessed human CD19 as well as any form of human CD19 that results from processing in the cell as long as the antibody as reported herein binds thereto.

As used herein, "treatment" (and grammatical variations thereof such as "treat" or "treating") refers to clinical intervention in an attempt to alter the natural course of the individual being treated, and can be performed either for prophylaxis or during the course of clinical pathology. Desirable effects of treatment include, but are not limited to, preventing occurrence or recurrence of a disease, alleviation of symptoms, diminishment of any direct or indirect pathological consequences of the disease, preventing metastasis, decreasing the rate of disease progression, amelioration or palliation of the disease state, and remission or improved prognosis. In some embodiments, antibodies as reported herein are used to delay development of a disease or to slow the progression of a disease.

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three hypervariable regions (HVRs). (see, e.g., Kindt, T. J., et al. Kuby Immunology, 6th ed., W.H. Freeman and Co., N.Y. (2007), page 91) A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively. See, e.g., Portolano, S. et al., J. Immunol. 150 (1993) 880-887; Clackson, T. et al., Nature 352 (1991) 624-628).

The term "vector", as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors".

II. Compositions and Methods

In one aspect, the invention is based, in part, on the finding that for removing multiple deamidation hotspots in a humanized anti-human CD19 antibody a single mutation is sufficient. In certain embodiments, antibodies that bind to human CD19 are provided. Antibodies as reported herein are useful, e.g., for diagnosis or treatment.

A. Exemplary Anti-Human CD19 Antibodies

It has been found that the wild-type humanized anti-human CD19 antibody has three deamidation hotspots in the HVR-L1: NSNGNT (SEQ ID NO: 36). Additionally it has been found that in the HVR-H2 a further deamidation hotspot is present: KFNG (SEQ ID NO: 37).

In one aspect, herein is provided an isolated humanized antibody that specifically bind to human CD19 and that has improved stability, especially deamidation stability in the heavy and light chain HVRs HVR-H2 and HVR-L1, compared to other humanized variants. In this improved humanized anti-human CD19 antibody the human/cynomolgus cross-reactivity of the parental murine antibody is retained.

To address the deamidation hotspot in the HVR-H2 an N (Asn) to Q (Gln) point mutation at position 64 (numbering according to Kabat) has been introduced. Thus, the antibody as reported herein has a HVR-H2 comprising the amino acid sequence TEKFQG (SEQ ID NO: 38). In one preferred embodiment the humanized anti-human CD19 antibody comprises a HVR-H2 that has the amino acid sequence YINPYNDGSK YTEKFQG (SEQ ID NO: 11).

To address the deamidation hotspots in the light chain and to obtain a humanized anti-human CD19 antibody with improved deamidation stability individual mutations at Kabat position 27d, 27e, 28 and 29 and a double mutation at positions 27e and 28 (numbering according to Kabat) were introduced. In total 9 variants (var.1 to var.9; SEQ ID NO: 60 to 68 and 70) of the wild-type humanized antibody (var.0; SEQ ID NO: 59 and 69) have been generated.

| Kabat position LC: | 2222 7789 de | Kabat position HC: | 6 4 |
|---|---|---|---|
| var.0:wt | QSLENSNGNTYL | | TEKFNGKATL |
| var.1:N27dH | QSLEHSNGNTYL | | TEKFQGRVTM |
| var.2:N27dQ | QSLEQSNGNTYL | | TEKFQGRVTM |

-continued

| | | |
|---|---|---|
| var.3:S27eA | QSLENANGNTYL | TEKFQGRVTM |
| var.4:S27eV | QSLENVNGNTYL | TEKFQGRVTM |
| var.5:S27eP | QSLENPNGNTYL | TEKFQGRVTM |
| var.6:N28Q | QSLENSQGNTYL | TEKFQGRVTM |
| var.7:G29A | QSLENSNANTYL | TEKFQGRVTM |
| var.8:G29V | QSLENSNVNTYL | TEKFQGRVTM |
| var.9:S27eP/N28S | QSLENPSGNTYL | TEKFQGRVTM |

| parameter | variant | | | | | | | | | |
|---|---|---|---|---|---|---|---|---|---|---|
| | 0 | 1 | 2 | 3 | 4 | 5 | 6 | 7 | 8 | 9 |
| $K_D$ (BIAcore) [nM] | 5 | 250 | 136 | 2 | 1 | 6 | 54 | 4 | 16 | 45 |
| $t_{1/2}$ [min] | — | 0.1 | 1.1 | 105.2 | 191.5 | 43.6 | 4.4 | 51.5 | 17.6 | 4 |
| human CD19 binding after pH 7.4 incubation [%] | 46 | 0 | 75 | 84 | 85 | 95 | 91 | 72 | 83 | 83 |
| human CD19 binding after pH 6.0 incubation [%] | 90 | 0 | 95 | 95 | 97 | 99 | 97 | 86 | 91 | 87 |
| SEC main peak after incubation [%] | >95 | >95 | >95 | >95 | >95 | >95 | >95 | >95 | >95 | — |

It has been found that with a single mutation at position 27e according to Kabat from S (serine) to P (proline) all deamidation hotspots in the HVR-L1 can be addressed. This is a mutation not of the deamidation prone N (asparagine) residue but of a neighboring residue.

Thus, the antibody as reported herein has a HVR-L1 comprising the amino acid sequence LENPNGNT (SEQ ID NO: 39). In one embodiment the humanized anti-human CD19 antibody comprises a HVR-L1 that has the amino acid sequence LENPSGNT (SEQ ID NO: 40). In one preferred embodiment the humanized anti-human CD19 antibody comprises a HVR-L1 that has the amino acid sequence RSSQSLENPN GNTYLN (SEQ ID NO: 20). In one preferred embodiment the humanized anti-human CD19 antibody comprises a HVR-L1 that has the amino acid sequence RSSQSLENPS GNTYLN (SEQ ID NO: 28).

Additionally these antibodies maintain the cross-reactivity to cynomolgus CD19 as shown in the following Table.

| EC50 [µg/ml] | var.0 | var.5 | var.9 |
|---|---|---|---|
| huCD19 ECD | 0.087 | 0.084 | 0.089 |
| cyCD19 ECD | 0.313 | 0.255 | 0.435 |

Thus, in one embodiment the anti-human CD19 antibody specifically binds to human CD19 and cynomolgus CD 19.

The wild-type humanized anti-human CD19 antibody (var.0) shows after purification approx. 7.5% deamidation. After storage for two weeks at pH 7.4 the amount of deamidated antibody is increased to approx. 18.5%. The variant antibody with an S27eP mutation (var.5) shows approx. 2% deamidation and 2% succinimide formation after purification. During storage at pH 7.4 for two weeks only approx. 7.5% deamidated antibody is present.

In one aspect, herein is provided an isolated humanized antibody that specifically binds to human CD19 and cynomolgus CD19 comprising a HVR-H2 of SEQ ID NO: 11 and HVR-L1 of SEQ ID NO: 20 or 28.

In one aspect, herein is provided an anti-human CD19 antibody comprising at least one, two, three, four, five, or six HVRs selected from (a) HVR-H1 comprising the amino acid sequence of SEQ ID NO: 03, (b) HVR-H2 comprising the amino acid sequence of SEQ ID NO: 11, (c) HVR-H3 comprising the amino acid sequence of SEQ ID NO: 05, (d) HVR-L1 comprising the amino acid sequence of SEQ ID NO: 20, (e) HVR-L2 comprising the amino acid sequence of SEQ ID NO: 07, and (f) HVR-L3 comprising the amino acid sequence of SEQ ID NO: 08.

In one aspect, herein is provided an anti-human CD19 antibody comprising at least one, two, three, four, five, or six HVRs selected from (a) HVR-H1 comprising the amino acid sequence of SEQ ID NO: 03, (b) HVR-H2 comprising the amino acid sequence of SEQ ID NO: 11, (c) HVR-H3 comprising the amino acid sequence of SEQ ID NO: 05, (d) HVR-L1 comprising the amino acid sequence of SEQ ID NO: 28, (e) HVR-L2 comprising the amino acid sequence of SEQ ID NO: 07, and (f) HVR-L3 comprising the amino acid sequence of SEQ ID NO: 08.

In one aspect, herein is provided an anti-human CD19 antibody comprising at least one, at least two, or all three VH HVR sequences selected from (a) HVR-H1 comprising the amino acid sequence of SEQ ID NO: 03, (b) HVR-H2 comprising the amino acid sequence of SEQ ID NO: 11, and (c) HVR-H3 comprising the amino acid sequence of SEQ ID NO: 05. In one embodiment, the antibody comprises HVR-H3 comprising the amino acid sequence of SEQ ID NO: 05. In another embodiment, the antibody comprises HVR-H3 comprising the amino acid sequence of SEQ ID NO: 05 and HVR-L3 comprising the amino acid sequence of SEQ ID NO: 08. In a further embodiment, the antibody comprises HVR-H3 comprising the amino acid sequence of SEQ ID NO: 05, HVR-L3 comprising the amino acid sequence of SEQ ID NO: 08, and HVR-H2 comprising the amino acid sequence of SEQ ID NO: 11. In a further embodiment, the antibody comprises (a) HVR-H1 comprising the amino acid sequence of SEQ ID NO: 03, (b) HVR-H2 comprising the amino acid sequence of SEQ ID NO: 11, and (c) HVR-H3 comprising the amino acid sequence of SEQ ID NO: 05.

In another aspect, herein is provided an antibody comprising at least one, at least two, or all three VL HVR sequences selected from (a) HVR-L1 comprising the amino acid sequence of SEQ ID NO: 20, (b) HVR-L2 comprising the amino acid sequence of SEQ ID NO: 07, and (c) HVR-L3 comprising the amino acid sequence of SEQ ID NO: 08. In one embodiment, the antibody comprises (a) HVR-L1 comprising the amino acid sequence of SEQ ID NO: 20, (b) HVR-L2 comprising the amino acid sequence of SEQ ID NO: 07, and (c) HVR-L3 comprising the amino acid sequence of SEQ ID NO: 08.

In another aspect, herein is provided an antibody comprising at least one, at least two, or all three VL HVR sequences selected from (a) HVR-L1 comprising the amino acid sequence of SEQ ID NO: 28, (b) HVR-L2 comprising the amino acid sequence of SEQ ID NO: 07, and (c) HVR-L3 comprising the amino acid sequence of SEQ ID NO: 08. In one embodiment, the antibody comprises (a) HVR-L1 comprising the amino acid sequence of SEQ ID NO: 28, (b) HVR-L2 comprising the amino acid sequence of SEQ ID NO: 07, and (c) HVR-L3 comprising the amino acid sequence of SEQ ID NO: 08.

In another aspect, an antibody as reported herein comprises (a) a VH domain comprising at least one, at least two, or all three VH HVR sequences selected from (i) HVR-H1 comprising the amino acid sequence of SEQ ID NO: 03, (ii) HVR-H2 comprising the amino acid sequence of SEQ ID NO: 11 and (iii) HVR-H3 comprising an amino acid sequence selected from SEQ ID NO: 05, and (b) a VL domain comprising at least one, at least two, or all three VL HVR sequences selected from (i) HVR-L1 comprising the amino acid sequence of SEQ ID NO: 20, (ii) HVR-L2 comprising the amino acid sequence of SEQ ID NO: 07, and (c) HVR-L3 comprising the amino acid sequence of SEQ ID NO: 08.

In another aspect, an antibody as reported herein comprises (a) a VH domain comprising at least one, at least two, or all three VH HVR sequences selected from (i) HVR-H1 comprising the amino acid sequence of SEQ ID NO: 03, (ii) HVR-H2 comprising the amino acid sequence of SEQ ID NO: 11 and (iii) HVR-H3 comprising an amino acid sequence selected from SEQ ID NO: 05, and (b) a VL domain comprising at least one, at least two, or all three VL HVR sequences selected from (i) HVR-L1 comprising the amino acid sequence of SEQ ID NO: 28, (ii) HVR-L2 comprising the amino acid sequence of SEQ ID NO: 07, and (c) HVR-L3 comprising the amino acid sequence of SEQ ID NO: 08.

In another aspect, herein is provided an antibody comprising (a) HVR-H1 comprising the amino acid sequence of SEQ ID NO: 03, (b) HVR-H2 comprising the amino acid sequence of SEQ ID NO: 11, (c) HVR-H3 comprising the amino acid sequence of SEQ ID NO: 05, (d) HVR-L1 comprising the amino acid sequence of SEQ ID NO: 20, (e) HVR-L2 comprising the amino acid sequence of SEQ ID NO: 07, and (f) HVR-L3 comprising an amino acid sequence selected from SEQ ID NO:08.

In another aspect, herein is provided an antibody comprising (a) HVR-H1 comprising the amino acid sequence of SEQ ID NO: 03, (b) HVR-H2 comprising the amino acid sequence of SEQ ID NO: 11, (c) HVR-H3 comprising the amino acid sequence of SEQ ID NO: 05, (d) HVR-L1 comprising the amino acid sequence of SEQ ID NO: 28, (e) HVR-L2 comprising the amino acid sequence of SEQ ID NO: 07, and (f) HVR-L3 comprising an amino acid sequence selected from SEQ ID NO:08.

The anti-human CD19 antibody as reported herein is a humanized antibody. In one embodiment, the humanized anti-human CD19 antibody comprises HVRs as in any of the above embodiments, and further comprises an acceptor human framework, e.g. a human immunoglobulin (germline) framework or a human consensus framework.

In another aspect, an anti-human CD19 antibody comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO: 09. In certain embodiments, a VH sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-human CD19 antibody comprising that sequence retains the ability to bind to human CD19. In certain embodiments, a total of 1 to 10 amino acids have been substituted, inserted and/or deleted in SEQ ID NO: 09. In certain embodiments, substitutions, insertions, or deletions occur in regions outside the HVRs (i.e., in the FRs). Optionally, the anti-human CD19 antibody comprises the VH sequence in SEQ ID NO: 09, including post-translational modifications of that sequence. In a particular embodiment, the VH comprises one, two or three HVRs selected from: (a) HVR-H1 comprising the amino acid sequence of SEQ ID NO: 03, (b) HVR-H2 comprising the amino acid sequence of SEQ ID NO: 11, and (c) HVR-H3 comprising the amino acid sequence of SEQ ID NO: 05.

In another aspect, an anti-human CD19 antibody is provided, wherein the antibody comprises a light chain variable domain (VL) having at least 90%, 91%, 92%, 93%, 94%, 95%, 96%, 97%, 98%, 99%, or 100% sequence identity to the amino acid sequence of SEQ ID NO: 19 or SEQ ID NO: 27 (SEQ ID NO: 19 and SEQ ID NO: 27 differ at a single amino acid position). In certain embodiments, a VL sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-human CD19 antibody comprising that sequence retains the ability to bind to human CD19. In certain embodiments, a total of 1 to 10 amino acids have been substituted, inserted and/or deleted in SEQ ID NO: 19 or SEQ ID NO: 27. In certain embodiments, the substitutions, insertions, or deletions occur in regions outside the HVRs (i.e., in the FRs). Optionally, the anti-human CD19 antibody comprises the VL sequence in SEQ ID NO:

19, including post-translational modifications of that sequence. Optionally, the anti-human CD19 antibody comprises the VL sequence in SEQ ID NO: 27, including post-translational modifications of that sequence. In a particular embodiment, the VL comprises one, two or three HVRs selected from (a) HVR-L1 comprising the amino acid sequence of SEQ ID NO: 20, (b) HVR-L2 comprising the amino acid sequence of SEQ ID NO: 07, and (c) HVR-L3 comprising the amino acid sequence of SEQ ID NO: 08. In a particular embodiment, the VL comprises one, two or three HVRs selected from (a) HVR-L1 comprising the amino acid sequence of SEQ ID NO: 28, (b) HVR-L2 comprising the amino acid sequence of SEQ ID NO: 07, and (c) HVR-L3 comprising the amino acid sequence of SEQ ID NO: 08.

In another aspect, an anti-human CD19 antibody is provided, wherein the antibody comprises a VH as in any of the embodiments provided above, and a VL as in any of the embodiments provided above. In one embodiment, the antibody comprises the VH and VL sequences in SEQ ID NO: 09 and SEQ ID NO: 19 or 27, respectively, including post-translational modifications of those sequences.

In a further aspect, herein is provided an antibody that binds to the same epitope as an anti-human CD19 antibody as reported herein. For example, in certain embodiments, an antibody is provided that binds to the same epitope as an anti-human CD19 antibody comprising a VH sequence of SEQ ID NO: 09 and a VL sequence of SEQ ID NO: 19.

In one embodiment, an anti-human CD19 antibody according to any of the above embodiments is a monoclonal antibody. In one embodiment, an anti-human CD19 antibody is an antibody fragment, e.g., an Fv, Fab, Fab', scFv, diabody, or F(ab')$_2$ fragment. In another embodiment, the antibody is a full length antibody, e.g., an intact IgG1 or IgG 4 antibody or other antibody class or isotype as defined herein.

In one embodiment of all aspects the antibody comprises (all positions according to EU index of Kabat)
 i) a homodimeric Fc-region of the human IgG1 subclass optionally with the mutations P329G, L234A and L235A, or
 ii) a homodimeric Fc-region of the human IgG4 subclass optionally with the mutations P329G, S228P and L235E, or
 iii) a homodimeric Fc-region of the human IgG1 subclass with the mutations (P329G, L234A, L235A) I253A, H310A, and H435A, or with the mutations (P329G, L234A, L235A) H310A, H433A, and Y436A, or
 iv) a heterodimeric Fc-region whereof
  a) one Fc-region polypeptide comprises the mutation T366W, and the other Fc-region polypeptide comprises the mutations T366S, L368A and Y407V, or
  b) one Fc-region polypeptide comprises the mutations T366W and Y349C, and the other Fc-region polypeptide comprises the mutations T366S, L368A, Y407V, and S354C, or
  c) one Fc-region polypeptide comprises the mutations T366W and S354C, and the other Fc-region polypeptide comprises the mutations T366S, L368A, Y407V and Y349C,
  or
 v) a heterodimeric Fc-region of the human IgG1 subclass whereof both Fc-region polypeptides comprise the mutations P329G, L234A and L235A and
  a) one Fc-region polypeptide comprises the mutation T366W, and the other Fc-region polypeptide comprises the mutations T366S, L368A and Y407V, or
  b) one Fc-region polypeptide comprises the mutations T366W and Y349C, and the other Fc-region polypeptide comprises the mutations T366S, L368A, Y407V, and S354C, or
  c) one Fc-region polypeptide comprises the mutations T366W and S354C, and the other Fc-region polypeptide comprises the mutations T366S, L368A, Y407V and Y349C,
  or
 vi) a heterodimeric Fc-region of the human IgG4 subclass whereof both Fc-region polypeptides comprise the mutations P329G, S228P and L235E and
  a) one Fc-region polypeptide comprises the mutation T366W, and the other Fc-region polypeptide comprises the mutations T366S, L368A and Y407V, or
  b) one Fc-region polypeptide comprises the mutations T366W and Y349C, and the other Fc-region polypeptide comprises the mutations T366S, L368A, Y407V, and S354C, or
  c) one Fc-region polypeptide comprises the mutations T366W and S354C, and the other Fc-region polypeptide comprises the mutations T366S, L368A, Y407V and Y349C,
  or
 vii) a combination of one of iii) with one of vi), v) and vi).

One aspect as reported herein is a bivalent, bispecific antibody comprising
 a) a first light chain and a first heavy chain of an antibody specifically binding to a first antigen, and
 b) a second light chain and a second heavy chain of an antibody specifically binding to a second antigen, wherein the variable domains VL and VH of the second light chain and the second heavy chain are replaced by each other,
 wherein the first antigen or the second antigen is human CD19.

The antibody under a) does not contain a modification as reported under b) and the heavy chain and the light chain under a) are isolated chains.

In the antibody under b)
 within the light chain
  the variable light chain domain VL is replaced by the variable heavy chain domain VH of said antibody,
 and
 within the heavy chain
  the variable heavy chain domain VH is replaced by the variable light chain domain VL of said antibody.

In one embodiment
 i) in the constant domain CL of the first light chain under a) the amino acid at position 124 (numbering according to Kabat) is substituted by a positively charged amino acid, and wherein in the constant domain CH1 of the first heavy chain under a) the amino acid at position 147 or the amino acid at position 213 (numbering according to Kabat EU index) is substituted by a negatively charged amino acid,
 or
 ii) in the constant domain CL of the second light chain under b) the amino acid at position 124 (numbering according to Kabat) is substituted by a positively charged amino acid, and wherein in the constant domain CH1 of the second heavy chain under b) the amino acid at position 147 or the amino acid at position 213 (numbering according to Kabat EU index) is substituted by a negatively charged amino acid.

In one preferred embodiment i) in the constant domain CL of the first light chain under a) the amino acid at position 124 is substituted independently by lysine (K), arginine (R) or histidine (H) (numbering according to Kabat) (in one preferred embodiment independently by lysine (K) or arginine (R)), and wherein in the constant domain CH1 of the first heavy chain under a) the amino acid at position 147 or the amino acid at position 213 is substituted independently by glutamic acid (E) or aspartic acid (D) (numbering according to Kabat EU index), or ii) in the constant domain CL of the second light chain under b) the amino acid at position 124 is substituted independently by lysine (K), arginine (R) or histidine (H) (numbering according to Kabat) (in one preferred embodiment independently by lysine (K) or arginine (R)), and wherein in the constant domain CH1 of the second heavy chain under b) the amino acid at position 147 or the amino acid at position 213 is substituted independently by glutamic acid (E) or aspartic acid (D) (numbering according to Kabat EU index).

In one embodiment in the constant domain CL of the second heavy chain the amino acids at position 124 and 123 are substituted by K (numbering according to Kabat EU index).

In one embodiment in the constant domain CH1 of the second light chain the amino acids at position 147 and 213 are substituted by E (numbering according to EU index of Kabat).

In one preferred embodiment in the constant domain CL of the first light chain the amino acids at position 124 and 123 are substituted by R and K, respectively, and in the constant domain CH1 of the first heavy chain the amino acids at position 147 and 213 are substituted by E (numbering according to Kabat EU index).

In one embodiment in the constant domain CL of the second heavy chain the amino acids at position 124 and 123 are substituted by K, and wherein in the constant domain CH1 of the second light chain the amino acids at position 147 and 213 are substituted by E, and in the variable domain VL of the first light chain the amino acid at position 38 is substituted by K, in the variable domain VH of the first heavy chain the amino acid at position 39 is substituted by E, in the variable domain VL of the second heavy chain the amino acid at position 38 is substituted by K, and in the variable domain VH of the second light chain the amino acid at position 39 is substituted by E (numbering according to Kabat EU index).

One aspect as reported herein is a bivalent, bispecific antibody comprising a) a first light chain and a first heavy chain of an antibody specifically binding to a first antigen, and b) a second light chain and a second heavy chain of an antibody specifically binding to a second antigen, wherein the variable domains VL and VH of the second light chain and the second heavy chain are replaced by each other, and wherein the constant domains CL and CH1 of the second light chain and the second heavy chain are replaced by each other, wherein the first antigen or the second antigen is human CD19.

The antibody under a) does not contain a modification as reported under b) and the heavy chain and the light chain and a) are isolated chains.

In the antibody under b)
within the light chain
the variable light chain domain VL is replaced by the variable heavy chain domain VH of said antibody, and the constant light chain domain CL is replaced by the constant heavy chain domain CH1 of said antibody; and
within the heavy chain
the variable heavy chain domain VH is replaced by the variable light chain domain VL of said antibody, and the constant heavy chain domain CH1 is replaced by the constant light chain domain CL of said antibody.

One aspect as reported herein is a bivalent, bispecific antibody comprising a) a first light chain and a first heavy chain of an antibody specifically binding to a first antigen, and b) a second light chain and a second heavy chain of an antibody specifically binding to a second antigen, wherein the constant domains CL and CH1 of the second light chain and the second heavy chain are replaced by each other, wherein the first antigen or the second antigen is human CD19.

The antibody under a) does not contain a modification as reported under b) and the heavy chain and the light chain under a) are isolated chains.

In the antibody under b)
within the light chain
the constant light chain domain CL is replaced by the constant heavy chain domain CH1 of said antibody; and within the heavy chain
the constant heavy chain domain CH1 is replaced by the constant light chain domain CL of said antibody.

One aspect as reported herein is a multispecific antibody comprising a) a full length antibody specifically binding to a first antigen and consisting of two antibody heavy chains and two antibody light chains, and b) one, two, three or four single chain Fab fragments specifically binding to one to four further antigens (i.e. a second and/or third and/or fourth and/or fifth antigen, preferably specifically binding to one further antigen, i.e. a second antigen), wherein said single chain Fab fragments under b) are fused to said full length antibody under a) via a peptidic linker at the C- or N-terminus of the heavy or light chain of said full length antibody, wherein the first antigen or one of the further antigens is human CD19.

In one embodiment one or two identical single chain Fab fragments binding to a second antigen are fused to the full length antibody via a peptidic linker at the C-terminus of the heavy or light chains of said full length antibody.

In one embodiment one or two identical single chain Fab fragments binding to a second antigen are fused to the full length antibody via a peptidic linker at the C-terminus of the heavy chains of said full length antibody.

In one embodiment one or two identical single chain Fab fragments binding to a second antigen are fused to the full length antibody via a peptidic linker at the C-terminus of the light chains of said full length antibody.

In one embodiment two identical single chain Fab fragments binding to a second antigen are fused to the full length antibody via a peptidic linker at the C-terminus of each heavy or light chain of said full length antibody.

In one embodiment two identical single chain Fab fragments binding to a second antigen are fused to the full length antibody via a peptidic linker at the C-terminus of each heavy chain of said full length antibody.

In one embodiment two identical single chain Fab fragments binding to a second antigen are fused to the full length antibody via a peptidic linker at the C-terminus of each light chain of said full length antibody.

One aspect as reported herein is a trivalent, bispecific antibody comprising
  a) a full length antibody specifically binding to a first antigen and consisting of two antibody heavy chains and two antibody light chains,
  b) a first polypeptide consisting of
    ba) an antibody heavy chain variable domain (VH), or
    bb) an antibody heavy chain variable domain (VH) and an antibody constant domain 1 (CH1),
    wherein said first polypeptide is fused with the N-terminus of its VH domain via a peptidic linker to the C-terminus of one of the two heavy chains of said full length antibody,
  c) a second polypeptide consisting of
    ca) an antibody light chain variable domain (VL), or
    cb) an antibody light chain variable domain (VL) and an antibody light chain constant domain (CL),
    wherein said second polypeptide is fused with the N-terminus of the VL domain via a peptidic linker to the C-terminus of the other of the two heavy chains of said full length antibody,
  and
  wherein the antibody heavy chain variable domain (VH) of the first
  polypeptide and the antibody light chain variable domain (VL) of the second
  polypeptide together form an antigen-binding site specifically binding to a
  second antigen,
  and
  wherein the first antigen or the second antigen is human CD19.

In one embodiment the antibody heavy chain variable domain (VH) of the polypeptide under b) and the antibody light chain variable domain (VL) of the polypeptide under c) are linked and stabilized via an interchain disulfide bridge by introduction of a disulfide bond between the following positions:
  i) heavy chain variable domain position 44 to light chain variable domain position 100, or
  ii) heavy chain variable domain position 105 to light chain variable domain position 43, or
  iii) heavy chain variable domain position 101 to light chain variable domain position 100 (numbering always according to Kabat EU index).

Techniques to introduce unnatural disulfide bridges for stabilization are described e.g. in WO 94/029350, Rajagopal, V., et al., Prot. Eng. (1997) 1453-59; Kobayashi, H., et al., Nuclear Medicine & Biology, Vol. 25, (1998) 387-393; or Schmidt, M., et al., Oncogene (1999) 18 1711-1721. In one embodiment the optional disulfide bond between the variable domains of the polypeptides under b) and c) is between heavy chain variable domain position 44 and light chain variable domain position 100. In one embodiment the optional disulfide bond between the variable domains of the polypeptides under b) and c) is between heavy chain variable domain position 105 and light chain variable domain position 43 (numbering always according to Kabat). In one embodiment a trivalent, bispecific antibody without said optional disulfide stabilization between the variable domains VH and VL of the single chain Fab fragments is preferred.

One aspect as reported herein is a trispecific or tetraspecific antibody, comprising
  a) a first light chain and a first heavy chain of a full length antibody which specifically binds to a first antigen, and
  b) a second (modified) light chain and a second (modified) heavy chain of a full length antibody which specifically binds to a second antigen, wherein the variable domains VL and VH are replaced by each other, and/or wherein the constant domains CL and CH1 are replaced by each other, and
  c) wherein one to four antigen binding peptides which specifically bind to one or two further antigens (i.e. to a third and/or fourth antigen) are fused via a peptidic linker to the C- or N-terminus of the light chains or heavy chains of a) and/or b),
  wherein the first antigen or the second antigen or one of the further antigens is human CD19.

The antibody under a) does not contain a modification as reported under b) and the heavy chain and the light chain and a) are isolated chains.

In one embodiment the trispecific or tetraspecific antibody comprises under c) one or two antigen binding peptides which specifically bind to one or two further antigens.

In one embodiment the antigen binding peptides are selected from the group of a scFv fragment and a scFab fragment.

In one embodiment the antigen binding peptides are scFv fragments.

In one embodiment the antigen binding peptides are scFab fragments.

In one embodiment the antigen binding peptides are fused to the C-terminus of the heavy chains of a) and/or b).

In one embodiment the trispecific or tetraspecific antibody comprises under c) one or two antigen binding peptides which specifically bind to one further antigen.

In one embodiment the trispecific or tetraspecific antibody comprises under c) two identical antigen binding peptides which specifically bind to a third antigen. In one preferred embodiment such two identical antigen binding peptides are fused both via the same peptidic linker to the C-terminus of the heavy chains of a) and b). In one preferred embodiment the two identical antigen binding peptides are either a scFv fragment or a scFab fragment.

In one embodiment the trispecific or tetraspecific antibody comprises under c) two antigen binding peptides which specifically bind to a third and a fourth antigen. In one embodiment said two antigen binding peptides are fused both via the same peptide connector to the C-terminus of the heavy chains of a) and b). In one preferred embodiment said two antigen binding peptides are either a scFv fragment or a scFab fragment.

One aspect as reported herein is a bispecific, tetravalent antibody comprising
  a) two light chains and two heavy chains of an antibody, which specifically bind to a first antigen (and comprise two Fab fragments), b) two additional Fab fragments of an antibody, which specifically bind to a second antigen, wherein said additional Fab fragments are fused both via a peptidic linker either to the C- or N-termini of the heavy chains of a), and wherein in the Fab fragments the following modifications were performed
- i) in both Fab fragments of a), or in both Fab fragments of b), the variable domains VL and VH are replaced by each other, and/or the constant domains CL and CH1 are replaced by each other, or
- ii) in both Fab fragments of a) the variable domains VL and VH are replaced by each other, and the constant domains CL and CH1 are replaced by each other, and in both Fab fragments of b) the variable domains VL and VH are replaced by each other, or the constant domains CL and CH1 are replaced by each other, or
- iii) in both Fab fragments of a) the variable domains VL and VH are replaced by each other, or the constant domains CL and CH1 are replaced by each other, and in both Fab fragments of b) the variable domains VL and VH are replaced by each other, and the constant domains CL and CH1 are replaced by each other, or
- iv) in both Fab fragments of a) the variable domains VL and VH are replaced by each other, and in both Fab fragments of b) the constant domains CL and CH1 are replaced by each other, or
- v) in both Fab fragments of a) the constant domains CL and CH1 are replaced by each other, and in both Fab fragments of b) the variable domains VL and VH are replaced by each other, wherein the first antigen or the second antigen is human CD19.

In one embodiment said additional Fab fragments are fused both via a peptidic linker either to the C-termini of the heavy chains of a), or to the N-termini of the heavy chains of a).

In one embodiment said additional Fab fragments are fused both via a peptidic linker either to the C-termini of the heavy chains of a).

In one embodiment said additional Fab fragments are fused both via a peptide connector to the N-termini of the heavy chains of a).

In one embodiment in the Fab fragments the following modifications are performed:
- i) in both Fab fragments of a), or in both Fab fragments of b), the variable domains VL and VH are replaced by each other, and/or the constant domains CL and CH1 are replaced by each other.

In one embodiment in the Fab fragments the following modifications are performed:
- i) in both Fab fragments of a) the variable domains VL and VH are replaced by each other, and/or the constant domains CL and CH1 are replaced by each other.

In one embodiment in the Fab fragments the following modifications are performed:
- i) in both Fab fragments of a) the constant domains CL and CH1 are replaced by each other.

In one embodiment in the Fab fragments the following modifications are performed:
- i) in both Fab fragments of b) the variable domains VL and VH are replaced by each other, and/or the constant domains CL and CH1 are replaced by each other.

In one embodiment in the Fab fragments the following modifications are performed:
- i) in both Fab fragments of b) the constant domains CL and CH1 are replaced by each other.

One aspect as reported herein is a bispecific, tetravalent antibody comprising:
- a) a (modified) heavy chain of a first antibody, which specifically binds to a first antigen and comprises a first VH-CH1 domain pair, wherein to the C-terminus of said heavy chain the N-terminus of a second VH-CH1 domain pair of said first antibody is fused via a peptidic linker,
- b) two light chains of said first antibody of a),
- c) a (modified) heavy chain of a second antibody, which specifically binds to a second antigen and comprises a first VH-CL domain pair, wherein to the C-terminus of said heavy chain the N-terminus of a second VH-CL domain pair of said second antibody is fused via a peptidic linker, and
- d) two (modified) light chains of said second antibody of c), each comprising a CL-CH1 domain pair, wherein the first antigen or the second antigen is human CD19.

One aspect as reported herein is a bispecific antibody comprising
- a) the heavy chain and the light chain of a first full length antibody that specifically binds to a first antigen, and
- b) the heavy chain and the light chain of a second full length antibody that specifically binds to a second antigen, wherein the N-terminus of the heavy chain is connected to the C-terminus of the light chain via a peptidic linker, wherein the first antigen or the second antigen is human CD19.

The antibody under a) does not contain a modification as reported under b) and the heavy chain and the light chain are isolated chains.

One aspect as reported herein is a bispecific antibody comprising
- a) a full length antibody specifically binding to a first antigen and consisting of two antibody heavy chains and two antibody light chains, and
- b) an Fv fragment specifically binding to a second antigen comprising a $VH^2$ domain and a $VL^2$ domain, wherein both domains are connected to each other via a disulfide bridge, wherein only either the $VH^2$ domain or the $VL^2$ domain is fused via a peptidic linker to the heavy or light chain of the full length antibody specifically binding to a first antigen, wherein the first antigen or the second antigen is human CD19.

In the bispecific the heavy chains and the light chains under a) are isolated chains.

In one embodiment the other of the $VH^2$ domain or the $VL^2$ domain is not fused via a peptide linker to the heavy or light chain of the full length antibody specifically binding to a first antigen.

In all aspects as reported herein the first light chain comprises a VL domain and a CL domain and the first heavy chain comprises a VH domain, a CH1 domain, a hinge region, a CH2 domain and a CH3 domain.

One aspect as reported herein is a bispecific trivalent antibody comprising
- a) two Fab fragments that specifically binds to a first antigen,
- b) one CrossFab fragment that specifically binds to a second antigen in which the CH1 and the CL domain are exchanged for each other,
- c) one Fc-region comprising a first Fc-region heavy chain and a second Fc-region heavy chain, wherein the C-terminus of CH1 domains of the two Fab fragments are connected to the N-terminus of the heavy chain Fc-region polypeptides, and wherein the C-terminus of the CL domain of the CrossFab fragment is connected to the N-terminus of the VH domain of one of the Fab fragments, and wherein the first antigen or the second antigen is human CD19.

One aspect as reported herein is a bispecific trivalent antibody comprising
- a) a first and a second Fab fragment that each specifically bind to a first antigen,
- b) one CrossFab fragment that specifically binds to a second antigen in which the CH1 and the CL domain are exchanged for each other,
- c) one Fc-region comprising a first Fc-region heavy chain and a second Fc-region heavy chain, wherein the C-terminus of CH1 domain of the first Fab fragment is connected to the N-terminus of one of the heavy chain Fc-region polypeptides and the C-terminus of the CL-domain of the CrossFab fragment is connected to the N-terminus of the other heavy chain Fc-region polypeptide, and wherein the C-terminus of the CH1 domain of the second Fab fragment is connected to the N-terminus of the VH domain of the first Fab fragment or to the N-terminus of the VH domain of the CrossFab fragment, and wherein the first antigen or the second antigen is human CD19.

One aspect as reported herein is a bispecific trivalent antibody comprising
- a) a first and a second Fab fragment that each specifically bind to a first antigen,
- b) one CrossFab fragment that specifically binds to a second antigen in which the VH and the VL domain are exchanged for each other,
- c) one Fc-region comprising a first Fc-region heavy chain and a second Fc-region heavy chain, wherein the C-terminus of CH1 domain of the first Fab fragment is connected to the N-terminus of one of the heavy chain Fc-region polypeptides and the C-terminus of the CH1-domain of the CrossFab fragment is connected to the N-terminus of the other heavy chain Fc-region polypeptide, and wherein the C-terminus of the CH1 domain of the second Fab fragment is connected to the N-terminus of the VH domain of the first Fab fragment or to the N-terminus of the VL domain of the CrossFab fragment, and wherein the first antigen or the second antigen is human CD19.

One aspect as reported herein is a bispecific antibody comprising
- a) a full length antibody specifically binding to a first antigen and consisting of two antibody heavy chains and two antibody light chains, and
- b) a Fab fragment specifically binding to a second antigen comprising a $VH^2$ domain and a $VL^2$ domain comprising a heavy chain fragment and a light chain fragment, wherein
    within the light chain fragment
      the variable light chain domain $VL^2$ is replaced by the variable heavy chain domain $VH^2$ of said antibody,
    and
    within the heavy chain fragment
      the variable heavy chain domain $VH^2$ is replaced by the variable light chain domain $VL^2$ of said antibody wherein the heavy chain Fab fragment is inserted between the CH1 domain of one of the heavy chains of the full length antibody and the respective Fc-region of the full length antibody, and the N-terminus of the light chain Fab fragment is conjugated to the C-terminus of the light chain of the full length antibody that is paired with the heavy chain of the full length antibody into which the heavy chain Fab fragment has been inserted, and wherein the first antigen or the second antigen is human CD19.

One aspect as reported herein is a bispecific antibody comprising
- a) a full length antibody specifically binding to a first antigen and consisting of two antibody heavy chains and two antibody light chains, and
- b) a Fab fragment specifically binding to a second antigen comprising a $VH^2$ domain and a $VL^2$ domain comprising a heavy chain fragment and a light chain fragment, wherein
    within the light chain fragment
      the variable light chain domain $VL^2$ is replaced by the variable heavy chain domain $VH^2$ of said antibody,
    and
    within the heavy chain fragment
      the variable heavy chain domain $VH^2$ is replaced by the variable light chain domain $VL^2$ of said antibody wherein the C-terminus of the heavy chain fragment of the Fab fragment is conjugated to the N-terminus of one of the heavy chains of the full length antibody and the C-terminus of the light chain fragment of the Fab fragment is conjugated to the N-terminus of the light chain of the full length antibody that pairs with the heavy chain of the full length antibody to which the heavy chain fragment of the Fab fragment is conjugated, and wherein the first antigen or the second antigen is human CD19.

In one embodiment of all aspects the antibody as reported herein is a multispecific antibody, which requires heterodimerization of at least two heavy chain polypeptides, and wherein the antibody specifically binds to human transferrin receptor and a second non-human transferrin receptor antigen.

Several approaches for CH3-modifications in order to support heterodimerization have been described, for example in WO 96/27011, WO 98/050431, EP 1870459, WO 2007/110205, WO 2007/147901, WO 2009/089004, WO 2010/129304, WO 2011/90754, WO 2011/143545, WO 2012/058768, WO 2013/157954, WO 2013/096291, which are herein included by reference. Typically, in the approaches known in the art, the CH3 domain of the first heavy chain and the CH3 domain of the second heavy chain are both engineered in a complementary manner so that the heavy chain comprising one engineered CH3 domain can no longer homodimerize with another heavy chain of the same structure (e.g. a CH3-engineered first heavy chain can no longer homodimerize with another CH3-engineered first heavy chain; and a CH3-engineered second heavy chain can no longer homodimerize with another CH3-engineered second heavy chain). Thereby the heavy chain comprising one engineered CH3 domain is forced to heterodimerize with another heavy chain comprising the CH3 domain, which is engineered in a complementary manner. For this embodiment, the CH3 domain of the first heavy chain and the CH3 domain of the second heavy chain are engineered in a complementary manner by amino acid substitutions, such that the first heavy chain and the second heavy chain are forced to heterodimerize, whereas the first heavy chain and the second heavy chain can no longer homodimerize (e.g. for steric reasons).

The different approaches for supporting heavy chain heterodimerization known in the art, that were cited and included above, are contemplated as different alternatives used in providing a multispecific antibody as reported herein, which comprises a "non-crossed Fab region" derived from a first antibody, which specifically binds to a first antigen, and a "crossed Fab region" derived from a second antibody, which specifically binds to a second antigen, in combination with the particular amino acid substitutions described above.

The CH3 domains of the multispecific antibody as reported herein can be altered by the "knob-into-holes" technology which is described in detail with several examples in e.g. WO 96/027011, Ridgway, J. B., et al., Protein Eng. 9 (1996) 617-621; and Merchant, A. M., et al., Nat. Biotechnol. 16 (1998) 677-681. In this method the interaction surfaces of the two CH3 domains are altered to increase the heterodimerization of both heavy chains containing these two CH3 domains. Each of the two CH3 domains (of the two heavy chains) can be the "knob", while the other is the "hole". The introduction of a disulfide bridge further stabilizes the heterodimers (Merchant, A. M., et al., Nature Biotech. 16 (1998) 677-681; Atwell, S., et al., J. Mol. Biol. 270 (1997) 26-35) and increases the yield.

In one preferred embodiment the multispecific antibody as reported herein comprises a T366W mutation in the CH3 domain of the "knobs chain" and T366S, L368A, Y407V mutations in the CH3 domain of the "hole-chain" (numbering according to Kabat EU index). An additional interchain disulfide bridge between the CH3 domains can also be used (Merchant, A. M., et al., Nature Biotech. 16 (1998) 677-681) e.g. by introducing a Y349C mutation into the CH3 domain of the "knobs chain" and a E356C mutation or a S354C mutation into the CH3 domain of the "hole chain". Thus in a another preferred embodiment, the multispecific antibody as reported herein comprises the Y349C and T366W mutations in one of the two CH3 domains and the E356C, T366S, L368A and Y407V mutations in the other of the two CH3 domains or the multispecific antibody as reported herein comprises the Y349C and T366W mutations in one of the two CH3 domains and the S354C, T366S, L368A and Y407V mutations in the other of the two CH3 domains (the additional Y349C mutation in one CH3 domain and the additional E356C or S354C mutation in the other CH3 domain forming a interchain disulfide bridge) (numbering according to Kabat EU index).

But also other knobs-in-holes technologies as described by EP 1 870 459A1, can be used alternatively or additionally. In one embodiment the multispecific antibody as reported herein comprises the R409D and K370E mutations in the CH3 domain of the "knobs chain" and the D399K and E357K mutations in the CH3 domain of the "hole-chain" (numbering according to Kabat EU index).

In one embodiment the multispecific antibody as reported herein comprises a T366W mutation in the CH3 domain of the "knobs chain" and the T366S, L368A and Y407V mutations in the CH3 domain of the "hole chain" and additionally the R409D and K370E mutations in the CH3 domain of the "knobs chain" and the D399K and E357K mutations in the CH3 domain of the "hole chain" (numbering according to the Kabat EU index).

In one embodiment the multispecific antibody as reported herein comprises the Y349C and T366W mutations in one of the two CH3 domains and the S354C, T366S, L368A and Y407V mutations in the other of the two CH3 domains, or the multispecific antibody as reported herein comprises the Y349C and T366W mutations in one of the two CH3 domains and the S354C, T366S, L368A and Y407V mutations in the other of the two CH3 domains and additionally the R409D and K370E mutations in the CH3 domain of the "knobs chain" and the D399K and E357K mutations in the CH3 domain of the "hole chain" (numbering according to the Kabat EU index).

Apart from the "knob-into-hole technology" other techniques for modifying the CH3 domains of the heavy chains of a multispecific antibody to enforce heterodimerization are known in the art. These technologies, especially the ones described in WO 96/27011, WO 98/050431, EP 1870459, WO 2007/110205, WO 2007/147901, WO 2009/089004, WO 2010/129304, WO 2011/90754, WO 2011/143545, WO 2012/058768, WO 2013/157954 and WO 2013/096291 are contemplated herein as alternatives to the "knob-into-hole technology" in combination with a multispecific antibody as reported herein.

In one embodiment of a multispecific antibody as reported herein the approach described in EP 1870459 is used to support heterodimerization of the first heavy chain and the second heavy chain of the multispecific antibody. This approach is based on the introduction of charged amino acids with opposite charges at specific amino acid positions in the CH3/CH3-domain-interface between both, the first and the second heavy chain.

Accordingly, this embodiment relates to a multispecific antibody as reported herein, wherein in the tertiary structure of the antibody the CH3 domain of the first heavy chain and the CH3 domain of the second heavy chain form an interface that is located between the respective antibody CH3 domains, wherein the respective amino acid sequences of the CH3 domain of the first heavy chain and the CH3 domain of the second heavy chain each comprise a set of amino acids that is located within said interface in the tertiary structure of the antibody, wherein from the set of amino acids that is located in the interface in the CH3 domain of one heavy chain a first amino acid is substituted by a positively charged amino acid and from the set of amino acids that is located in the interface in the CH3 domain of the other heavy chain a second amino acid is substituted by a negatively charged amino acid. The multispecific antibody according to this embodiment is herein also referred to as "CH3(+/−)-engineered multispecific antibody" (wherein the abbreviation "+/−" stands for the oppositely charged amino acids that were introduced in the respective CH3 domains).

In one embodiment of said CH3(+/−)-engineered multispecific antibody as reported herein the positively charged amino acid is selected from K, R and H, and the negatively charged amino acid is selected from E or D.

In one embodiment of said CH3(+/−)-engineered multispecific antibody as reported herein the positively charged amino acid is selected from K and R, and the negatively charged amino acid is selected from E or D.

In one embodiment of said CH3(+/−)-engineered multispecific antibody as reported herein the positively charged amino acid is K, and the negatively charged amino acid is E.

In one embodiment of said CH3(+/−)-engineered multispecific antibody as reported herein in the CH3 domain of one heavy chain the amino acid R at position 409 is substituted by D and the amino acid K at position is substituted by E, and in the CH3 domain of the other heavy chain the amino acid D at position 399 is substituted by K and the amino acid E at position 357 is substituted by K (numbering according to Kabat EU index).

In one embodiment of a multispecific antibody as reported herein the approach described in WO 2013/157953 is used to support heterodimerization of the first heavy chain and the second heavy chain of the multispecific antibody. In one embodiment of said multispecific antibody as reported herein, in the CH3 domain of one heavy chain the amino acid T at position 366 is substituted by K, and in the CH3 domain of the other heavy chain the amino acid L at position 351 is substituted by D (numbering according to Kabat EU index). In another embodiment of said multispecific antibody as reported herein, in the CH3 domain of one heavy chain the amino acid T at position 366 is substituted by K and the amino acid L at position 351 is substituted by K, and in the CH3 domain of the other heavy chain the amino acid L at position 351 is substituted by D (numbering according to Kabat EU index).

In another embodiment of said multispecific antibody as reported herein, in the CH3 domain of one heavy chain the amino acid T at position 366 is substituted by K and the amino acid L at position 351 is substituted by K, and in the CH3 domain of the other heavy chain the amino acid L at position 351 is substituted by D (numbering according to Kabat EU index). Additionally at least one of the following substitutions is comprised in the CH3 domain of the other heavy chain: the amino acid Y at position 349 is substituted by E, the amino acid Y at position 349 is substituted by D and the amino acid L at position 368 is substituted by E (numbering according to Kabat EU index). In one embodiment the amino acid L at position 368 is substituted by E (numbering according to Kabat EU index).

In one embodiment of a multispecific antibody as reported herein the approach described in WO 2012/058768 is used to support heterodimerization of the first heavy chain and the second heavy chain of the multispecific antibody. In one embodiment of said multispecific antibody as reported herein, in the CH3 domain of one heavy chain the amino acid L at position 351 is substituted by Y and the amino acid Y at position 407 is substituted by A, and in the CH3 domain of the other heavy chain the amino acid T at position 366 is substituted by A and the amino acid K at position 409 is substituted by F (numbering according to Kabat EU index). In another embodiment, in addition to the aforementioned substitutions, in the CH3 domain of the other heavy chain at least one of the amino acids at positions 411 (originally T), 399 (originally D), 400 (originally S), 405 (originally F), 390 (originally N) and 392 (originally K) is substituted (numbering according to Kabat EU index). Preferred substitutions are:

substituting the amino acid T at position 411 by an amino acid selected from N, R, Q, K, D, E and W (numbering according to Kabat EU index), substituting the amino acid D at position 399 by an amino acid selected from R, W, Y, and K (numbering according to Kabat EU index), substituting the amino acid S at position 400 by an amino acid selected from E, D, R and K (numbering according to Kabat EU index), substituting the amino acid F at position 405 by an amino acid selected from I, M, T, S, V and W (numbering according to Kabat EU index;

substituting the amino acid N at position 390 by an amino acid selected from R, K and D (numbering according to Kabat EU index; and substituting the amino acid K at position 392 by an amino acid selected from V, M, R, L, F and E (numbering according to Kabat EU index).

In another embodiment of said multispecific antibody as reported herein (engineered according to WO 2012/058768), in the CH3 domain of one heavy chain the amino acid L at position 351 is substituted by Y and the amino acid Y at position 407 is substituted by A, and in the CH3 domain of the other heavy chain the amino acid T at position 366 is substituted by V and the amino acid K at position 409 is substituted by F (numbering according to Kabat EU index). In another embodiment of said multispecific antibody as reported herein, in the CH3 domain of one heavy chain the amino acid Y at position 407 is substituted by A, and in the CH3 domain of the other heavy chain the amino acid T at position 366 is substituted by A and the amino acid K at position 409 is substituted by F (numbering according to Kabat EU index). In said last aforementioned embodiment, in the CH3 domain of said other heavy chain the amino acid K at position 392 is substituted by E, the amino acid T at position 411 is substituted by E, the amino acid D at position 399 is substituted by R and the amino acid S at position 400 is substituted by R (numbering according to Kabat EU index).

In one embodiment of a multispecific antibody as reported herein the approach described in WO 2011/143545 is used to support heterodimerization of the first heavy chain and the second heavy chain of the multispecific antibody. In one embodiment of said multispecific antibody as reported herein, amino acid modifications in the CH3 domains of both heavy chains are introduced at positions 368 and/or 409 (numbering according to Kabat EU index).

In one embodiment of a multispecific antibody as reported herein the approach described in WO 2011/090762 is used to support heterodimerization of the first heavy chain and the second heavy chain of the multispecific antibody. WO 2011/090762 relates to amino acid modifications according to the "knob-into-hole" technology. In one embodiment of said CH3(KiH)-engineered multispecific antibody as reported herein, in the CH3 domain of one heavy chain the amino acid T at position 366 is substituted by W, and in the CH3 domain of the other heavy chain the amino acid Y at position 407 is substituted by A (numbering according to Kabat EU index). In another embodiment of said CH3 (KiH)-engineered multispecific antibody as reported herein, in the CH3 domain of one heavy chain the amino acid T at position 366 is substituted by Y, and in the CH3 domain of the other heavy chain the amino acid Y at position 407 is substituted by T (numbering according to Kabat EU index).

In one embodiment of a multispecific antibody as reported herein, which is of IgG2 isotype, the approach described in WO 2011/090762 is used to support heterodimerization of the first heavy chain and the second heavy chain of the multispecific antibody.

In one embodiment of a multispecific antibody as reported herein, the approach described in WO 2009/089004 is used to support heterodimerization of the first heavy chain and the second heavy chain of the multispecific antibody. In one embodiment of said multispecific antibody as reported herein, in the CH3 domain of one heavy chain the amino acid K or N at position 392 is substituted by a negatively charged amino acid (in one preferred embodiment by E or D, in one preferred embodiment by D), and in the CH3 domain of the other heavy chain the amino acid D at position 399 the amino acid E or D at position 356 or the amino acid E at position 357 is substituted by a positively charged amino acid (in one preferred embodiment K or R, in one preferred embodiment by K, in one preferred embodiment the amino acids at positions 399 or 356 are substituted by K) (numbering according to Kabat EU index). In one further embodiment, in addition to the aforementioned substitutions, in the CH3 domain of the one heavy chain the amino acid K or R at position 409 is substituted by a negatively charged amino acid (in one preferred embodiment by E or D, in one preferred embodiment by D) (numbering according to Kabat EU index). In one even further embodiment, in addition to or alternatively to the aforementioned substitutions, in the CH3 domain of the one heavy chain the amino acid K at position 439 and/or the amino acid K at position 370 is substituted independently from each other by a negatively charged amino acid (in one preferred embodiment by E or D, in one preferred embodiment by D) (numbering according to Kabat EU index).

In one embodiment of a multispecific antibody as reported herein, the approach described in WO 2007/147901 is used to support heterodimerization of the first heavy chain and the second heavy chain of the multispecific antibody. In one embodiment of said multispecific antibody as reported herein, in the CH3 domain of one heavy chain the amino acid K at position 253 is substituted by E, the amino acid D at position 282 is substituted by K and the amino acid K at position 322 is substituted by D, and in the CH3 domain of the other heavy chain the amino acid D at position 239 is substituted by K, the amino acid E at position 240 is substituted by K and the amino acid K at position 292 is substituted by D (numbering according to Kabat EU index).

In one embodiment of a multispecific antibody as reported herein, the approach described in WO 2007/110205 is used to support heterodimerization of the first heavy chain and the second heavy chain of the multispecific antibody In one embodiment of all aspects and embodiments as reported herein the multispecific antibody is a bispecific antibody or a trispecific antibody. In one preferred embodiment the multispecific antibody is a bispecific antibody.

In one embodiment of all aspects as reported herein, the antibody is a bivalent or trivalent antibody. In one embodiment the antibody is a bivalent antibody.

In one embodiment of all aspects as reported herein, the multispecific antibody has a constant domain structure of an IgG type antibody. In one further embodiment of all aspects as reported herein, the multispecific antibody is characterized in that said multispecific antibody is of human subclass IgG1, or of human subclass IgG1 with the mutations L234A and L235A. In one further embodiment of all aspects as reported herein, the multispecific antibody is characterized in that said multispecific antibody is of human subclass IgG2. In one further embodiment of all aspects as reported herein, the multispecific antibody is characterized in that said multispecific antibody is of human subclass IgG3. In one further embodiment of all aspects as reported herein, the multispecific antibody is characterized in that said multispecific antibody is of human subclass IgG4 or, of human subclass IgG4 with the additional mutation S228P. In one further embodiment of all aspects as reported herein, the multispecific antibody is characterized in that said multispecific antibody is of human subclass IgG1 or human subclass IgG4. In one further embodiment of all aspects as reported herein, the multispecific antibody is characterized in that said multispecific antibody is of human subclass IgG1 with the mutations L234A and L235A (numbering according to Kabat EU index). In one further embodiment of all aspects as reported herein, the multispecific antibody is characterized in that said multispecific antibody is of human subclass IgG1 with the mutations L234A, L235A and P329G (numbering according to Kabat EU index). In one further embodiment of all aspects as reported herein, the multispecific antibody is characterized in that said multispecific antibody is of human subclass IgG4 with the mutations S228P and L235E (numbering according to Kabat EU index). In one further embodiment of all aspects as reported herein, the multispecific antibody is characterized in that said multispecific antibody is of human subclass IgG4 with the mutations S228P, L235E and P329G (numbering according to Kabat EU index).

In one embodiment of all aspects as reported herein, an antibody comprising a heavy chain including a CH3 domain as specified herein, comprises an additional C-terminal glycine-lysine dipeptide (G446 and K447, numbering according to Kabat EU index). In one embodiment of all aspects as reported herein, an antibody comprising a heavy chain including a CH3 domain, as specified herein, comprises an additional C-terminal glycine residue (G446, numbering according to Kabat EU index).

The antibody as reported herein is in one embodiment characterized by being of human subclass IgG1 with mutations PVA236, L234A/L235A, and/or GLPSS331 (numbering according to EU index of Kabat), or of subclass IgG4. In a further embodiment, the antibody is characterized by being of any IgG class, in one embodiment being IgG1 or IgG4, containing at least one mutation in E233, L234, L235, G236, D270, N297, E318, K320, K322, A327, A330, P331 and/or P329 (numbering according to EU index of Kabat). It is further in one embodiment that the antibody of IgG4 subclass contains the mutation S228P, or the mutations S228P and L235E (Angal, S., et al., Mol. Immunol. 30 (1993) 105-108) (numbering according to EU index of Kabat).

The C-terminus of the heavy chain of the antibody as reported herein can be a complete C-terminus ending with the amino acid residues PGK. The C-terminus of the heavy chain can be a shortened C-terminus in which one or two of the C-terminal amino acid residues have been removed. In one preferred embodiment the C-terminus of the heavy chain is a shortened C-terminus ending PG.

In certain embodiments, an antibody provided herein may be further modified to contain one or more blood-brain-barrier shuttle modules that are known in the art and readily available.

The blood-brain-barrier shuttle module is characterized by having a binding specificity for a blood-brain-barrier receptor. This binding specificity can be obtained either by fusing a blood-brain-barrier shuttle module to the anti-human CD19 antibody as reported herein or it can be obtained by introducing the binding specificity to the bloodbrain-barrier receptor as one of the binding specificities of a multispecific antibody that specifically binds to human CD19 and, thus, comprises the binding specificity of the anti-human CD19 antibody as reported herein and the binding specificity to the blood-brain-barrier receptor.

One or more blood-brain-barrier shuttle modules can be fused to any terminus of the light or heavy chain of the anti-human CD19 antibody as reported herein. In one preferred embodiment the blood-brain-barrier shuttle module is fused to the C-terminus of the heavy chain.

The one or more blood-brain-barrier shuttle modules can be fused to the respective antibody chain either directly or via linker peptide. In one preferred embodiment the linker peptide has the amino acid sequence GGSGGGGSGGGGSGGGGS (SEQ ID NO: 41).

The blood-brain-barrier shuttle module can be an antibody scFv fragment. In one embodiment the blood-brain-barrier shuttle module is a scFv comprising in N- to C-terminal order a light chain variable domain—a light chain constant domain—a linker peptide—a heavy chain variable domain—the heavy chain constant domain1.

In one preferred embodiment the blood-brain-barrier shuttle module is the scFv fragment of the anti-transferrin receptor-antibody 8D3 with a $(G4S)_6$ linker peptide or a humanized variant thereof The term humanized variant thereof denotes a molecule that has been obtained by grafting the CDRs of the murine 8D3 antibody on a human framework with the optional introduction of one to three mutations independently of each other in each of the framework regions (FRs) and/or the hypervariable regions (HVRs).

In one aspect, herein is provided an anti-human CD19 antibody fusion polypeptide comprising an anti-human CD19 antibody, two peptide linker and two monovalent binding entities which bind to a blood-brain-barrier receptor, wherein the linker couples the anti-human CD19 antibody to the monovalent binding entities which bind to the blood-brain-barrier receptor.

In one aspect, herein is provided an anti-human CD19 antibody fusion polypeptide comprising an anti-human CD19 antibody, a peptide linker and one monovalent binding entity which binds to a blood-brain-barrier receptor, wherein the linker couples the anti-human CD19 antibody to the monovalent binding entity which bind to the blood-brain-barrier receptor.

In one embodiment, the monovalent binding entity which binds to the blood-brain-barrier receptor is selected from the group consisting of proteins, polypeptides and peptides.

In one embodiment, the monovalent binding entity which binds to the blood-brain-barrier receptor comprises a molecule selected from the group consisting of a blood-brain-barrier receptor ligand, a scFv, an Fv, a scFab, a VHH, in one preferred embodiment a scFv or a scFab.

In one embodiment, the blood-brain-barrier receptor is selected from the group consisting of transferrin receptor, insulin receptor, insulin-like growth factor receptor, low density lipoprotein receptor-related protein 8, low density lipoprotein receptor-related protein 1 and heparin-binding epidermal growth factor-like growth factor. In one preferred embodiment the blood-brain-barrier receptor is the transferrin receptor.

In one embodiment, the monovalent binding entity which binds to the blood-brain-barrier receptor comprises one scFab or one scFv directed to the transferrin receptor, more particular a scFab or scFv recognizing an epitope in the transferrin receptor comprised within the amino acid sequence of SEQ ID NO: 42, 43 and 44.

In one embodiment, the monovalent binding entity which binds to the blood-brain-barrier receptor is coupled to the C-terminal end of the heavy chain of the anti-human CD19 antibody by the linker.

In one embodiment, the peptide linker is an amino acid sequence with a length of at least 15 amino acids, more preferably with a length of 18 to 25 amino acids.

In one embodiment, the anti-human CD19 antibody is a full length antibody, in one preferred embodiment a full length IgG. The term full length antibody denotes an antibody consisting of two antibody light chain polypeptides and two antibody heavy chain polypeptides wherein in the two antibody heavy chain polypeptides the C-terminal lysine residue (K) can be present or not.

In one preferred embodiment, the anti-human CD19 antibody fusion polypeptide comprises a full length IgG anti-human CD19 antibody as brain effector entity, a linker of the sequence GGSGGGGSGGGGSGGGGS (SEQ ID NO: 41) and one scFab as monovalent binding entity which binds to the human transferrin receptor as blood brain receptor, wherein the scFab is coupled by the linker to the C-terminal end (of the Fc part) of one of the heavy chains of the full length anti-human CD19 antibody, and wherein the scFab recognizes an epitope in the human transferrin receptor comprised within the amino acid sequence of SEQ ID NO: 52, 53 and 54.

In one preferred embodiment, the anti-human CD19 antibody fusion polypeptide comprises a full length IgG anti-human CD19 antibody as brain effector entity, a linker of the sequence GGSGGGGSGGGGSGGGGS (SEQ ID NO: 41) and one scFv as monovalent binding entity which binds to the human transferrin receptor as blood brain receptor, wherein the scFab is coupled by the linker to the C-terminal end (of the Fc part) of one of the heavy chains of the full length anti-human CD19 antibody, and wherein the scFab recognizes an epitope in the human transferrin receptor comprised within the amino acid sequence of SEQ ID NO: 42, 43 and 44.

In one embodiment, the first heavy chain of the anti-human CD19 antibody comprises a first dimerization module and the second heavy chain of the antibody comprises a second dimerization module allowing heterodimerization of the two heavy chains.

In one embodiment, the first dimerization module of the first heavy chain of the anti-human CD19 antibody is a knob heavy chain and the dimerization module of the second heavy chain of the anti-human CD19 antibody is a hole heavy chain (according to the knobs-into-holes strategy).

The anti-human CD19 antibody fusion polypeptide as reported herein can be used to transport the anti-human CD19 antibody across the blood brain barrier.

In one embodiment, the heavy chain of the anti-human CD19 antibody that is coupled at its C-terminal end of the Fc-region to the scFab as monovalent binding entity which binds to the human transferrin receptor has the following structure in N- to C-terminal direction:

IgG heavy chain,
peptidic linker coupling the C-terminal end of the Fc-region of the IgG heavy chain to the N-terminal end of the VL domain of the scFab, in one preferred embodiment the peptidic linker has the amino acid sequence GGSGGGGSGGGGSGGGGS (SEQ ID NO: 41),
variable light chain domain (VL) and C-kappa light chain domain of the scFab,
peptidic linker coupling the C-terminal end of the C-kappa light chain domain of the scFab to the N-terminal end of the VH domain of the scFab, in one preferred embodiment the peptidic linker has the amino acid sequence (G$_4$S)$_6$GG (SEQ ID NO: 45),
variable heavy chain domain (VH) of the scFab antibody and IgG CH1 heavy chain domain.

In one embodiment, the heavy chain of the anti-human CD19 antibody that is coupled at its C-terminal end of the Fc-region to the scFv as monovalent binding entity which binds to the human transferrin receptor has the following structure in N- to C-terminal direction:
IgG heavy chain,
peptidic linker coupling the C-terminal end of the Fc part of the IgG heavy chain to the N-terminal end of the VL domain of the scFv antibody fragment, in one preferred embodiment the peptidic linker is a peptide with the amino acid sequence GGSGGGGSGGGGSGGGGS (SEQ ID NO: 41),
variable light chain domain (VL),
peptidic linker coupling the C-terminal end of the variable light chain domain to the N-terminal end of the VH domain of the scFv, in one preferred embodiment the peptidic linker is a peptide with the amino acid sequence (G$_4$S)$_6$GG (SEQ ID NO: 45),
variable heavy chain domain (VH) of the scFv antibody fragment.

In one embodiment the blood-brain-barrier shuttle module/the scFab or scFv directed to a blood-brain-barrier receptor is derived from a humanized anti-transferrin receptor antibody 8D3 (see e.g. Boado, R. J., et al., Biotechnol. Bioeng. 102 (2009) 1251-1258). The murine heavy chain variable domain has the amino acid sequence of

```
                                        (SEQ ID NO: 46)
EVQLVESGGG LVQPGNSLTL SCVASGFTFS NYGMHWIRQA
PKKGLEWIAM IYYDSSKMNY ADTVKGRFTI SRDNSKNTLY
LEMNSLRSED TAMYYCAVPT SHYVVDVWGQ GVSVTVSS.
```

The murine light chain variable domain (variant 1) has the amino acid sequence of

```
                                        (SEQ ID NO: 47)
DIQMTQSPAS LSASLEEIVT ITCQASQDIG NWLAWYQQKP
GKSPQLLIYG ATSLADGVPS RFSGSRSGTQ FSLKISRVQV
EDIGIYYCLQ AYNTPWTFGG GTKLELK,
``` and the murine light chain variable domain (variant 2) has the amino acid sequence of

```
                                        (SEQ ID NO: 48)
DIQMTQSPAS LSASLEEIVT ITCQASQDIG NWLAWYQQKP
GKSPQLLIYG ATSLADGVPS RFSGSRSGTQ FSLKISRVQV
EDIGIYYCLQ AYNTPWTFGG GTKVEIK.
```

In one embodiment the anti-transferrin receptor antibody or transferrin receptor binding specificity comprises (a) a HVR-H1 comprising the amino acid sequence of SEQ ID NO: 51; (b) a HVR-H2 comprising the amino acid sequence of SEQ ID NO: 52; (c) a HVR-H3 comprising the amino acid sequence of SEQ ID NO: 53, 54 or 55; (d) a HVR-L1 comprising the amino acid sequence of SEQ ID NO: 56; (e) a HVR-L2 comprising the amino acid sequence of SEQ ID NO: 57; and (f) a HVR-L3 comprising the amino acid sequence of SEQ ID NO: 58.

In one embodiment the anti-transferrin receptor antibody comprises at least one pair of the heavy chain variable domain of SEQ ID NO: 49 and the light chain variable domain of SEQ ID NO: 50 forming a binding site for the transferrin receptor.

One Blood-Brain-Barrier Shuttle Module

In one aspect the anti-human CD19 antibody or anti-human CD19 antibody fusion polypeptide comprises exactly one blood-brain-barrier binding specificity or shuttle module, thus is at least bispecific, wherein the blood-brain-barrier binding specificity or shuttle module comprises the humanized variable domains of the anti-human transferrin receptor antibody 8D3 or the pair of the heavy chain variable domain of SEQ ID NO: 49 and the light chain variable domain of SEQ ID NO: 50, whereby the blood-brain-barrier binding specificity or shuttle module transports the anti-human CD19 antibody across the blood-brain-barrier One or Two Blood-Brain-Barrier Shuttle Modules In one aspect the anti-human CD19 antibody or anti-human CD19 antibody fusion polypeptide comprises one or two blood-brain-barrier binding specificities or shuttle module(s), thus is at least bispecific, wherein the blood-brain-barrier shuttle binding site or module is/are derived from an antibody which binds with low affinity to a blood-brain-barrier receptor (BBB-R, BBB-R binding specificity), whereby the blood-brain-barrier binding specificity or shuttle module derived from an antibody which binds with low affinity to a blood-brain-barrier receptor transports the anti-human CD19 antibody across the blood-brain-barrier.

In one embodiment, the BBB-R is selected from the group consisting of transferrin receptor (TfR), insulin receptor, insulin-like growth factor receptor (IGF receptor), low density lipoprotein receptor-related protein 8 (LRP8), low density lipoprotein receptor-related protein 1 (LRP1), and heparin-binding epidermal growth factor-like growth factor (HB-EGF). In another such aspect, the BBB-R is a human BBB-R. In one such aspect, the BBB-R is TfR. In another such aspect, the BBB-R is TfR and the antibody does not inhibit TfR activity. In another such aspect, the BBB-R is TfR and the antibody does not inhibit the binding of TfR to transferrin.

In one embodiment, the antibody does not impair the binding of the BBB-R to one or more of its native ligands. In one such embodiment, the antibody specifically binds to human transferrin receptor (hTfR) in such a manner that it does not inhibit binding of the hTfR to human transferrin.

In one embodiment, the BBB-R binding specificity has an IC$_{50}$ for the BBB-R from about 1 nM to about 100 μM. In one embodiment, the IC$_{50}$ is from about 5 nM to about 100 μM. In one embodiment, the IC$_{50}$ is from about 50 nM to about 100 μM. In one embodiment, the IC$_{50}$ is from about 100 nM to about 100 μM. In one embodiment, the BBB-R binding specificity has an affinity for the BBB-R from about 5 nM to about 10 μM. In one embodiment, the BBB-R binding specificity, when conjugated to or comprised in the anti-human CD19, has an affinity for the BBB-R from about 30 nM to about 1 μM. In one embodiment, the BBB-R binding specificity, when conjugated to or comprised in the anti-human CD19 antibody, has an affinity for the BBB-R from about 50 nM to about 1 μM. In one embodiment, the affinity of the BBB-R binding specificity or the anti-human CD19 antibody fusion polypeptide for the BBB-R is measured using scatchard analysis. In one embodiment, the affinity of the BBB-R binding specificity or the anti-human CD19 antibody fusion polypeptide for the BBB-R is measured using BIACORE analysis. In one embodiment, the affinity of the BBB-R binding specificity or the anti-human CD19 antibody fusion polypeptide for the BBB-R is measured using a competition ELISA.

Use of the Blood-Brain-Barrier Shuttle Containing Antibody Fusion Polypeptides

In another embodiment, herein is provided a method of increasing exposure of the CNS to an anti-human CD19 antibody, wherein the anti-human CD19 antibody is coupled to an antibody or antibody fragment which binds with low affinity to a BBB-R, thereby increasing the exposure of the CNS to the anti-human CD19 antibody. The term "coupled" includes cases wherein the anti-BBB-R antibody binding specificity is introduced as second binding specificity in an at least bispecific anti-human CD19/BBB-R antibody. In one embodiment, the increase in CNS exposure to the anti-human CD19 antibody is measured relative to the CNS exposure of an anti-human CD19 antibody coupled with a typical antibody not having lowered affinity for the BBB-R. In one embodiment, the increase in CNS exposure to the anti-human CD19 antibody is measured as a ratio of the amount of the anti-human CD19 antibody found in the CNS relative to the amount found in the serum after administration. In one embodiment, the increase in CNS exposure results in a ratio of greater than 0.1%. In one embodiment, the increase in CNS exposure to the anti-human CD19 antibody is measured relative to the CNS exposure of the anti-human CD19 antibody in the absence of a coupled anti-BBB-R antibody. In one embodiment, the increase in CNS exposure to the anti-human CD19 antibody is measured by imaging. In one embodiment, the increase in CNS exposure to the anti-human CD19 antibody is measured by an indirect readout such as a modification of one or more physiological symptoms.

A method of increasing retention in the CNS of an anti-human CD19 antibody administered to a subject, wherein the anti-human CD19 antibody is coupled to an antibody or antibody fragment, which binds with low affinity to a BBB-R, such that the retention in the CNS of the anti-human CD19 antibody is increased.

In another embodiment, herein is provided a method of optimizing the pharmacokinetics and/or pharmacodynamics of an anti-human CD19 antibody to be efficacious in the CNS of a subject, wherein the anti-human CD19 antibody is coupled to an antibody or antibody fragment, which binds with low affinity to a BBB-R, whereby the antibody or antibody fragment is selected such that its affinity for the BBB-R after coupling to the anti-human CD19 antibody results in an amount of transport of the antibody or antibody fragment conjugated to the anti-human CD19 antibody across the BBB that optimizes the pharmacokinetics and/or pharmacodynamics of the anti-human CD19 antibody in the CNS.

In another embodiment herein is provided a method of treating a neurological disorder in a mammal comprising treating the mammal with an antibody or antibody fragment, which binds a BBB-R and which is coupled to an anti-human CD19 antibody, wherein the antibody has been selected to have a low affinity for the BBB-R and thereby improves CNS uptake of the antibody and coupled anti-human CD19 antibody. In one embodiment, the treating results in lessening or elimination of disorder symptoms. In another aspect, the treating results in amelioration of the neurological disorder.

In one embodiment of all previous aspects, the anti-BBB-R antibody has an $IC_{50}$ for the BBB-R from about 1 nM to about 100 µM. In another such embodiment, the $IC_{50}$ is from about 5 nM to about 100 µM. In another such embodiment, the $IC_{50}$ is from about 50 nM to about 100 µM. In another such embodiment, the $IC_{50}$ is from about 100 nM to about 100 µM. In another embodiment, the antibody has an affinity for the BBB-R from about 5 nM to about 10 µM. In another embodiment, the antibody, when coupled to the anti-human CD19 antibody, has an affinity for the BBB-R from about 30 nM to about 1 µM. In another embodiment, the antibody, when coupled to the anti-human CD19 antibody, has an affinity for the BBB-R from about 50 nM to about 1 µM. In one embodiment, the affinity of the anti-BBB-R antibody or the anti-human CD19 antibody fusion polypeptide for the BBB-R is measured using scatchard analysis. In another embodiment, the affinity of the anti-BBB-R antibody or the anti-human CD19 antibody fusion polypeptide for the BBB-R is measured using BIACORE analysis. In another embodiment, the affinity of the anti-BBB-R antibody or the anti-human CD19 antibody fusion polypeptide for the BBB-R is measured using a competition ELISA.

In another embodiment, the anti-human CD19 antibody fusion polypeptide is labeled. In another embodiment, the anti-BBB-R antibody or fragment does not impair the binding of the BBB-R to one or more of its native ligands. In another embodiment, the anti-BBB-R antibody specifically binds to hTfR in such a manner that it does not inhibit binding of the hTfR to human transferrin. In another embodiment, the anti-human CD19 antibody fusion polypeptide is administered to a mammal. In another embodiment, the mammal is a human. In another embodiment, the mammal has a neurological disorder. In another embodiment, the neurological disorder is selected from the group consisting of Alzheimer's disease (AD), stroke, dementia, muscular dystrophy (MD), multiple sclerosis (MS), amyotrophic lateral sclerosis (ALS), cystic fibrosis, Angelman's syndrome, Liddle syndrome, Parkinson's disease, Pick's disease, Paget's disease, cancer, and traumatic brain injury.

Non-Covalent Complexes as Blood-Brain Barrier Shuttles

One part of the non-covalent complex is a blood brain barrier-shuttle module (BBB-shuttle module) that is a bispecific antibody with a first binding specificity for a hapten and a second binding specificity for a blood-brain-barrier receptor (BBBR). Such a BBB-shuttle module recognizes a transcytoseable cell surface target on the blood brain barrier (such as TfR, LRPs or other targets, BBB-R) and simultaneously binds to a haptenylated anti-human CD19 antibody.

In more detail, the antibody that specifically binds to human CD19 is conjugated with a hapten and complexed by the hapten-binding site of the blood brain barrier shuttle. This complex is defined and stable and specifically delivers the haptenylated antibody that specifically binds to human CD19 over the blood brain barrier. Since the haptenylated antibody that specifically binds to human CD19 is complexed in a non-covalent manner by the blood-brain-barrier shuttle, the haptenylated antibody that specifically binds to human CD19 is on the one hand bound to its delivery vehicle (=blood-brain-barrier shuttle=bispecific antibody) during its time in the circulation but can also on the other hand be efficiently released after transcytosis. The conjugation with the hapten can be effected without interfering with the activity of the antibody that specifically binds to human CD19. The blood-brain-barrier shuttle does not contain an unusual covalent addition and therefore obviates any risk of immunogenicity. Complexes of haptenylated antibody that specifically binds to human CD19 with the bispecific antibody containing the hapten-specific binding sites confer benign biophysical behavior to the antibody that specifically binds to human CD19. Furthermore, such complexes are capable to target the load to cells or tissues which display the antigen that is recognized by the bispecific antibody's second binding specificity.

The antibody that specifically binds to human CD19 retains its functionality despite being haptenylated, as well as while being complexed by the blood-brain-barrier shuttle (=bispecific antibody). In addition, the blood-brain-barrier receptor binding site of the bispecific antibody retains its binding specificity and affinity in the presence of complexed haptenylated antibody that specifically binds to human CD19. The complexes of haptenylated antibody that specifically binds to human CD19 with the bispecific antibody as reported herein can be used to target the antibody that specifically binds to human CD19 specifically to cells that express the blood-brain-barrier receptor. Since the haptenylated antibody that specifically binds to human CD19 is coupled in a non-covalent manner to the bispecific antibody the antibody that specifically binds to human CD19 can be released after internalization or transcytosis.

In a further aspect, an anti-human CD19 antibody according to any of the above embodiments may incorporate any of the features, singly or in combination, as described in Sections 1-5 below:

1. Antibody Affinity

In certain embodiments, an antibody provided herein has a $K_D$ value of ≤1 μM, ≤100 nM, or ≤10 nM (e.g. $10^{-8}$M or less, e.g. from $10^{-7}$M to $10^{-8}$M).

For example, $K_D$ can be measured using a BIACORE® surface plasmon resonance assay. An assay using a BIACORE®-2000 or a BIACORE®-3000 (BIAcore, Inc., Piscataway, N.J.) is performed at 25° C. with immobilized antigen CM5 chips at −10 response units (RU). The carboxymethylated dextran biosensor chips (CM5, BIACORE, Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, to 5 μg/ml (~0.2 μM) before injection at a flow rate of 5 μl/minute to achieve approximately 10 response units (RU) of coupled protein. Following the injection of antigen, 1 M ethanolamine is injected to block unreacted groups. For kinetics measurements, two-fold serial dilutions of Fab (0.78 nM to 500 nM) are injected in PBS with 0.05% polysorbate 20 (TWEEN-20™) surfactant (PBST) at 25° C. at a flow rate of approximately 25 μl/min. Association rates ($k_{on}$) and dissociation rates ($k_{off}$) are calculated using a simple one-to-one Langmuir binding model (BIACORE® Evaluation Software version 3.2) by simultaneously fitting the association and dissociation sensorgrams. The equilibrium dissociation constant ($K_D$) is calculated as the ratio $k_{off}/k_{on}$ (see, e.g., Chen, Y. et al., J. Mol. Biol. 293 (1999) 865-881).

2. Antibody Fragments

In certain embodiments, an antibody provided herein is an antibody fragment. Antibody fragments include, but are not limited to, Fab, Fab', Fab'-SH, $F(ab')_2$, Fv, and scFv fragments, and other fragments described below. For a review of certain antibody fragments, see Hudson, P. J. et al., Nat. Med. 9 (2003) 129-134. For a review of scFv fragments, see, e.g., Plueckthun, A., In; The Pharmacology of Monoclonal Antibodies, Vol. 113, Rosenburg and Moore (eds.), Springer-Verlag, New York (1994), pp. 269-315; see also WO 93/16185; U.S. Pat. Nos. 5,571,894 and 5,587,458. For discussion of Fab and $F(ab)_2$ fragments comprising salvage receptor binding epitope residues and having increased in vivo half-life, see U.S. Pat. No. 5,869,046.

Diabodies are antibody fragments with two antigen-binding sites that may be bivalent or bispecific. See, for example, EP 0 404 097; WO 1993/01161; Hudson, P. J. et al., Nat. Med. 9 (2003) 129-134; and Holliger, P. et al., Proc. Natl. Acad. Sci. USA 90 (1993) 6444-6448. Triabodies and tetrabodies are also described in Hudson, P. J. et al., Nat. Med. 9 (20039 129-134).

Single-domain antibodies are antibody fragments comprising all or a portion of the heavy chain variable domain or all or a portion of the light chain variable domain of an antibody. In certain embodiments, a single-domain antibody is a human single-domain antibody (Domantis, Inc., Waltham, Mass.; see, e.g., U.S. Pat. No. 6,248,516).

Antibody fragments can be made by various techniques, including but not limited to proteolytic digestion of an intact antibody as well as production by recombinant host cells (e.g. *E. coli* or phage), as described herein.

3. Chimeric and Humanized Antibodies

An antibody provided herein is a chimeric antibody. Certain chimeric antibodies are described, e.g., in U.S. Pat. No. 4,816,567; and Morrison, S. L. et al., Proc. Natl. Acad. Sci. USA 81 (1984) 6851-6855). In one example, a chimeric antibody comprises a non-human variable region (e.g., a variable region derived from a mouse, rat, hamster, rabbit, or non-human primate, such as a monkey) and a human constant region. In a further example, a chimeric antibody is a "class switched" antibody in which the class or subclass has been changed from that of the parent antibody. Chimeric antibodies include antigen-binding fragments thereof.

A humanized antibody is a chimeric antibody is. Typically, a non-human antibody is humanized to reduce immunogenicity to humans, while retaining the specificity and affinity of the parental non-human antibody. Generally, a humanized antibody comprises one or more variable domains in which HVRs, e.g., CDRs, (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the HVR residues are derived), e.g., to restore or improve antibody specificity or affinity.

Humanized antibodies and methods of making them are reviewed, e.g., in Almagro, J. C. and Fransson, J., Front. Biosci. 13 (2008) 1619-1633, and are further described, e.g., in Riechmann, I. et al., Nature 332 (1988) 323-329; Queen, C. et al., Proc. Natl. Acad. Sci. USA 86 (1989) 10029-10033; U.S. Pat. Nos. 5,821,337, 7,527,791, 6,982,321, and 7,087,409; Kashmiri, S. V. et al., Methods 36 (2005) 25-34 (describing specificity determining region (SDR) grafting); Padlan, E. A., Mol. Immunol. 28 (1991) 489-498 (describing "resurfacing"); Dall'Acqua, W. F. et al., Methods 36 (2005) 43-60 (describing "FR shuffling"); and Osbourn, J. et al., Methods 36 (2005) 61-68 and Klimka, A. et al., Br. J. Cancer 83 (2000) 252-260 (describing the "guided selection" approach to FR shuffling).

Human framework regions that may be used for humanization include but are not limited to: framework regions selected using the "best-fit" method (see, e.g., Sims, M. J. et al., J. Immunol. 151 (1993) 2296-2308; framework regions derived from the consensus sequence of human antibodies of a particular subgroup of light or heavy chain variable regions (see, e.g., Carter, P. et al., Proc. Natl. Acad. Sci. USA 89 (1992) 4285-4289; and Presta, L. G. et al., J. Immunol. 151 (1993) 2623-2632); human mature (somatically mutated) framework regions or human germline framework regions (see, e.g., Almagro, J. C. and Fransson, J., Front. Biosci. 13 (2008) 1619-1633); and framework regions derived from screening FR libraries (see, e.g., Baca, M. et al., J. Biol. Chem. 272 (1997) 10678-10684 and Rosok, M. J. et al., J. Biol. Chem. 271 (19969 22611-22618).

4. Multispecific Antibodies

In certain embodiments, an antibody provided herein is a multispecific antibody, e.g. a bispecific antibody. Multispecific antibodies are monoclonal antibodies that have binding specificities for at least two different sites. In certain embodiments, one of the binding specificities is for human CD19 and the other is for any other antigen. In certain embodiments, bispecific antibodies may bind to two different epitopes of human CD19. Bispecific antibodies may also be used to localize cytotoxic agents to cells which express human CD19. Bispecific antibodies can be prepared as full length antibodies or antibody fragments.

Techniques for making multispecific antibodies include, but are not limited to, recombinant co-expression of two immunoglobulin heavy chain-light chain pairs having different specificities (see Milstein, C. and Cuello, A. C., Nature 305 (1983) 537-540, WO 93/08829, and Traunecker, A. et al., EMBO J. 10 (1991) 3655-3659), and "knob-in-hole" engineering (see, e.g., U.S. Pat. No. 5,731,168). Multispecific antibodies may also be made by engineering electrostatic steering effects for making antibody Fc-heterodimeric molecules (WO 2009/089004); cross-linking two or more antibodies or fragments (see, e.g., U.S. Pat. No. 4,676,980, and Brennan, M. et al., Science 229 (1985) 81-83); using leucine zippers to produce bi-specific antibodies (see, e.g., Kostelny, S. A. et al., J. Immunol. 148 (1992) 1547-1553; using "diabody" technology for making bispecific antibody fragments (see, e.g., Holliger, P. et al., Proc. Natl. Acad. Sci. USA 90 (1993) 6444-6448); and using single-chain Fv (sFv) dimers (see, e.g. Gruber, M et al., J. Immunol. 152 (1994) 5368-5374); and preparing trispecific antibodies as described, e.g., in Tutt, A. et al., J. Immunol. 147 (1991) 60-69).

Engineered antibodies with three or more functional antigen binding sites, including "Octopus antibodies," are also included herein (see, e.g. US 2006/0025576).

The antibody or fragment herein also includes a "Dual Acting Fab" or "DAF" comprising an antigen binding site that binds to human CD19 as well as another, different antigen (see, US 2008/0069820, for example).

The antibody or fragment herein also includes multispecific antibodies described in
WO 2009/080251, WO 2009/080252, WO 2009/080253, WO 2009/080254, WO 2010/112193, WO 2010/115589, WO 2010/136172, WO 2010/145792, and WO 2010/145793.

5. Antibody Variants

In certain embodiments, amino acid sequence variants of the antibodies provided herein are contemplated. For example, it may be desirable to improve the binding affinity and/or other biological properties of the antibody. Amino acid sequence variants of an antibody may be prepared by introducing appropriate modifications into the nucleotide sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, e.g., antigen-binding.

a) Substitution, Insertion, and Deletion Variants

In certain embodiments, antibody variants having one or more amino acid substitutions are provided. Sites of interest for substitutional mutagenesis include the HVRs and FRs. Conservative substitutions are shown in the Table below under the heading of "preferred substitutions". More substantial changes are provided in Table 1 under the heading of "exemplary substitutions," and as further described below in reference to amino acid side chain classes. Amino acid substitutions may be introduced into an antibody of interest and the products screened for a desired activity, e.g., retained/improved antigen binding, decreased immunogenicity, or improved ADCC or CDC.

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped according to common side-chain properties:
(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Tip, Tyr, Phe.

Non-conservative substitutions will entail exchanging a member of one of these classes for another class.

One type of substitutional variant involves substituting one or more hypervariable region residues of a parent antibody (e.g. a humanized or human antibody). Generally, the resulting variant(s) selected for further study will have modifications (e.g., improvements) in certain biological properties (e.g., increased affinity, reduced immunogenicity) relative to the parent antibody and/or will have substantially retained certain biological properties of the parent antibody. An exemplary substitutional variant is an affinity matured antibody, which may be conveniently generated, e.g., using phage display-based affinity maturation techniques such as those described herein. Briefly, one or more HVR residues are mutated and the variant antibodies displayed on phage and screened for a particular biological activity (e.g. binding affinity).

Alterations (e.g., substitutions) may be made in HVRs, e.g., to improve antibody affinity. Such alterations may be made in HVR "hotspots," i.e., residues encoded by codons that undergo mutation at high frequency during the somatic maturation process (see, e.g., Chowdhury, P. S., Methods Mol. Biol. 207 (2008) 179-196), and/or residues that contact antigen, with the resulting variant VH or VL being tested for binding affinity. Affinity maturation by constructing and reselecting from secondary libraries has been described, e.g., in Hoogenboom, H. R. et al. in Methods in Molecular Biology 178 (2002) 1-37. In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves HVR-directed approaches, in which several HVR residues (e.g., 4-6 residues at a time) are randomized. HVR residues involved in antigen binding may be specifically identified, e.g., using alanine scanning mutagenesis or modeling. CDR-H3 and CDR-L3 in particular are often targeted.

In certain embodiments, substitutions, insertions, or deletions may occur within one or more HVRs so long as such alterations do not substantially reduce the ability of the antibody to bind antigen. For example, conservative alterations (e.g., conservative substitutions as provided herein) that do not substantially reduce binding affinity may be made in HVRs. Such alterations may, for example, be outside of antigen contacting residues in the HVRs. In certain embodiments of the variant VH and VL sequences provided above, each HVR either is unaltered, or contains no more than one, two or three amino acid substitutions.

A useful method for identification of residues or regions of an antibody that may be targeted for mutagenesis is called "alanine scanning mutagenesis" as described by Cunningham, B. C. and Wells, J. A., Science 244 (1989) 1081-1085. In this method, a residue or group of target residues (e.g., charged residues such as arg, asp, his, lys, and glu) are identified and replaced by a neutral or negatively charged amino acid (e.g., alanine or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antibody complex to identify contact points between the antibody and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g. for ADEPT) or a polypeptide which increases the serum half-life of the antibody.

b) Glycosylation Variants

In certain embodiments, an antibody provided herein is altered to increase or decrease the extent to which the antibody is glycosylated. Addition or deletion of glycosylation sites to an antibody may be conveniently accomplished by altering the amino acid sequence such that one or more glycosylation sites is created or removed.

Where the antibody comprises an Fc region, the carbohydrate attached thereto may be altered. Native antibodies produced by mammalian cells typically comprise a branched, biantennary oligosaccharide that is generally attached by an N-linkage to Asn297 of the CH2 domain of the Fc region. See, e.g., Wright, A. and Morrison, S. L., TIBTECH 15 (1997) 26-32. The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an antibody as reported herein may be made in order to create antibody variants with certain improved properties.

In one embodiment, antibody variants are provided having a carbohydrate structure that lacks fucose attached (directly or indirectly) to an Fc region. For example, the amount of fucose in such antibody may be from 1% to 80%, from 1% to 65%, from 5% to 65% or from 20% to 40%. The amount of fucose is determined by calculating the average amount of fucose within the sugar chain at Asn297, relative to the sum of all glycostructures attached to Asn 297 (e. g. complex, hybrid and high mannose structures) as measured by MALDI-TOF mass spectrometry, as described in WO 2008/077546, for example. Asn297 refers to the asparagine residue located at about position 297 in the Fc region (EU numbering of Fc-region residues according to Kabat); however, Asn297 may also be located about ±3 amino acids upstream or downstream of position 297, i.e., between positions 294 and 300, due to minor sequence variations in antibodies. Such fucosylation variants may have improved ADCC function. See, e.g., US 2003/0157108; US 2004/0093621. Examples of publications related to "defucosylated" or "fucose-deficient" antibody variants include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO 2005/053742; WO 2002/031140; Okazaki, A. et al., J. Mol. Biol. 336 (2004) 1239-1249; Yamane-Ohnuki, N. et al., Biotech. Bioeng. 87 (2004) 614-622. Examples of cell lines capable of producing defucosylated antibodies include Lec13 CHO cells deficient in protein fucosylation (Ripka, J. et al., Arch. Biochem. Biophys. 249 (1986) 533-545; US 2003/0157108; and WO 2004/056312, especially at Example 11), and knockout cell lines, such as alpha-1,6-fucosyltransferase gene, FUT8, knockout CHO cells (see, e.g., Yamane-Ohnuki, N. et al., Biotech. Bioeng. 87 (2004) 614-622; Kanda, Y. et al., Biotechnol. Bioeng. 94 (2006) 680-688; and WO 2003/085107).

Antibodies variants are further provided with bisected oligosaccharides, e.g., in which a biantennary oligosaccharide attached to the Fc region of the antibody is bisected by GlcNAc. Such antibody variants may have reduced fucosylation and/or improved ADCC function. Examples of such antibody variants are described, e.g., in WO 2003/011878; U.S. Pat. No. 6,602,684; and US 2005/0123546. Antibody variants with at least one galactose residue in the oligosaccharide attached to the Fc region are also provided. Such antibody variants may have improved CDC function. Such antibody variants are described, e.g., in WO 1997/30087; WO 1998/58964; and WO 1999/22764.

c) Fc-Region Variants

In certain embodiments, one or more amino acid modifications may be introduced into the Fc-region of an antibody provided herein, thereby generating an Fc-region variant. The Fc-region variant may comprise a human Fc-region sequence (e.g., a human IgG1, IgG2, IgG3 or IgG4 Fc-region) comprising an amino acid modification (e.g. a substitution) at one or more amino acid positions.

In certain embodiments, herein is provided an antibody variant that possesses some but not all effector functions, which make it a desirable candidate for applications in which the half-life of the antibody in vivo is important yet certain effector functions (such as complement and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express Fc (RIII only, whereas monocytes express FcγRI, FcγRII and FcγRIII. FcR expression on hematopoietic cells is summarized in Table 3 on page 464 of Ravetch, J. V. and Kinet, J. P., Annu. Rev. Immunol. 9 (1991) 457-492. Non-limiting examples of in vitro assays to assess ADCC activity of a molecule of interest is described in U.S. Pat. No. 5,500,362 (see, e.g. Hellstrom, I. et al., Proc. Natl. Acad. Sci. USA 83 (1986) 7059-7063; and Hellstrom, I. et al., Proc. Natl. Acad. Sci. USA 82 (1985) 1499-1502); U.S. Pat. No. 5,821,337 (see Bruggemann, M. et al., J. Exp. Med. 166 (1987) 1351-1361). Alternatively, non-radioactive assays methods may be employed (see, for example, ACTI™ non-radioactive cytotoxicity assay for flow cytometry (CellTechnology, Inc. Mountain View, Calif.; and CytoTox 96® non-radioactive cytotoxicity assay (Promega, Madison, Wis.). Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes, R. et al., Proc. Natl. Acad. Sci. USA 95 (1998) 652-656. C1q binding assays may also be carried out to confirm that the antibody is unable to bind C1q and hence lacks CDC activity. See, e.g., C1q and C3c binding ELISA in WO 2006/029879 and WO 2005/100402. To assess complement activation, a CDC assay may be performed (see, for example, Gazzano-Santoro, H. et al., J. Immunol. Methods 202 (1996) 163-171; Cragg, M. S. et al., Blood 101 (2003) 1045-1052; and Cragg, M. S. and M. J. Glennie, Blood 103 (2004) 2738-2743). FcRn binding and in vivo clearance/half-life determinations can also be performed using methods known in the art (see, e.g., Petkova, S. B. et al., Int. Immunol. 18 (2006: 1759-1769).

Antibodies with reduced effector function include those with substitution of one or more of Fc-region residues 238, 265, 269, 270, 297, 327 and 329 (U.S. Pat. No. 6,737,056). Such Fc mutants include Fc mutants with substitutions at two or more amino acid positions 265, 269, 270, 297 and 327, including the so-called "DANA" Fc mutant with substitution of residues 265 and 297 to alanine (U.S. Pat. No. 7,332,581).

Certain antibody variants with improved or diminished binding to FcRs are described. (See, e.g., U.S. Pat. No. 6,737,056; WO 2004/056312, and Shields, R. L. et al., J. Biol. Chem. 276 (2001) 6591-6604)

In certain embodiments, an antibody variant comprises an Fc-region with one or more amino acid substitutions which improve ADCC, e.g., substitutions at positions 298, 333, and/or 334 of the Fc-region (EU numbering of residues).

In some embodiments, alterations are made in the Fc-region that result in altered (i.e., either improved or diminished) C1q binding and/or Complement Dependent Cytotoxicity (CDC), e.g., as described in U.S. Pat. No. 6,194,551, WO 99/51642, and Idusogie, E. E. et al., J. Immunol. 164 (2000) 4178-4184.

Antibodies with increased half-lives and improved binding to the neonatal Fc receptor (FcRn), which is responsible for the transfer of maternal IgGs to the fetus (Guyer, R. L. et al., J. Immunol. 117 (1976) 587-593, and Kim, J. K. et al., J. Immunol. 24 (1994) 2429-2434), are described in US 2005/0014934. Those antibodies comprise an Fc-region with one or more substitutions therein which improve binding of the Fc-region to FcRn. Such Fc variants include those with substitutions at one or more of Fc-region residues: 238, 256, 265, 272, 286, 303, 305, 307, 311, 312, 317, 340, 356, 360, 362, 376, 378, 380, 382, 413, 424 or 434, e.g., substitution of Fc-region residue 434 (U.S. Pat. No. 7,371,826).

See also Duncan, A. R. and Winter, G., Nature 322 (1988) 738-740; U.S. Pat. Nos. 5,648,260; 5,624,821; and WO 94/29351 concerning other examples of Fc-region variants.

d) Cysteine Engineered Antibody Variants

In certain embodiments, it may be desirable to create cysteine engineered antibodies, e.g., "thioMAbs," in which one or more residues of an antibody are substituted with cysteine residues. In particular embodiments, the substituted residues occur at accessible sites of the antibody. By substituting those residues with cysteine, reactive thiol groups are thereby positioned at accessible sites of the antibody and may be used to conjugate the antibody to other moieties, such as drug moieties or linker-drug moieties, to create an immunoconjugate, as described further herein. In certain embodiments, any one or more of the following residues may be substituted with cysteine: V205 (Kabat numbering) of the light chain; A118 (EU numbering) of the heavy chain; and S400 (EU numbering) of the heavy chain Fc region. Cysteine engineered antibodies may be generated as described, e.g., in U.S. Pat. No. 7,521,541.

e) Antibody Derivatives

In certain embodiments, an antibody provided herein may be further modified to contain additional non-proteinaceous moieties that are known in the art and readily available. The moieties suitable for derivatization of the antibody include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1, 3-dioxolane, poly-1,3,6-trioxane, ethylene/maleic anhydride copolymer, polyaminoacids (either homopolymers or random copolymers), and dextran or poly(n-vinyl pyrrolidone) polyethylene glycol, propropylene glycol homopolymers, prolypropylene oxide/ethylene oxide copolymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer is attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

In another embodiment, conjugates of an antibody and non-proteinaceous moiety that may be selectively heated by exposure to radiation are provided. In one embodiment, the non-proteinaceous moiety is a carbon nanotube (Kam, N. W. et al., Proc. Natl. Acad. Sci. USA 102 (2005) 11600-11605). The radiation may be of any wavelength, and includes, but is not limited to, wavelengths that do not harm ordinary cells, but which heat the non-proteinaceous moiety to a temperature at which cells proximal to the antibody-non-proteinaceous moiety are killed.

B. Recombinant Methods and Compositions

Antibodies may be produced using recombinant methods and compositions, e.g., as described in U.S. Pat. No. 4,816,567. In one embodiment, isolated nucleic acid encoding an anti-human CD19 antibody described herein is provided. Such nucleic acid may encode an amino acid sequence comprising the VL and/or an amino acid sequence comprising the VH of the antibody (e.g., the light and/or heavy chains of the antibody). In a further embodiment, one or more vectors (e.g., expression vectors) comprising such nucleic acid are provided. In a further embodiment, a host cell comprising such nucleic acid is provided. In one such embodiment, a host cell comprises (e.g., has been transformed with): (1) a vector comprising a nucleic acid that encodes an amino acid sequence comprising the VL of the antibody and an amino acid sequence comprising the VH of the antibody, or (2) a first vector comprising a nucleic acid that encodes an amino acid sequence comprising the VL of the antibody and a second vector comprising a nucleic acid that encodes an amino acid sequence comprising the VH of the antibody. In one embodiment, the host cell is eukaryotic, e.g. a Chinese Hamster Ovary (CHO) cell or lymphoid cell (e.g., Y0, NS0, Sp20 cell). In one embodiment, a method of making an anti-human CD19 antibody is provided, wherein the method comprises culturing a host cell comprising a nucleic acid encoding the antibody, as provided above, under conditions suitable for expression of the antibody, and optionally recovering the antibody from the host cell (or host cell culture medium).

For recombinant production of an anti-human CD19 antibody, nucleic acid encoding an antibody, e.g., as described above, is isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the heavy and light chains of the antibody).

Suitable host cells for cloning or expression of antibody-encoding vectors include prokaryotic or eukaryotic cells described herein. For example, antibodies may be produced in bacteria, in particular when glycosylation and Fc effector function are not needed. For expression of antibody fragments and polypeptides in bacteria, see, e.g., U.S. Pat. Nos. 5,648,237, 5,789,199, and 5,840,523. (See also Charlton, K. A., In: Methods in Molecular Biology, Vol. 248, Lo, B. K. C. (ed.), Humana Press, Totowa, N.J. (2003), pp. 245-254, describing expression of antibody fragments in *E. coli*.) After expression, the antibody may be isolated from the bacterial cell paste in a soluble fraction and can be further purified.

In addition to prokaryotes, eukaryotic microbes such as filamentous fungi or yeast are suitable cloning or expression hosts for antibody-encoding vectors, including fungi and yeast strains whose glycosylation pathways have been "humanized," resulting in the production of an antibody with a partially or fully human glycosylation pattern. See Gerngross, T. U., Nat. Biotech. 22 (2004) 1409-1414; and Li, H. et al., Nat. Biotech. 24 (2006) 210-215.

Suitable host cells for the expression of glycosylated antibody are also derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells.

Plant cell cultures can also be utilized as hosts. See, e.g., U.S. Pat. Nos. 5,959,177, 6,040,498, 6,420,548, 7,125,978, and 6,417,429 (describing PLANTIBODIES™ technology for producing antibodies in transgenic plants).

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293 cells as described, e.g., in Graham, F. L. et al., J. Gen Virol. 36 (1977) 59-74); baby hamster kidney cells (BHK); mouse sertoli cells (TM4 cells as described, e.g., in Mather, J. P., Biol. Reprod. 23 (1980) 243-252); monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TRI cells, as described, e.g., in Mather, J. P. et al., Annals N.Y. Acad. Sci. 383 (1982) 44-68; MRC 5 cells; and FS4 cells. Other useful mammalian host cell lines include Chinese hamster ovary (CHO) cells, including DHFR⁻ CHO cells (Urlaub, G. et al., Proc. Natl. Acad. Sci. USA 77 (1980) 4216-4220); and myeloma cell lines such as Y0, NS0 and Sp2/0. For a review of certain mammalian host cell lines suitable for antibody production, see, e.g., Yazaki, P. and Wu, A. M., Methods in Molecular Biology, Vol. 248, Lo, B. K. C. (ed.), Humana Press, Totowa, N.J. (2004), pp. 255-268.

C. Assays

Anti-human CD19 antibodies provided herein may be identified, screened for, or characterized for their physical/chemical properties and/or biological activities by various assays known in the art.

1. Binding Assays and Other Assays

In one aspect, an antibody as reported herein is tested for its antigen binding activity, e.g., by known methods such as ELISA, Western blot, etc.

2. Activity Assays

In one aspect, assays are provided for identifying anti-human CD19 antibodies thereof having biological activity. Biological activity may include, e.g., inhibition of B-cell proliferation or killing of B-cells. Antibodies having such biological activity in vivo and/or in vitro are also provided.

In certain embodiments, an antibody as reported herein is tested for such biological activity.

D. Immunoconjugates

Herein are also provided immunoconjugates comprising an anti-human CD19 antibody as reported herein conjugated to one or more cytotoxic agents, such as chemotherapeutic agents or drugs, growth inhibitory agents, toxins (e.g., protein toxins, enzymatically active toxins of bacterial, fungal, plant, or animal origin, or fragments thereof), or radioactive isotopes.

In one embodiment, an immunoconjugate is an antibody-drug conjugate (ADC) in which an antibody is conjugated to one or more drugs, including but not limited to a maytansinoid (see U.S. Pat. Nos. 5,208,020, 5,416,064 and EP 0 425 235 B1); an auristatin such as monomethyl auristatin drug moieties DE and DF (MMAE and MMAF) (see U.S. Pat. Nos. 5,635,483, 5,780,588, and 7,498,298); a dolastatin; a calicheamicin or derivative thereof (see U.S. Pat. Nos. 5,712,374, 5,714,586, 5,739,116, 5,767,285, 5,770,701, 5,770,710, 5,773,001, and 5,877,296; Hinman, L. M. et al., Cancer Res. 53 (1993) 3336-3342; and Lode, H. N. et al., Cancer Res. 58 (1998) 2925-2928); an anthracycline such as daunomycin or doxorubicin (see Kratz, F. et al., Curr. Med. Chem. 13 (2006) 477-523; Jeffrey, S. C. et al., Bioorg. Med. Chem. Lett. 16 (2006) 358-362; Torgov, M. Y. et al., Bioconjug. Chem. 16 (2005) 717-721; Nagy, A. et al., Proc.

Natl. Acad. Sci. USA 97 (2000) 829-834; Dubowchik, G. M. et al., Bioorg. & Med. Chem. Letters 12 (2002) 1529-1532; King, H. D. et al., J. Med. Chem. 45 (20029 4336-4343; and U.S. Pat. No. 6,630,579); methotrexate; vindesine; a taxane such as docetaxel, paclitaxel, larotaxel, tesetaxel, and ortataxel; a trichothecene; and CC 1065.

In another embodiment, an immunoconjugate comprises an antibody as described herein conjugated to an enzymatically active toxin or fragment thereof, including but not limited to diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin, and the tricothecenes.

In another embodiment, an immunoconjugate comprises an antibody as described herein conjugated to a radioactive atom to form a radioconjugate. A variety of radioactive isotopes are available for the production of radioconjugates. Examples include $At^{211}$, $I^{131}$, $I^{125}$, $Y^{90}$, $Re^{186}$, $Re^{188}$, $Sm^{153}$, $Bi^{212}$, $Bi^{325}$, $Pb^{212}$ and radioactive isotopes of Lu. When the radioconjugate is used for detection, it may comprise a radioactive atom for scintigraphic studies, for example $TC^{99m}$ or $I^{123}$, or a spin label for nuclear magnetic resonance (NMR) imaging (also known as magnetic resonance imaging, MRI), such as iodine-123 again, iodine-131, indium-111, fluorine-19, carbon-13, nitrogen-15, oxygen-17, gadolinium, manganese or iron.

Conjugates of an antibody and cytotoxic agent may be made using a variety of bifunctional protein coupling agents such as N-succinimidyl-3-(2-pyridyldithio) propionate (SPDP), succinimidyl-4-(N-maleimidomethyl) cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta, E. S. et al., Science 238 (1987) 1098-1104. Carbon-14-labeled 1-isothiocyanatobenzyl-3-methyldiethylene triamine pentaacetic acid (MX-DTPA) is an exemplary chelating agent for conjugation of radionucleotide to the antibody. See WO 94/11026. The linker may be a "cleavable linker" facilitating release of a cytotoxic drug in the cell. For example, an acid-labile linker, peptidase-sensitive linker, photolabile linker, dimethyl linker or disulfide-containing linker (Chari, R. V. et al., Cancer Res. 52 (1992) 127-131; U.S. Pat. No. 5,208,020) may be used.

The immunoconjugates or ADCs herein expressly contemplate, but are not limited to such conjugates prepared with cross-linker reagents including, but not limited to, BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate) which are commercially available (e.g., from Pierce Biotechnology, Inc., Rockford, Ill., U.S.A).

E. Methods and Compositions for Diagnostics and Detection

In certain embodiments, any of the anti-human CD19 antibodies provided herein is useful for detecting the presence of human CD19 presenting cells in a biological sample. The term "detecting" as used herein encompasses quantitative or qualitative detection. In certain embodiments, a biological sample comprises a cell or tissue, such as e.g. blood, blood serum, or blood plasma.

In one embodiment, an anti-human CD19 antibody for use in a method of diagnosis or detection is provided. In a further aspect, a method of detecting the presence of human CD19 presenting cells in a biological sample is provided. In certain embodiments, the method comprises contacting the biological sample with an anti-human CD19 antibody as described herein under conditions permissive for binding of the anti-human CD19 antibody to human CD19, and detecting whether a complex is formed between the anti-human CD19 antibody and human CD19. Such method may be an in vitro or in vivo method. In one embodiment, an anti-human CD19 antibody is used to select subjects eligible for therapy with an anti-human CD19 antibody, e.g. where human CD19 is a biomarker for selection of patients.

Exemplary disorders that may be diagnosed using an antibody as reported herein include B-cell cancers, such as B-cell lymphoma and B-cell leukemias except for multiple myeloma, e.g. non-Hodgkin lymphoma and acute lymphoblastic leukemia.

In certain embodiments, labeled anti-human CD19 antibodies are provided. Labels include, but are not limited to, labels or moieties that are detected directly (such as fluorescent, chromophoric, electron-dense, chemiluminescent, and radioactive labels), as well as moieties, such as enzymes or ligands, that are detected indirectly, e.g., through an enzymatic reaction or molecular interaction. Exemplary labels include, but are not limited to, the radioisotopes $^{32}P$, $^{14}C$, $^{125}I$, $^{3}H$, and $^{131}I$, fluorophores such as rare earth chelates or fluorescein and its derivatives, rhodamine and its derivatives, dansyl, umbelliferone, luceriferases, e.g., firefly luciferase and bacterial luciferase (U.S. Pat. No. 4,737,456), luciferin, 2,3-dihydrophthalazinediones, horseradish peroxidase (HRP), alkaline phosphatase, β-galactosidase, glucoamylase, lysozyme, saccharide oxidases, e.g., glucose oxidase, galactose oxidase, and glucose-6-phosphate dehydrogenase, heterocyclic oxidases such as uricase and xanthine oxidase, coupled with an enzyme that employs hydrogen peroxide to oxidize a dye precursor such as HRP, lactoperoxidase, or microperoxidase, biotin/avidin, spin labels, bacteriophage labels, stable free radicals, and the like.

F. Pharmaceutical Formulations

Pharmaceutical formulations of an anti-human CD19 antibody as reported herein are prepared by mixing such antibody having the desired degree of purity with one or more optional pharmaceutically acceptable carriers (Remington's Pharmaceutical Sciences, 16*th* edition, Osol, A. (ed.) (1980)), in the form of lyophilized formulations or aqueous solutions. Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyl dimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as poly(vinylpyrrolidone); amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG). Exemplary pharmaceutically acceptable carriers herein further include interstitial drug dispersion agents such as soluble neutral-active hyaluronidase glycoproteins (sHASEGP), for example, human soluble PH-20 hyaluronidase glycoproteins, such as rhuPH20 (HYLENEX®, Baxter International, Inc.). Certain exemplary sHASEGPs and methods of use, including rhuPH20, are described in US 2005/0260186 and US 2006/0104968. In one aspect, a sHASEGP is combined with one or more additional glycosaminoglycanases such as chondroitinases.

Exemplary lyophilized antibody formulations are described in U.S. Pat. No. 6,267,958. Aqueous antibody formulations include those described in U.S. Pat. No. 6,171,586 and WO 2006/044908, the latter formulations including a histidine-acetate buffer.

The formulation herein may also contain more than one active ingredients as necessary for the particular indication being treated, preferably those with complementary activities that do not adversely affect each other. Such active ingredients are suitably present in combination in amounts that are effective for the purpose intended.

Active ingredients may be entrapped in microcapsules prepared, for example, by coacervation techniques or by interfacial polymerization, for example, hydroxymethylcellulose or gelatin-microcapsules and poly-(methyl methacrylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences, 16$^{th}$ edition, Osol, A. (ed.) (1980).

Sustained-release preparations may be prepared. Suitable examples of sustained-release preparations include semipermeable matrices of solid hydrophobic polymers containing the antibody, which matrices are in the form of shaped articles, e.g. films, or microcapsules.

The formulations to be used for in vivo administration are generally sterile. Sterility may be readily accomplished, e.g., by filtration through sterile filtration membranes.

G. Therapeutic Methods and Compositions

Any of the anti-human CD19 antibodies provided herein may be used in therapeutic methods, either alone or in combination, either as monospecific antibody or as multispecific antibody.

CD19 is expressed on most B-cells (pan-B-cell marker) with the exception of stem cells and plasma cells, and is frequently expressed on most human B-cell malignancies (tumor associated antigen), such as lymphoma and leukemias except for multiple myeloma, e.g. in non-Hodgkin lymphoma and acute lymphoblastic leukemia.

Bispecific antibodies recognizing two cell surface proteins on different cell populations hold the promise to redirect cytotoxic immune cells for destruction of pathogenic target cells.

In one aspect, an anti-human CD19 antibody for use as a medicament is provided. In further aspects, an anti-human CD19 antibody for use in treating a B-cell cancer is provided. In certain embodiments, an anti-human CD19 antibody for use in a method of treatment is provided. In certain embodiments, herein is provided an anti-human CD19 antibody for use in a method of treating an individual having a B-cell cancer comprising administering to the individual an effective amount of the anti-human CD19 antibody. In one such embodiment, the method further comprises administering to the individual an effective amount of at least one additional therapeutic agent. In further embodiments, herein is provided an anti-human CD19 antibody for use depleting B-cells. In certain embodiments, herein is provided an anti-human CD19 antibody for use in a method of depleting B-cells in an individual comprising administering to the individual an effective of the anti-human CD19 antibody to deplete B-cells. An "individual" according to any of the above embodiments is preferably a human. The B-cell cancer is in one embodiment a B-cell lymphoma or a B-cell leukemia. In one embodiment the B-cell cancer is non-Hodgkin lymphoma or acute lymphoblastic leukemia.

In further aspects, an anti-human CD19 antibody for use in cancer immunotherapy is provided. In certain embodiments, an anti-human CD19 antibody for use in a method of cancer immunotherapy is provided. An "individual" according to any of the above embodiments is preferably a human.

In a further aspect, herein is provided for the use of an anti-human CD19 antibody in the manufacture or preparation of a medicament. In one embodiment, the medicament is for treatment of a B-cell cancer. In a further embodiment, the medicament is for use in a method of treating a B-cell cancer comprising administering to an individual having a B-cell cancer an effective amount of the medicament. In one such embodiment, the method further comprises administering to the individual an effective amount of at least one additional therapeutic agent, e.g., as described below. In a further embodiment, the medicament is for depleting B-cells. In a further embodiment, the medicament is for use in a method of depleting B-cells in an individual comprising administering to the individual an amount effective of the medicament to deplete B-cells. An "individual" according to any of the above embodiments may be a human. The B-cell cancer is in one embodiment a B-cell lymphoma or a B-cell leukemia. In one embodiment the B-cell cancer is non-Hodgkin lymphoma or acute lymphoblastic leukemia.

In a further aspect, herein is provided a method for treating a B-cell cancer. In one embodiment, the method comprises administering to an individual having such B-cell cancer an effective amount of an anti-human CD19 antibody. In one such embodiment, the method further comprises administering to the individual an effective amount of at least one additional therapeutic agent, as described below. An "individual" according to any of the above embodiments may be a human. The B-cell cancer is in one embodiment a B-cell lymphoma or a B-cell leukemia. In one embodiment the B-cell cancer is non-Hodgkin lymphoma or acute lymphoblastic leukemia.

In a further aspect, herein is provided a method for depleting B-cells in an individual. In one embodiment, the method comprises administering to the individual an effective amount of an anti-human CD19 antibody to deplete B-cells. In one embodiment, an "individual" is a human. The B-cell cancer is in one embodiment a B-cell lymphoma or a B-cell leukemia. In one embodiment the B-cell cancer is non-Hodgkin lymphoma or acute lymphoblastic leukemia.

In a further aspect, herein is provided pharmaceutical formulations comprising any of the anti-human CD19 antibodies as reported herein, e.g., for use in any of the above therapeutic methods. In one embodiment, a pharmaceutical formulation comprises any of the anti-human CD19 antibodies as reported herein and a pharmaceutically acceptable carrier. In another embodiment, a pharmaceutical formulation comprises any of the anti-human CD19 antibodies as reported herein and at least one additional therapeutic agent.

Antibodies as reported herein can be used either alone or in combination with other agents in a therapy. For instance, an antibody as reported herein may be co-administered with at least one additional therapeutic agent.

Such combination therapies noted above encompass combined administration (where two or more therapeutic agents are included in the same or separate formulations), and separate administration, in which case, administration of the antibody as reported herein can occur prior to, simultaneously, and/or following, administration of the additional therapeutic agent or agents. In one embodiment, administration of the anti-human CD19 antibody and administration of an additional therapeutic agent occur within about one month, or within about one, two or three weeks, or within about one, two, three, four, five, or six days, of each other.

An antibody as reported herein (and any additional therapeutic agent) can be administered by any suitable means, including parenteral, intrapulmonary, and intranasal, and, if desired for local treatment, intralesional administration. Parenteral infusions include intramuscular, intravenous, intraarterial, intraperitoneal, or subcutaneous administration. Dosing can be by any suitable route, e.g. by injections, such as intravenous or subcutaneous injections, depending in part on whether the administration is brief or chronic. Various dosing schedules including but not limited to single or multiple administrations over various time-points, bolus administration, and pulse infusion are contemplated herein.

Antibodies as reported herein would be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The antibody need not be, but is optionally formulated with one or more agents currently used to prevent or treat the disorder in question. The effective amount of such other agents depends on the amount of antibody present in the formulation, the type of disorder or treatment, and other factors discussed above. These are generally used in the same dosages and with administration routes as described herein, or about from 1 to 99% of the dosages described herein, or in any dosage and by any route that is empirically/clinically determined to be appropriate.

For the prevention or treatment of disease, the appropriate dosage of an antibody as reported herein (when used alone or in combination with one or more other additional therapeutic agents) will depend on the type of disease to be treated, the type of antibody, the severity and course of the disease, whether the antibody is administered for preventive or therapeutic purposes, previous therapy, the patient's clinical history and response to the antibody, and the discretion of the attending physician. The antibody is suitably administered to the patient at one time or over a series of treatments. Depending on the type and severity of the disease, about 1 µg/kg to 15 mg/kg (e.g. 0.5 mg/kg-10 mg/kg) of antibody can be an initial candidate dosage for administration to the patient, whether, for example, by one or more separate administrations, or by continuous infusion. One typical daily dosage might range from about 1 µg/kg to 100 mg/kg or more, depending on the factors mentioned above. For repeated administrations over several days or longer, depending on the condition, the treatment would generally be sustained until a desired suppression of disease symptoms occurs. One exemplary dosage of the antibody would be in the range from about 0.05 mg/kg to about 10 mg/kg. Thus, one or more doses of about 0.5 mg/kg, 2.0 mg/kg, 4.0 mg/kg or 10 mg/kg (or any combination thereof) may be administered to the patient. Such doses may be administered intermittently, e.g. every week or every three weeks (e.g. such that the patient receives from about two to about twenty, or e.g. about six doses of the antibody). An initial higher loading dose, followed by one or more lower doses may be administered. However, other dosage regimens may be useful. The progress of this therapy is easily monitored by conventional techniques and assays.

Herein are further provided methods for treating an inflammatory disease, an autoimmune disease, rheumatoid arthritis, lupus, psoriasis, and a bone disease, comprising administering to a patient diagnosed as having such disease (and therefore being in need of such a therapy) an antibody specifically binding to human CD19 as reported herein. The antibody may be administered alone, in a pharmaceutical composition, or alternatively in combination with other medicaments for treating an inflammatory disease, an autoimmune disease, rheumatoid arthritis, lupus, psoriasis, or a bone disease. The antibody is administered in a pharmaceutically effective amount.

Herein are further provided the use of an antibody as reported herein for the treatment of an inflammatory disease, an autoimmune disease, rheumatoid arthritis, lupus, psoriasis or a bone disease, and for the manufacture of a pharmaceutical composition comprising an antibody as reported herein. In addition, herein is provided a method for the manufacture of a pharmaceutical composition comprising an antibody as reported herein.

Herein are further provided an antibody as reported herein for the treatment of an inflammatory disease, an autoimmune disease, rheumatoid arthritis, lupus, psoriasis, or a bone disease.

Further provided herein is the use of an antibody as reported herein for the manufacture of a pharmaceutical composition for the treatment of an inflammatory disease, an autoimmune disease, rheumatoid arthritis, lupus, psoriasis, or a bone disease. The antibody is used in a pharmaceutically effective amount.

Further provided herein is the use of an antibody as reported herein for the manufacture of a pharmaceutical composition for the treatment of an inflammatory disease, an autoimmune disease, rheumatoid arthritis, lupus, psoriasis, or a bone disease. The antibody is used in a pharmaceutically effective amount.

It is understood that any of the above formulations or therapeutic methods may be carried out using an immunoconjugate as reported herein in place of or in addition to an anti-human CD19 antibody.

III. Articles of Manufacture

In another aspect, an article of manufacture containing materials useful for the treatment, prevention and/or diagnosis of the disorders described above is provided. The article of manufacture comprises a container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition effective for treating, preventing and/or diagnosing the condition and may have a sterile access port (for example the container may be an intravenous solution bag or a vial having a stopper pierceable by a hypodermic injection needle). At least one active agent in the composition is an antibody as reported herein. The label or package insert indicates that the composition is used for treating the condition of choice.

Moreover, the article of manufacture may comprise (a) a first container with a composition contained therein, wherein the composition comprises an antibody as reported herein; and (b) a second container with a composition contained therein, wherein the composition comprises a further cytotoxic or otherwise therapeutic agent. The article of manufacture in this embodiment may further comprise a package insert indicating that the compositions can be used to treat a particular condition. Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

It is understood that any of the above articles of manufacture may include an immunoconjugate as reported herein in place of or in addition to an anti-human CD19 antibody.

IV. Description of the Sequence Listing

| | |
|---|---|
| SEQ ID NO: 1 | murine anti-human CD19 antibody 8B8 heavy chain variable domain |
| SEQ ID NO: 2 | murine anti-human CD19 antibody 8B8 light chain variable domain |
| SEQ ID NO: 3 | murine anti-human CD19 antibody 8B8 HVR-H1 |
| SEQ ID NO: 4 | murine anti-human CD19 antibody 8B8 HVR-H2 |
| SEQ ID NO: 5 | murine anti-human CD19 antibody 8B8 HVR-H3 |
| SEQ ID NO: 6 | murine anti-human CD19 antibody 8B8 HVR-L1 |
| SEQ ID NO: 7 | murine anti-human CD19 antibody 8B8 HVR-L2 |
| SEQ ID NO: 8 | murine anti-human CD19 antibody 8B8 HVR-L3 |
| SEQ ID NO: 9 | humanized heavy chain variable domain |
| SEQ ID NO: 10-28 | alternating the sequences of humanized light chain variable domain variant and humanized HVR-L1 variant |

V. Antibody Nomenclature

| antibody or antibody variable region | heavy chain variable domain (VH) | light chain variable domain (VL) | HVR-H1 | HVR-H2 | HVR-H3 | HVR-L1 | HVR-L2 | HVR-L3 |
|---|---|---|---|---|---|---|---|---|
| 0: wt | 1 | 2 | 3 | 4 | 5 | 6 | 7 | 8 |
| 1: N27dH | 9 | 10 | 3 | 11 | 5 | 12 | 7 | 8 |
| 2: N27dQ | 9 | 13 | 3 | 11 | 5 | 14 | 7 | 8 |
| 3: S27eA | 9 | 15 | 3 | 11 | 5 | 16 | 7 | 8 |
| 4: S27eV | 9 | 17 | 3 | 11 | 5 | 18 | 7 | 8 |
| 5: S27eP | 9 | 19 | 3 | 11 | 5 | 20 | 7 | 8 |
| 6: N28Q | 9 | 21 | 3 | 11 | 5 | 22 | 7 | 8 |
| 7: G29A | 9 | 23 | 3 | 11 | 5 | 24 | 7 | 8 |
| 8: G29V | 9 | 25 | 3 | 11 | 5 | 26 | 7 | 8 |
| 9: S27eP N28S | 9 | 27 | 3 | 11 | 5 | 28 | 7 | 8 |

VI. Examples

The following are examples of methods and compositions of the invention. It is understood that various other embodiments may be practiced, given the general description provided above.

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

Example 1

Immunization and Generation of Mouse Anti-Human CD19 Antibodies (Hybridomas)

Balb/c mice were immunized six times and boosted with CD19-transfected HEK293 cells (mean receptor density 35,000 per cell). The immune response was monitored by testing serum samples with a CD19-cell-ELISA on human CD19-transfected NIH-3T3 cells. Spleen cells from mice with sufficient titers of anti-human CD19 antibody were used for immortalization by fusion with mouse myeloma cell line P3X63 Ag8.653. Three fusions were carried out and hybridoma supernatants screened by cell-ELISA on human CD19-transfected NIH-3T3 cells and FACS binding assay using Daudi (CD19$^+$) and CD19$^-$ cells for anti-human CD19 specific antibodies.

Example 2

Hybridoma Screening and Cell Biological Functional Evaluation of Anti-CD19 Antibody Cell-ELISA for Screening Antibodies Against hCD19

A cell ELISA was applied for screening of hybridomas, and to identify those hybridomas that secrete antibodies against human-CD19. NIH3T3 cells transfected with human-CD19 were used as positive cells; non-transfected NIH3T3 cells were used as negative control cells. For the assessment of the positive hybridomas the OD ratio between transfected and non-transfected NIH3T3 cells was quantified.

Culture Medium: DMEM high glucose (4.5 mg/ml), 10% FCS, Na-Pyruvate, NEAA, Glutamine
Antibodies positive control: anti CD19 monoclonal antibody (IgG1) Pharmingen Cat #555409 c=1 mg/ml
Detection antibody: Goat anti-Mouse IgG (H+L) HRP Conjugate Bio-Rad Cat #170-06516
Dilution 1:2000 in 1×ELISA Blocking Reagent
Other reagents: Fibronectin Roche Cat #838039 c=1 mg/ml
Glutardialdehyde: 25% stock solution//Grade Agar Scientific # R102 final concentration: 0.05% in PBS
ELISA Blocking Reagent: 10× stock solution//Roche Cat #1112589
TMB substrate: Roche Cat #11432559
Stop Solution: 1 M $H_2SO_4$
BioRad Cat #170-6516 Dilution 1:2000 in 1×ELISA Blocking Reagent Day 1:
Fibronectin coating: 5 µg/cm² in PBS; 96 well plate=32 cm²; 160 µg/plate in 6 ml
PBS, 50 µl/well
incubate 45 min at RT, aspirate coating solution
Seed 1.25×10⁴ cells/well in 50 µl culture medium in a 96 well plate
incubate 40 hours at 37° C.
add to upper half of the plate: NIH3T3 cells expressing CD19
add to lower half of the plate: non-transfected NIH3T3 cells Day 3:
Addition of positive control antibody or samples (supernatant or mouse serum) in 50 µl culture medium
incubate for 2 h at 4° C.
Remove medium, fix cells with 100 µl Glutardialdehyde (0.05% in PBS)
Wash two times with 200 µl PBS
Addition of detection antibody 1:2000, 50 µl/well
incubate 2 h at RT
wash three times with 200 µl PBS
add 50 µl TMB, incubate for 30 min. at RT,
stop by addition of 25 µl 1 M $H_2SO_4$; read extinction at 450 nm/620 nm
Calculation of results: ratio OD NIH3T3 CD19:OD NIH3T3 non-transfected Example 3

Humanization of Anti-CD19 Antibody

The CD19 binding specificity of the murine antibody was transferred onto a human acceptor framework to eliminate potential immunogenicity issues arising from sequence stretches that the human body will recognize as foreign. This was done by engrafting the entire complementary determining regions (CDR) of the murine (donor) antibody onto a human (acceptor) antibody framework, and is called CDR-grafting or antibody humanization.

The murine amino acid sequence was aligned with a collection of human germ-line antibody V genes, and sorted according to sequence identity and homology. Before selecting one particular acceptor sequence, the so-called canonical loop structures of the donor antibody have to be determined (Morea, V., et al., Methods, Vol 20, Issue 3 (2000) 267-279). These canonical loop structures are determined by the type of residues present at the so-called canonical positions. These positions lie (partially) outside of the CDR regions, and have to be kept functionally equivalent in the final construct in order to retain the CDR conformation of the parental (donor) antibody. The human germ-line sequence VBASE_VH1_1 was chosen as the acceptor for the heavy chain and sequence VBASE_VK2_5 was chosen for the light chain. This resulted in the wild-type humanized antibody.

Example 4

Expression of CD19 Binding Antibodies

The antibody variable domain encoding sequences were generated by gene syntheses.

For the introduction of the respective point mutations a 33mer primer based quick change reaction was performed. All sequences were verified by sequencing (SequiServe, Vaterstetten, Germany). All sequences were cloned into vectors that enable selection and propagation in E. coli (origin of replication from the vector pUC18, beta-lactamase for ampicillin resistance). These vectors additionally contain cassettes that enable expression in mammalian cells (origin of replication, oriP, of Epstein-Barr virus (EBV), the immediate early enhancer and promoter from the human cytomegalovirus (HCMV) and a polyadenylation sequence).

All gene segments that code for antibody light and heavy chains are preceded by a DNA sequence coding for a signal peptide (MGWSCIILFLVATATGVHS; SEQ ID NO: 29). The proteins were expressed by transient transfection human embryonic kidney HEK 293 cells in suspension. These cells were cultivated at 37° C. and 8% $CO_2$. On the day of transfection, cells were seeded in fresh medium at a density of 1-2×10⁶ viable cells/mL. Equimolar amounts of both heavy and light chain plasmid DNAs were co-transfected. Cell culture supernatants were harvested 7 days after transfection, centrifuged (14,000×g for 45 min at 4° C.), and subsequently filtrated through a 0.22-µm filter. These supernatants could be frozen and stored at −20° C. before purification.

Example 5

Purification of CD19 Binding Antibodies

General Method:

Cell free fermentation supernatant (HEK 293F) is loaded onto a pre-equilibrated (phosphate buffered saline, PBS) protein A affinity column (MabSelect™ SuRe, GE Healthcare, 8×100 mm) with a contact time of 5 minutes. After washing (PBS, 5 column volumes) the antibody is eluted with 25 mM citric acid/NaOH (pH 3.0).

The eluate is adjusted to pH 5.5 with 1 M Tris and incubated overnight at 4° C. Thereafter a final filtration (0.45 µm) is performed:

Purification of Anti-Human CD19 Antibody Variant 5 (S27eP):

Cell free fermentation supernatant (244 ml, HEK 293F) was loaded onto a pre-equilibrated (phosphate buffered saline, PBS) protein A affinity column (MabSelect™ SuRe, GE Healthcare, 8×100 mm) with a contact time of 5 minutes. After washing (PBS, 5 column volumes) the antibody was eluted with 25 mM citric acid/NaOH (pH 3.0). The eluate was adjusted to pH 5.5 with 1 M Tris and incubated overnight at 4° C. Final filtration (0.45 µm) returned 31.1 mg (5.7 ml, 5.45 mg/ml) 99.0% (SEC) pure product.

Purification of Anti-Human CD19 Antibody Variant 9 (S27eP/N28S):

Cell free fermentation supernatant (260 ml, HEK 293F) was loaded onto a pre-equilibrated (PBS) protein A affinity column (MabSelect™ SuRe, GE Healthcare, 8×100 mm) with a contact time of 5 minutes. After washing (PBS, 5 column volumes) the target protein was eluted with 25 mM citric acid/NaOH (pH 3.0). The eluate was adjusted to pH 5.5 with 1 M Tris (pH 9.0) and incubated overnight at 4° C. Final filtration (0.2 µm) returned 9.1 mg (5.2 ml, 1.75 mg/ml) 98.0% (SEC) pure product.

Example 6

Provision of CD19 ECD Expressing Cells and Binding of the Antibodies Thereto

HEK293 cells were transfected with 1 µg of plasmid DNA per $1.5 \times 10^6$ cells using LipofectAmine 2000 and incubated thereafter for 48 hours at 37° C. The plasmids encoded either human CD19 (PEEPLVVKVE EGDNAVLQCL KGTSDGPTQQ LTWSRESPLK PFLKLSLGLP GLGIHMRPLA IWLFIFNVSQ QMGGFYLCQP GPPSEKAWQP GWTVNVEGSG ELFRWNVSDL GGLGCGLKNR SSEGPSSPSG KLMSPKLYVW AKDRPEIWEG EPPCLPPRDS LNQSLSQDLT MAPGSTLWLS CGVPPDSVSR GPLSWTHVHP KGPKSLLSLE LKDDRPARDM WVMETGLLLP RATAQDAGKY YCHRGNLTMS FHLEITARPV LWHWLLRTGG WK; SEQ ID NO: 30) or cynomolgus monkey CD 19 (PQEPLVVKVE EGDNAVLQCL EGTSDGPTQQ LVWCRDSPFE PFLNLSLGLP GMGIRMGPLG IWLLIFNVSN QTGGFYLCQP GLPSEKAWQP GWTVSVEGSG ELFRWNVSDL GGLGCGLKNR SSEGPSSPSG KLNSSQLYVW AKDRPEMWEG EPVCGPPRDS LNQSLSQDLT MAPGSTLWLS CGVPPDSVSR GPLSWTHVRP KGPKSSLLSL ELKDDRPDRD MWVVDTGLLL TRATAQDAGK YYCHRGNWTK SFYLEITARP ALWHWLLRIG GWKV; SEQ ID NO: 31) extracellular domain (ECD) fused to the human PSCA GPI anchor sequence (DTDLCNASGA HALQPAAAIL ALLPALGLLL WGPGQL; SEQ ID NO: 32) for extracellular presentation. The respective transfected cells were washed twice in FACS buffer (PBS containing 5% fetal bovine serum (FCS)) and resuspended in FACS buffer to a final concentration of $2 \times 10^6$ cells/mL corresponding to $5.0 \times 10^4$ cells/25 µL/well. The starting concentration of the antibodies was set to 60 µg/mL (2× final concentration) and then diluted in a 1:3 (v/v) titration series. The primary antibody was incubated on the cells for one hour at room temperature, followed by two wash steps. For secondary detection, anti-huIgG (H+L) antibody conjugated to Alexa488 in a concentration of 30 µg/mL was used. The secondary antibody was incubated for one hour at room temperature. Subsequently, the cells were washed twice and resuspended in 70 µL/well FACS buffer and analyzed using a BD FACS Canto.

The respective $EC_{50}$ values for the humanized wild-type antibody and variants 5 (S27eP) and 9 (S27eP/M28S) are shown in the following Table.

|  | wt [µg/mL] | variant 5 [µg/mL] | variant 9 [µg/mL] |
|---|---|---|---|
| human CD19-ECD | 0.087 | 0.084 | 0.089 |
| cynomolgus CD19-ECD | 0.313 | 0.255 | 0.435 |

Example 7

Mass Spectrometry (LC-MS/MS)

The antibody material (approximately 80 µg) was denatured in 200 mM histidine-HCl buffer (pH 6.0) comprising approximately 7 M Guanidinium-HCl, reduced using 10 mM TCEP, and buffer exchanged to 200 mM histidine-HCl (pH 6.0) using Zeba Spin Columns 7K MWCO (Thermo Scientific). Finally, the material was digested with 2.5 µg trypsin or thermolysin (Promega) for 16 hours at 37° C. Data acquisition was performed with a RP-UPLC gradient on a ACQUITY BEH300 C18 column (Waters) using a Nano-Acquity UPLC system (Waters) followed by CID based MS/MS on an Orbitrap Fusion Tribrid mass spectrometer (Thermo Scientific) with an TriVersa NanoMate (Advion) as NanoElectrospray ionization source. The data were evaluated using Mascot MS/MS Ion Searches (Matrix Science) and Peptide Analyzer (Roche Diagnostics GmbH), in-house MS data evaluation software. Quantification was performed by integration of extracted ion current chromatograms of the corresponding peptides.

Results:

The level of deamidation and succinimide formation upon incubation at 37° C. for 2 weeks at pH 7.4 in PBS buffer of the wild-type humanized anti-CD19 antibody (variant 0: wt) is shown in the following Table (used fragment: SSQSLENSNGNTYLNWYLQKPGQSPQLLIYR; SEQ ID NO: 35).

| sample | deamidated form [%] | succinimide formation [%] |
|---|---|---|
| reference | ~8 | 0 |
| incubated at 37° C. for 2 weeks at pH 7.4 in PBS buffer | 26-32 | 0 |

The level of deamidation and succinimide formation upon incubation of the humanized anti-CD19 antibody variant 5 (S27eP) is shown in the following Table (used fragment: SSQSLENPNGNTYLNWYLQKPGQSPQLLIYR; SEQ ID NO: 35).

| sample | deamidated form [%] | succinimide formation [%] |
|---|---|---|
| reference | 2 | 2 |
| incubated at 37° C. for 2 weeks at pH 7.4 in PBS buffer | 7 | 0 |
| incubated at 40° C. for 2 weeks at pH 6.0 in histidine/NaCl buffer | 4 | 2 |

The level of deamidation and succinimide formation upon incubation of the humanized anti-CD19 antibody variant 3 (S27eA) is shown in the following Table (used fragment: SSQSLENANGNTYLNWYLQKPGQSPQLLIYR; SEQ ID NO: 35).

| sample | deamidated form [%] | succinimide formation [%] |
|---|---|---|
| reference | 7 | 2 |
| incubated at 37° C. for 2 weeks at pH 7.4 in PBS buffer | 23 | 1 |
| incubated at 40° C. for 2 weeks at pH 6.0 in histidine/NaCl buffer | 13 | 1 |

The level of deamidation and succinimide formation upon incubation of the humanized anti-CD19 antibody variant 7 (G29A) is shown in the following Table (used fragment: SSQSLENSNANTYLNWYLQKPGQSPQLLIYR; SEQ ID NO: 35).

| sample | deamidated form [%] | succinimide formation [%] |
|---|---|---|
| reference | 8 | 0 |
| incubated at 37° C. for 2 weeks at pH 7.4 in PBS buffer | 45 | 0.5 |
| incubated at 40° C. for 2 weeks at pH 6.0 in histidine/NaCl buffer | 13 | 0 |

Example 8

CD19 Affinity Determination

A surface plasmon resonance (SPR) based assay was used to determine the kinetic parameters of the binding between the anti-human CD19 antibodies and the extracellular domain of recombinant human CD19 receptor.

Protocol 1:

To capture the anti-human CD19 antibody an anti-human F(ab)'2 antibody fragment as capture antibody was used (Jackson Immuno Research; order code: 109-006-006). Of the capture antibody 20 µg/mL were immobilized onto a CM5 chip (GE Healthcare; BR-1005-30) at pH 4.5 by using an amine coupling kit according to the manufacturer instructions (GE Healthcare). The sample and running buffers were HBS-EP+ (GE Healthcare; BR-1006-69). The flow cell was set to 25° C. The sample block was set to 12° C. Both were primed with running buffer. The anti-human CD19 antibody was captured by injecting a 35 nM solution for 60 sec. at a flow of 20 µL/min. Association was measured by injection of recombinant human CD19 ECD in various concentrations in solution for 120 sec. at a flow of 50 µL/min, starting with 900 nM in 1:3 dilutions and five concentrations in total. The dissociation phase was monitored for up to 600 sec. and triggered by switching from the sample solution to running buffer. The surface was regenerated two times by 60 sec. and 30 sec. washing with a 10 mM glycine solution (pH 1.5) at a flow rate of 30 µL/min. Bulk refractive index differences were corrected by subtracting the response obtained from a goat anti-human F(ab)'2 surface. Blank injections are also subtracted (=double referencing). For calculation of apparent KD and other kinetic parameters the Langmuir 1:1 model was used.

Protocol 2:

To capture the anti-human CD19 antibody an anti-human Fab capture antibody was used. First 30 µg/mL goat anti-human Fab antibody (Order Code: 28958325; GE Healthcare Bio-Sciences AB) was immobilized onto a CM5 chip (GE Healthcare; BR-1005-30) at pH 5.0 by using an amine coupling kit (GE Healthcare) according to the manufacturer's instructions. The sample and running buffer was HBS-EP+(GE Healthcare; BR-1006-69). The flow cell was set to 25° C. The sample block was set to 12° C. Both were primed with running buffer. The anti-human CD19 antibody was captured by injecting a 10 nM solution for 60 sec. at a flow of 10 µL/min. Association was measured by injection of recombinant human CD19 ECD for 90 sec. at a flow rate of 10 µL/min at a concentration of 250 nM. The dissociation phase was monitored for up to 60 sec. and triggered by switching from the sample solution to running buffer. The surface was regenerated by 60 sec. washing with a 10 mM glycine solution (pH 2.1) at a flow rate of 10 µL/min. Bulk refracting index differences were corrected by subtracting the response from a blank surface.

Calculation:

The relative binding of a sample is the ratio calculated from the capture level and binding level (RU binding divided by RU capture):

$$\text{rel\_binding} = \frac{\text{binding\_level}}{\text{capture\_level}}$$

The relative active concentration of the sample is the ratio of a sample as compared to a reference sample:

$$\text{rel\_active\_conc} = \frac{\text{rel\_binding}_{sample}}{\text{rel\_binding}_{reference}}$$

The invention claimed is:

1. An antibody that specifically binds to human CD19, wherein the antibody comprises,
    (a) HVR-H1 comprising the amino acid sequence of SEQ ID NO: 03,
    (b) HVR-H2 comprising the amino acid sequence of SEQ ID NO: 11,
    (c) HVR-H3 comprising the amino acid sequence of SEQ ID NO: 05,
    (d) HVR-L1 comprising the amino acid sequence of SEQ ID NO: 20 or 28,
    (e) HVR-L2 comprising the amino acid sequence of SEQ ID NO: 07, and
    (f) HVR-L3 comprising the amino acid sequence of SEQ ID NO: 08.

2. The antibody according to claim 1, wherein the antibody is a monoclonal antibody.

3. The antibody according to claim 1, wherein the antibody is humanized or chimeric antibody.

4. The antibody according to claim 1, wherein the antibody is an antibody fragment that specifically binds to human CD19.

5. The antibody according to claim 1, wherein the antibody comprises:
    (a) a VH sequence having at least 95% sequence identity to the amino acid sequence of SEQ ID NO: 09 and a VL sequence having at least 95% sequence identity to the amino acid sequence of SEQ ID NO: 19, or
    (b) a VH sequence having at least 95% sequence identity to the amino acid sequence of SEQ ID NO: 09 and a VL sequence having at least 95% sequence identity to the amino acid sequence of SEQ ID NO: 27, or
    (c) a VH sequence and a VL sequence as in (a) or (b).

6. A pharmaceutical formulation, comprising the antibody according to claim 1 and a pharmaceutically acceptable carrier.

7. A method of treating an individual having a B-cell cancer, comprising the step of administering to the individual an effective amount of the antibody according to claim 1.

8. A method of depleting B-cells in an individual in need thereof, comprising the step of administering to the individual an effective amount of the antibody according to claim 1 to deplete B-cells.

* * * * *

SEQUENCE LISTING

```
<160> NUMBER OF SEQ ID NOS: 70

<210> SEQ ID NO 1
<211> LENGTH: 121
<212> TYPE: PRT
<213> ORGANISM: Mus musculus

<400> SEQUENCE: 1

Glu Val Gln Leu Gln Gln Ser Gly Pro Glu Leu Val Lys Pro Gly Ala
1               5                   10                  15

Ser Val Lys Met Ala Cys Lys Ala Ser Gly Tyr Thr Phe Thr Asp Tyr
            20                  25                  30

Ile Met His Trp Val Lys Gln Lys Thr Gly Gln Gly Leu Glu Trp Ile
        35                  40                  45

Gly Tyr Ile Asn Pro Tyr Asn Asp Gly Ser Lys Tyr Thr Glu Lys Phe
    50                  55                  60

Asn Gly Lys Ala Thr Leu Thr Ser Asp Lys Ser Ser Ile Thr Ala Tyr
65                  70                  75                  80

Met Glu Leu Ser Ser Leu Thr Ser Glu Asp Ser Ala Val Tyr Tyr Cys
```

```
                    85                  90                  95
Ala Arg Gly Thr Tyr Tyr Tyr Gly Ser Ala Leu Phe Asp Tyr Trp Gly
                100                 105                 110

Gln Gly Thr Thr Leu Thr Val Ser Ser
            115                 120

<210> SEQ ID NO 2
<211> LENGTH: 112
<212> TYPE: PRT
<213> ORGANISM: Mus musculus

<400> SEQUENCE: 2

Asp Ala Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Glu Asn Ser
            20                  25                  30

Asn Gly Asn Thr Tyr Leu Asn Trp Tyr Leu Gln Lys Pro Gly Gln Ser
        35                  40                  45

Pro Gln Leu Leu Ile Tyr Arg Val Ser Lys Arg Phe Ser Gly Val Leu
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Leu Gln Leu
                85                  90                  95

Thr His Val Pro Tyr Thr Phe Gly Gly Gly Thr Lys Leu Glu Ile Lys
            100                 105                 110

<210> SEQ ID NO 3
<211> LENGTH: 5
<212> TYPE: PRT
<213> ORGANISM: Mus musculus

<400> SEQUENCE: 3

Asp Tyr Ile Met His
1               5

<210> SEQ ID NO 4
<211> LENGTH: 17
<212> TYPE: PRT
<213> ORGANISM: Mus musculus

<400> SEQUENCE: 4

Tyr Ile Asn Pro Tyr Asn Asp Gly Ser Lys Tyr Thr Glu Lys Phe Asn
1               5                   10                  15

Gly

<210> SEQ ID NO 5
<211> LENGTH: 12
<212> TYPE: PRT
<213> ORGANISM: Mus musculus

<400> SEQUENCE: 5

Gly Thr Tyr Tyr Tyr Gly Ser Ala Leu Phe Asp Tyr
1               5                   10

<210> SEQ ID NO 6
<211> LENGTH: 16
<212> TYPE: PRT
<213> ORGANISM: Mus musculus

<400> SEQUENCE: 6
```

Arg Ser Ser Gln Ser Leu Glu Asn Ser Asn Gly Asn Thr Tyr Leu Asn
1               5                   10                  15

<210> SEQ ID NO 7
<211> LENGTH: 7
<212> TYPE: PRT
<213> ORGANISM: Mus musculus

<400> SEQUENCE: 7

Arg Val Ser Lys Arg Phe Ser
1               5

<210> SEQ ID NO 8
<211> LENGTH: 9
<212> TYPE: PRT
<213> ORGANISM: Mus musculus

<400> SEQUENCE: 8

Leu Gln Leu Thr His Val Pro Tyr Thr
1               5

<210> SEQ ID NO 9
<211> LENGTH: 121
<212> TYPE: PRT
<213> ORGANISM: Artificial Sequence
<220> FEATURE:
<223> OTHER INFORMATION: humanized VH

<400> SEQUENCE: 9

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
                20                  25                  30

Ile Met His Trp Val Arg Gln Ala Pro Gly Gln Gly Leu Glu Trp Met
            35                  40                  45

Gly Tyr Ile Asn Pro Tyr Asn Asp Gly Ser Lys Tyr Thr Glu Lys Phe
    50                  55                  60

Gln Gly Arg Val Thr Met Thr Ser Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Thr Tyr Tyr Gly Ser Ala Leu Phe Asp Tyr Trp Gly
                100                 105                 110

Gln Gly Thr Thr Val Thr Val Ser Ser
        115                 120

<210> SEQ ID NO 10
<211> LENGTH: 112
<212> TYPE: PRT
<213> ORGANISM: Artificial Sequence
<220> FEATURE:
<223> OTHER INFORMATION: N27dH VL

<400> SEQUENCE: 10

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Glu His Ser
                20                  25                  30

Asn Gly Asn Thr Tyr Leu Asn Trp Tyr Leu Gln Lys Pro Gly Gln Ser
            35                  40                  45

```
Pro Gln Leu Leu Ile Tyr Arg Val Ser Lys Arg Phe Ser Gly Val Pro
    50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Leu Gln Leu
                 85                  90                  95

Thr His Val Pro Tyr Thr Phe Gly Gln Gly Thr Lys Leu Glu Ile Lys
            100                 105                 110

<210> SEQ ID NO 11
<211> LENGTH: 17
<212> TYPE: PRT
<213> ORGANISM: Artificial Sequence
<220> FEATURE:
<223> OTHER INFORMATION: humanized HVR-H2

<400> SEQUENCE: 11

Tyr Ile Asn Pro Tyr Asn Asp Gly Ser Lys Tyr Thr Glu Lys Phe Gln
 1               5                  10                  15

Gly

<210> SEQ ID NO 12
<211> LENGTH: 16
<212> TYPE: PRT
<213> ORGANISM: Artificial Sequence
<220> FEATURE:
<223> OTHER INFORMATION: N27dH HVR-L1

<400> SEQUENCE: 12

Lys Ser Ser Gln Ser Leu Glu His Ser Asn Gly Asn Thr Tyr Leu Asn
 1               5                  10                  15

<210> SEQ ID NO 13
<211> LENGTH: 112
<212> TYPE: PRT
<213> ORGANISM: Artificial Sequence
<220> FEATURE:
<223> OTHER INFORMATION: N27dQ VL

<400> SEQUENCE: 13

Asp Ile Val Met Thr Gln Thr Pro Leu Ser Leu Ser Val Thr Pro Gly
 1               5                  10                  15

Gln Pro Ala Ser Ile Ser Cys Lys Ser Ser Gln Ser Leu Glu Gln Ser
             20                  25                  30

Asn Gly Asn Thr Tyr Leu Asn Trp Tyr Leu Gln Lys Pro Gly Gln Ser
         35                  40                  45

Pro Gln Leu Leu Ile Tyr Arg Val Ser Lys Arg Phe Ser Gly Val Pro
    50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Leu Gln Leu
                 85                  90                  95

Thr His Val Pro Tyr Thr Phe Gly Gln Gly Thr Lys Leu Glu Ile Lys
            100                 105                 110

<210> SEQ ID NO 14
<211> LENGTH: 16
<212> TYPE: PRT
<213> ORGANISM: Artificial Sequence
<220> FEATURE:
<223> OTHER INFORMATION: N27dQ HVR-L1
```

```
<400> SEQUENCE: 14

Lys Ser Ser Gln Ser Leu Glu Gln Ser Asn Gly Asn Thr Tyr Leu Asn
1               5                   10                  15

<210> SEQ ID NO 15
<211> LENGTH: 112
<212> TYPE: PRT
<213> ORGANISM: Artificial Sequence
<220> FEATURE:
<223> OTHER INFORMATION: S27eA VH

<400> SEQUENCE: 15

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Glu Asn Ala
            20                  25                  30

Asn Gly Asn Thr Tyr Leu Asn Trp Tyr Leu Gln Lys Pro Gly Gln Ser
        35                  40                  45

Pro Gln Leu Leu Ile Tyr Arg Val Ser Lys Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Leu Gln Leu
                85                  90                  95

Thr His Val Pro Tyr Thr Phe Gly Gln Gly Thr Lys Leu Glu Ile Lys
            100                 105                 110

<210> SEQ ID NO 16
<211> LENGTH: 16
<212> TYPE: PRT
<213> ORGANISM: Artificial Sequence
<220> FEATURE:
<223> OTHER INFORMATION: S27eA HVR-L1

<400> SEQUENCE: 16

Lys Ser Ser Gln Ser Leu Glu Asn Ala Asn Gly Asn Thr Tyr Leu Asn
1               5                   10                  15

<210> SEQ ID NO 17
<211> LENGTH: 112
<212> TYPE: PRT
<213> ORGANISM: Artificial Sequence
<220> FEATURE:
<223> OTHER INFORMATION: S27eV VL

<400> SEQUENCE: 17

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Glu Asn Val
            20                  25                  30

Asn Gly Asn Thr Tyr Leu Asn Trp Tyr Leu Gln Lys Pro Gly Gln Ser
        35                  40                  45

Pro Gln Leu Leu Ile Tyr Arg Val Ser Lys Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Leu Gln Leu
                85                  90                  95

Thr His Val Pro Tyr Thr Phe Gly Gln Gly Thr Lys Leu Glu Ile Lys
            100                 105                 110
```

```
<210> SEQ ID NO 18
<211> LENGTH: 16
<212> TYPE: PRT
<213> ORGANISM: Artificial Sequence
<220> FEATURE:
<223> OTHER INFORMATION: S27eV HVR-L1

<400> SEQUENCE: 18

Lys Ser Ser Gln Ser Leu Glu Asn Val Asn Gly Asn Thr Tyr Leu Asn
1               5                   10                  15

<210> SEQ ID NO 19
<211> LENGTH: 112
<212> TYPE: PRT
<213> ORGANISM: Artificial Sequence
<220> FEATURE:
<223> OTHER INFORMATION: S27eP VL

<400> SEQUENCE: 19

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Glu Asn Pro
            20                  25                  30

Asn Gly Asn Thr Tyr Leu Asn Trp Tyr Leu Gln Lys Pro Gly Gln Ser
        35                  40                  45

Pro Gln Leu Leu Ile Tyr Arg Val Ser Lys Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Leu Gln Leu
                85                  90                  95

Thr His Val Pro Tyr Thr Phe Gly Gln Gly Thr Lys Leu Glu Ile Lys
            100                 105                 110

<210> SEQ ID NO 20
<211> LENGTH: 16
<212> TYPE: PRT
<213> ORGANISM: Artificial Sequence
<220> FEATURE:
<223> OTHER INFORMATION: S27eP HVR-L1

<400> SEQUENCE: 20

Lys Ser Ser Gln Ser Leu Glu Asn Pro Asn Gly Asn Thr Tyr Leu Asn
1               5                   10                  15

<210> SEQ ID NO 21
<211> LENGTH: 112
<212> TYPE: PRT
<213> ORGANISM: Artificial Sequence
<220> FEATURE:
<223> OTHER INFORMATION: N28Q VL

<400> SEQUENCE: 21

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Glu Asn Ser
            20                  25                  30

Gln Gly Asn Thr Tyr Leu Asn Trp Tyr Leu Gln Lys Pro Gly Gln Ser
        35                  40                  45

Pro Gln Leu Leu Ile Tyr Arg Val Ser Lys Arg Phe Ser Gly Val Pro
    50                  55                  60
```

```
Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Leu Gln Leu
                85                  90                  95

Thr His Val Pro Tyr Thr Phe Gly Gln Gly Thr Lys Leu Glu Ile Lys
            100                 105                 110
```

<210> SEQ ID NO 22
<211> LENGTH: 16
<212> TYPE: PRT
<213> ORGANISM: Artificial Sequence
<220> FEATURE:
<223> OTHER INFORMATION: N28Q HVR-L1

<400> SEQUENCE: 22

```
Lys Ser Ser Gln Ser Leu Glu Asn Ser Gln Gly Asn Thr Tyr Leu Asn
1               5                   10                  15
```

<210> SEQ ID NO 23
<211> LENGTH: 112
<212> TYPE: PRT
<213> ORGANISM: Artificial Sequence
<220> FEATURE:
<223> OTHER INFORMATION: G29A VL

<400> SEQUENCE: 23

```
Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Glu Asn Ser
            20                  25                  30

Asn Ala Asn Thr Tyr Leu Asn Trp Tyr Leu Gln Lys Pro Gly Gln Ser
        35                  40                  45

Pro Gln Leu Leu Ile Tyr Arg Val Ser Lys Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Leu Gln Leu
                85                  90                  95

Thr His Val Pro Tyr Thr Phe Gly Gln Gly Thr Lys Leu Glu Ile Lys
            100                 105                 110
```

<210> SEQ ID NO 24
<211> LENGTH: 16
<212> TYPE: PRT
<213> ORGANISM: Artificial Sequence
<220> FEATURE:
<223> OTHER INFORMATION: G29A HVR-L1

<400> SEQUENCE: 24

```
Lys Ser Ser Gln Ser Leu Glu Asn Ser Asn Ala Asn Thr Tyr Leu Asn
1               5                   10                  15
```

<210> SEQ ID NO 25
<211> LENGTH: 112
<212> TYPE: PRT
<213> ORGANISM: Artificial Sequence
<220> FEATURE:
<223> OTHER INFORMATION: G29V VL

<400> SEQUENCE: 25

```
Asp Ile Val Met Thr Gln Thr Pro Leu Ser Leu Ser Val Thr Pro Gly
1               5                   10                  15
```

Gln Pro Ala Ser Ile Ser Cys Lys Ser Ser Gln Ser Leu Glu Asn Ser
            20                  25                  30

Asn Val Asn Thr Tyr Leu Asn Trp Tyr Leu Gln Lys Pro Gly Gln Ser
        35                  40                  45

Pro Gln Leu Leu Ile Tyr Arg Val Ser Lys Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Leu Gln Leu
                85                  90                  95

Thr His Val Pro Tyr Thr Phe Gly Gln Gly Thr Lys Leu Glu Ile Lys
            100                 105                 110

<210> SEQ ID NO 26
<211> LENGTH: 16
<212> TYPE: PRT
<213> ORGANISM: Artificial Sequence
<220> FEATURE:
<223> OTHER INFORMATION: G29V HVR-L1

<400> SEQUENCE: 26

Lys Ser Ser Gln Ser Leu Glu Asn Ser Asn Val Asn Thr Tyr Leu Asn
1               5                   10                  15

<210> SEQ ID NO 27
<211> LENGTH: 112
<212> TYPE: PRT
<213> ORGANISM: Artificial Sequence
<220> FEATURE:
<223> OTHER INFORMATION: S27eP/N28S VH

<400> SEQUENCE: 27

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Glu Asn Pro
            20                  25                  30

Ser Gly Asn Thr Tyr Leu Asn Trp Tyr Leu Gln Lys Pro Gly Gln Ser
        35                  40                  45

Pro Gln Leu Leu Ile Tyr Arg Val Ser Lys Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Leu Gln Leu
                85                  90                  95

Thr His Val Pro Tyr Thr Phe Gly Gln Gly Thr Lys Leu Glu Ile Lys
            100                 105                 110

<210> SEQ ID NO 28
<211> LENGTH: 16
<212> TYPE: PRT
<213> ORGANISM: Artificial Sequence
<220> FEATURE:
<223> OTHER INFORMATION: S27eP/N28S HVR-L1

<400> SEQUENCE: 28

Lys Ser Ser Gln Ser Leu Glu Asn Pro Ser Gly Asn Thr Tyr Leu Asn
1               5                   10                  15

<210> SEQ ID NO 29
<211> LENGTH: 19

```
<212> TYPE: PRT
<213> ORGANISM: Artificial Sequence
<220> FEATURE:
<223> OTHER INFORMATION: signal peptide

<400> SEQUENCE: 29
```

Met Gly Trp Ser Cys Ile Ile Leu Phe Leu Val Ala Thr Ala Thr Gly
1               5                   10                  15

Val His Ser

```
<210> SEQ ID NO 30
<211> LENGTH: 272
<212> TYPE: PRT
<213> ORGANISM: Homo sapiens

<400> SEQUENCE: 30
```

Pro Glu Glu Pro Leu Val Val Lys Val Glu Glu Gly Asp Asn Ala Val
1               5                   10                  15

Leu Gln Cys Leu Lys Gly Thr Ser Asp Gly Pro Thr Gln Gln Leu Thr
            20                  25                  30

Trp Ser Arg Glu Ser Pro Leu Lys Pro Phe Leu Lys Leu Ser Leu Gly
        35                  40                  45

Leu Pro Gly Leu Gly Ile His Met Arg Pro Leu Ala Ile Trp Leu Phe
    50                  55                  60

Ile Phe Asn Val Ser Gln Gln Met Gly Gly Phe Tyr Leu Cys Gln Pro
65                  70                  75                  80

Gly Pro Pro Ser Glu Lys Ala Trp Gln Pro Gly Trp Thr Val Asn Val
                85                  90                  95

Glu Gly Ser Gly Glu Leu Phe Arg Trp Asn Val Ser Asp Leu Gly Gly
            100                 105                 110

Leu Gly Cys Gly Leu Lys Asn Arg Ser Ser Glu Gly Pro Ser Ser Pro
        115                 120                 125

Ser Gly Lys Leu Met Ser Pro Lys Leu Tyr Val Trp Ala Lys Asp Arg
    130                 135                 140

Pro Glu Ile Trp Glu Gly Glu Pro Pro Cys Leu Pro Pro Arg Asp Ser
145                 150                 155                 160

Leu Asn Gln Ser Leu Ser Gln Asp Leu Thr Met Ala Pro Gly Ser Thr
                165                 170                 175

Leu Trp Leu Ser Cys Gly Val Pro Pro Asp Ser Val Ser Arg Gly Pro
            180                 185                 190

Leu Ser Trp Thr His Val His Pro Lys Gly Pro Lys Ser Leu Leu Ser
        195                 200                 205

Leu Glu Leu Lys Asp Asp Arg Pro Ala Arg Asp Met Trp Val Met Glu
    210                 215                 220

Thr Gly Leu Leu Leu Pro Arg Ala Thr Ala Gln Asp Ala Gly Lys Tyr
225                 230                 235                 240

Tyr Cys His Arg Gly Asn Leu Thr Met Ser Phe His Leu Glu Ile Thr
                245                 250                 255

Ala Arg Pro Val Leu Trp His Trp Leu Leu Arg Thr Gly Gly Trp Lys
            260                 265                 270

```
<210> SEQ ID NO 31
<211> LENGTH: 274
<212> TYPE: PRT
<213> ORGANISM: Macaca fascicularis

<400> SEQUENCE: 31
```

```
Pro Gln Glu Pro Leu Val Val Lys Val Glu Glu Gly Asp Asn Ala Val
1               5                   10                  15

Leu Gln Cys Leu Glu Gly Thr Ser Asp Gly Pro Thr Gln Gln Leu Val
                20                  25                  30

Trp Cys Arg Asp Ser Pro Phe Glu Pro Phe Leu Asn Leu Ser Leu Gly
            35                  40                  45

Leu Pro Gly Met Gly Ile Arg Met Gly Pro Leu Gly Ile Trp Leu Leu
        50                  55                  60

Ile Phe Asn Val Ser Asn Gln Thr Gly Gly Phe Tyr Leu Cys Gln Pro
65                  70                  75                  80

Gly Leu Pro Ser Glu Lys Ala Trp Gln Pro Gly Trp Thr Val Ser Val
                85                  90                  95

Glu Gly Ser Gly Glu Leu Phe Arg Trp Asn Val Ser Asp Leu Gly Gly
            100                 105                 110

Leu Gly Cys Gly Leu Lys Asn Arg Ser Ser Glu Gly Pro Ser Ser Pro
        115                 120                 125

Ser Gly Lys Leu Asn Ser Ser Gln Leu Tyr Val Trp Ala Lys Asp Arg
    130                 135                 140

Pro Glu Met Trp Glu Gly Glu Pro Val Cys Gly Pro Pro Arg Asp Ser
145                 150                 155                 160

Leu Asn Gln Ser Leu Ser Gln Asp Leu Thr Met Ala Pro Gly Ser Thr
                165                 170                 175

Leu Trp Leu Ser Cys Gly Val Pro Pro Asp Ser Val Ser Arg Gly Pro
            180                 185                 190

Leu Ser Trp Thr His Val Arg Pro Lys Gly Pro Lys Ser Ser Leu Leu
        195                 200                 205

Ser Leu Glu Leu Lys Asp Asp Arg Pro Asp Arg Asp Met Trp Val Val
    210                 215                 220

Asp Thr Gly Leu Leu Leu Thr Arg Ala Thr Ala Gln Asp Ala Gly Lys
225                 230                 235                 240

Tyr Tyr Cys His Arg Gly Asn Trp Thr Lys Ser Phe Tyr Leu Glu Ile
                245                 250                 255

Thr Ala Arg Pro Ala Leu Trp His Trp Leu Leu Arg Ile Gly Gly Trp
            260                 265                 270

Lys Val

<210> SEQ ID NO 32
<211> LENGTH: 36
<212> TYPE: PRT
<213> ORGANISM: Homo sapiens

<400> SEQUENCE: 32

Asp Thr Asp Leu Cys Asn Ala Ser Gly Ala His Ala Leu Gln Pro Ala
1               5                   10                  15

Ala Ala Ile Leu Ala Leu Leu Pro Ala Leu Gly Leu Leu Leu Trp Gly
                20                  25                  30

Pro Gly Gln Leu
        35

<210> SEQ ID NO 33
<211> LENGTH: 537
<212> TYPE: PRT
<213> ORGANISM: Homo sapiens

<400> SEQUENCE: 33

Pro Glu Glu Pro Leu Val Val Lys Val Glu Glu Gly Asp Asn Ala Val
```

```
1               5                    10                   15
Leu Gln Cys Leu Lys Gly Thr Ser Asp Gly Pro Thr Gln Gln Leu Thr
                20                  25                  30

Trp Ser Arg Glu Ser Pro Leu Lys Pro Phe Leu Lys Leu Ser Leu Gly
        35                  40                  45

Leu Pro Gly Leu Gly Ile His Met Arg Pro Leu Ala Ile Trp Leu Phe
    50                  55                  60

Ile Phe Asn Val Ser Gln Gln Met Gly Gly Phe Tyr Leu Cys Gln Pro
65                  70                  75                  80

Gly Pro Pro Ser Glu Lys Ala Trp Gln Pro Gly Trp Thr Val Asn Val
                85                  90                  95

Glu Gly Ser Gly Glu Leu Phe Arg Trp Asn Val Ser Asp Leu Gly Gly
                100                 105                 110

Leu Gly Cys Gly Leu Lys Asn Arg Ser Ser Glu Gly Pro Ser Ser Pro
            115                 120                 125

Ser Gly Lys Leu Met Ser Pro Lys Leu Tyr Val Trp Ala Lys Asp Arg
    130                 135                 140

Pro Glu Ile Trp Glu Gly Glu Pro Pro Cys Leu Pro Pro Arg Asp Ser
145                 150                 155                 160

Leu Asn Gln Ser Leu Ser Gln Asp Leu Thr Met Ala Pro Gly Ser Thr
                165                 170                 175

Leu Trp Leu Ser Cys Gly Val Pro Pro Asp Ser Val Ser Arg Gly Pro
            180                 185                 190

Leu Ser Trp Thr His Val His Pro Lys Gly Pro Lys Ser Leu Leu Ser
    195                 200                 205

Leu Glu Leu Lys Asp Asp Arg Pro Ala Arg Asp Met Trp Val Met Glu
    210                 215                 220

Thr Gly Leu Leu Leu Pro Arg Ala Thr Ala Gln Asp Ala Gly Lys Tyr
225                 230                 235                 240

Tyr Cys His Arg Gly Asn Leu Thr Met Ser Phe His Leu Glu Ile Thr
                245                 250                 255

Ala Arg Pro Val Leu Trp His Trp Leu Leu Arg Thr Gly Gly Trp Lys
            260                 265                 270

Val Ser Ala Val Thr Leu Ala Tyr Leu Ile Phe Cys Leu Cys Ser Leu
    275                 280                 285

Val Gly Ile Leu His Leu Gln Arg Ala Leu Val Leu Arg Arg Lys Arg
    290                 295                 300

Lys Arg Met Thr Asp Pro Thr Arg Arg Phe Phe Lys Val Thr Pro Pro
305                 310                 315                 320

Pro Gly Ser Gly Pro Gln Asn Gln Tyr Gly Asn Val Leu Ser Leu Pro
                325                 330                 335

Thr Pro Thr Ser Gly Leu Gly Arg Ala Gln Arg Trp Ala Ala Gly Leu
                340                 345                 350

Gly Gly Thr Ala Pro Ser Tyr Gly Asn Pro Ser Ser Asp Val Gln Ala
            355                 360                 365

Asp Gly Ala Leu Gly Ser Arg Ser Pro Pro Gly Val Gly Pro Glu Glu
    370                 375                 380

Glu Glu Gly Glu Gly Tyr Glu Glu Pro Asp Ser Glu Glu Asp Ser Glu
385                 390                 395                 400

Phe Tyr Glu Asn Asp Ser Asn Leu Gly Gln Asp Gln Leu Ser Gln Asp
                405                 410                 415

Gly Ser Gly Tyr Glu Asn Pro Glu Asp Glu Pro Leu Gly Pro Glu Asp
            420                 425                 430
```

```
Glu Asp Ser Phe Ser Asn Ala Glu Ser Tyr Glu Asn Glu Asp Glu Glu
            435                 440                 445

Leu Thr Gln Pro Val Ala Arg Thr Met Asp Phe Leu Ser Pro His Gly
    450                 455                 460

Ser Ala Trp Asp Pro Ser Arg Glu Ala Thr Ser Leu Gly Ser Gln Ser
465                 470                 475                 480

Tyr Glu Asp Met Arg Gly Ile Leu Tyr Ala Ala Pro Gln Leu Arg Ser
                485                 490                 495

Ile Arg Gly Gln Pro Gly Pro Asn His Glu Glu Asp Ala Asp Ser Tyr
                500                 505                 510

Glu Asn Met Asp Asn Pro Asp Gly Pro Asp Pro Ala Trp Gly Gly Gly
            515                 520                 525

Gly Arg Met Gly Thr Trp Ser Thr Arg
            530                 535

<210> SEQ ID NO 34
<211> LENGTH: 538
<212> TYPE: PRT
<213> ORGANISM: Homo sapiens

<400> SEQUENCE: 34

Pro Glu Glu Pro Leu Val Val Lys Val Glu Glu Gly Asp Asn Ala Val
1               5                   10                  15

Leu Gln Cys Leu Lys Gly Thr Ser Asp Gly Pro Thr Gln Gln Leu Thr
            20                  25                  30

Trp Ser Arg Glu Ser Pro Leu Lys Pro Phe Leu Lys Leu Ser Leu Gly
        35                  40                  45

Leu Pro Gly Leu Gly Ile His Met Arg Pro Leu Ala Ile Trp Leu Phe
    50                  55                  60

Ile Phe Asn Val Ser Gln Gln Met Gly Gly Phe Tyr Leu Cys Gln Pro
65                  70                  75                  80

Gly Pro Pro Ser Glu Lys Ala Trp Gln Pro Gly Trp Thr Val Asn Val
                85                  90                  95

Glu Gly Ser Gly Glu Leu Phe Arg Trp Asn Val Ser Asp Leu Gly Gly
            100                 105                 110

Leu Gly Cys Gly Leu Lys Asn Arg Ser Ser Glu Gly Pro Ser Ser Pro
        115                 120                 125

Ser Gly Lys Leu Met Ser Pro Lys Leu Tyr Val Trp Ala Lys Asp Arg
130                 135                 140

Pro Glu Ile Trp Glu Gly Glu Pro Pro Cys Leu Pro Pro Arg Asp Ser
145                 150                 155                 160

Leu Asn Gln Ser Leu Ser Gln Asp Leu Thr Met Ala Pro Gly Ser Thr
                165                 170                 175

Leu Trp Leu Ser Cys Gly Val Pro Pro Asp Ser Val Ser Arg Gly Pro
            180                 185                 190

Leu Ser Trp Thr His Val His Pro Lys Gly Pro Lys Ser Leu Leu Ser
        195                 200                 205

Leu Glu Leu Lys Asp Asp Arg Pro Ala Arg Asp Met Trp Val Met Glu
    210                 215                 220

Thr Gly Leu Leu Leu Pro Arg Ala Thr Ala Gln Asp Ala Gly Lys Tyr
225                 230                 235                 240

Tyr Cys His Arg Gly Asn Leu Thr Met Ser Phe His Leu Glu Ile Thr
                245                 250                 255

Ala Arg Pro Val Leu Trp His Trp Leu Leu Arg Thr Gly Gly Trp Lys
```

```
                    260                 265                 270
    Val Ser Ala Val Thr Leu Ala Tyr Leu Ile Phe Cys Leu Cys Ser Leu
                275                 280                 285

Val Gly Ile Leu His Leu Gln Arg Ala Leu Val Leu Arg Arg Lys Arg
            290                 295                 300

Lys Arg Met Thr Asp Pro Thr Arg Arg Phe Phe Lys Val Thr Pro Pro
    305                 310                 315                 320

Pro Gly Ser Gly Pro Gln Asn Gln Tyr Gly Asn Val Leu Ser Leu Pro
                    325                 330                 335

Thr Pro Thr Ser Gly Leu Gly Arg Ala Gln Arg Trp Ala Ala Gly Leu
                340                 345                 350

Gly Gly Thr Ala Pro Ser Tyr Gly Asn Pro Ser Ser Asp Val Gln Ala
            355                 360                 365

Asp Gly Ala Leu Gly Ser Arg Ser Pro Pro Gly Val Gly Pro Glu Glu
        370                 375                 380

Glu Glu Gly Glu Gly Tyr Glu Glu Pro Asp Ser Glu Glu Asp Ser Glu
    385                 390                 395                 400

Phe Tyr Glu Asn Asp Ser Asn Leu Gly Gln Asp Gln Leu Ser Gln Asp
                    405                 410                 415

Gly Ser Gly Tyr Glu Asn Pro Glu Asp Glu Pro Leu Gly Pro Glu Asp
                420                 425                 430

Glu Asp Ser Phe Ser Asn Ala Glu Ser Tyr Glu Asn Glu Asp Glu Glu
            435                 440                 445

Leu Thr Gln Pro Val Ala Arg Thr Met Asp Phe Leu Ser Pro His Gly
        450                 455                 460

Ser Ala Trp Asp Pro Ser Arg Glu Ala Thr Ser Leu Ala Gly Ser Gln
    465                 470                 475                 480

Ser Tyr Glu Asp Met Arg Gly Ile Leu Tyr Ala Ala Pro Gln Leu Arg
                    485                 490                 495

Ser Ile Arg Gly Gln Pro Gly Pro Asn His Glu Glu Asp Ala Asp Ser
                500                 505                 510

Tyr Glu Asn Met Asp Asn Pro Asp Gly Pro Asp Pro Ala Trp Gly Gly
            515                 520                 525

Gly Gly Arg Met Gly Thr Trp Ser Thr Arg
        530                 535

<210> SEQ ID NO 35
<211> LENGTH: 31
<212> TYPE: PRT
<213> ORGANISM: Artificial Sequence
<220> FEATURE:
<223> OTHER INFORMATION: antibody fragment for MS analysis
<220> FEATURE:
<221> NAME/KEY: MISC_FEATURE
<222> LOCATION: (8)..(8)
<223> OTHER INFORMATION: X = S, P, A
<220> FEATURE:
<221> NAME/KEY: MISC_FEATURE
<222> LOCATION: (10)..(10)
<223> OTHER INFORMATION: X = G or A

<400> SEQUENCE: 35

Ser Ser Gln Ser Leu Glu Asn Xaa Asn Xaa Asn Thr Tyr Leu Asn Trp
1               5                   10                  15

Tyr Leu Gln Lys Pro Gly Gln Ser Pro Gln Leu Leu Ile Tyr Arg
            20                  25                  30

<210> SEQ ID NO 36
```

```
<211> LENGTH: 6
<212> TYPE: PRT
<213> ORGANISM: Mus musculus

<400> SEQUENCE: 36

Asn Ser Asn Gly Asn Thr
1               5

<210> SEQ ID NO 37
<211> LENGTH: 4
<212> TYPE: PRT
<213> ORGANISM: Mus musculus

<400> SEQUENCE: 37

Lys Phe Asn Gly
1

<210> SEQ ID NO 38
<211> LENGTH: 6
<212> TYPE: PRT
<213> ORGANISM: Artificial Sequence
<220> FEATURE:
<223> OTHER INFORMATION: humanized HVR-H2 fragment with N64Q mutation

<400> SEQUENCE: 38

Thr Glu Lys Phe Gln Gly
1               5

<210> SEQ ID NO 39
<211> LENGTH: 8
<212> TYPE: PRT
<213> ORGANISM: Artificial Sequence
<220> FEATURE:
<223> OTHER INFORMATION: humanized HVR-L2 fragment with S27eP mutation

<400> SEQUENCE: 39

Leu Glu Asn Pro Asn Gly Asn Thr
1               5

<210> SEQ ID NO 40
<211> LENGTH: 8
<212> TYPE: PRT
<213> ORGANISM: Artificial Sequence
<220> FEATURE:
<223> OTHER INFORMATION: humanized HVR-L2 fragment with S27eP/N28S
      mutation

<400> SEQUENCE: 40

Leu Glu Asn Pro Ser Gly Asn Thr
1               5

<210> SEQ ID NO 41
<211> LENGTH: 18
<212> TYPE: PRT
<213> ORGANISM: Artificial Sequence
<220> FEATURE:
<223> OTHER INFORMATION: linker

<400> SEQUENCE: 41

Gly Gly Ser Gly Gly Gly Gly Ser Gly Gly Gly Ser Gly Gly Gly
1               5                   10                  15

Gly Ser

<210> SEQ ID NO 42
<211> LENGTH: 15
<212> TYPE: PRT
```

<210> SEQ ID NO 42
<211> LENGTH: 15
<212> TYPE: PRT
<213> ORGANISM: Artificial Sequence
<220> FEATURE:
<223> OTHER INFORMATION: human transferrin receptor fragment

<400> SEQUENCE: 42

```
Ile Gly Gln Asn Met Val Thr Ile Val Gln Ser Asn Gly Asn Leu
1               5                   10                  15
```

<210> SEQ ID NO 43
<211> LENGTH: 15
<212> TYPE: PRT
<213> ORGANISM: Artificial Sequence
<220> FEATURE:
<223> OTHER INFORMATION: human transferrin receptor fragment

<400> SEQUENCE: 43

```
Asn Met Val Thr Ile Val Gln Ser Asn Gly Asn Leu Asp Pro Val
1               5                   10                  15
```

<210> SEQ ID NO 44
<211> LENGTH: 15
<212> TYPE: PRT
<213> ORGANISM: Artificial Sequence
<220> FEATURE:
<223> OTHER INFORMATION: human transferrin receptor fragment

<400> SEQUENCE: 44

```
Gln Ser Asn Gly Asn Leu Asp Pro Val Glu Ser Pro Glu Gly Tyr
1               5                   10                  15
```

<210> SEQ ID NO 45
<211> LENGTH: 32
<212> TYPE: PRT
<213> ORGANISM: Artificial Sequence
<220> FEATURE:
<223> OTHER INFORMATION: peptidic linker

<400> SEQUENCE: 45

```
Gly Gly Gly Gly Ser Gly Gly Gly Ser Gly Gly Gly Ser Gly
1               5                   10                  15

Gly Gly Ser Gly Gly Gly Ser Gly Gly Gly Ser Gly Gly
            20                  25                  30
```

<210> SEQ ID NO 46
<211> LENGTH: 118
<212> TYPE: PRT
<213> ORGANISM: Mus musculus

<400> SEQUENCE: 46

```
Glu Val Gln Leu Val Glu Ser Gly Gly Gly Leu Val Gln Pro Gly Asn
1               5                   10                  15

Ser Leu Thr Leu Ser Cys Val Ala Ser Gly Phe Thr Phe Ser Asn Tyr
            20                  25                  30

Gly Met His Trp Ile Arg Gln Ala Pro Lys Lys Gly Leu Glu Trp Ile
        35                  40                  45

Ala Met Ile Tyr Tyr Asp Ser Ser Lys Met Asn Tyr Ala Asp Thr Val
    50                  55                  60

Lys Gly Arg Phe Thr Ile Ser Arg Asp Asn Ser Lys Asn Thr Leu Tyr
65                  70                  75                  80

Leu Glu Met Asn Ser Leu Arg Ser Glu Asp Thr Ala Met Tyr Tyr Cys
                85                  90                  95

Ala Val Pro Thr Ser His Tyr Val Val Asp Val Trp Gly Gln Gly Val
            100                 105                 110
```

```
Ser Val Thr Val Ser Ser
        115

<210> SEQ ID NO 47
<211> LENGTH: 107
<212> TYPE: PRT
<213> ORGANISM: Mus musculus

<400> SEQUENCE: 47

Asp Ile Gln Met Thr Gln Ser Pro Ala Ser Leu Ser Ala Ser Leu Glu
1               5                   10                  15

Glu Ile Val Thr Ile Thr Cys Gln Ala Ser Gln Asp Ile Gly Asn Trp
            20                  25                  30

Leu Ala Trp Tyr Gln Gln Lys Pro Gly Lys Ser Pro Gln Leu Leu Ile
        35                  40                  45

Tyr Gly Ala Thr Ser Leu Ala Asp Gly Val Pro Ser Arg Phe Ser Gly
    50                  55                  60

Ser Arg Ser Gly Thr Gln Phe Ser Leu Lys Ile Ser Arg Val Gln Val
65                  70                  75                  80

Glu Asp Ile Gly Ile Tyr Tyr Cys Leu Gln Ala Tyr Asn Thr Pro Trp
                85                  90                  95

Thr Phe Gly Gly Gly Thr Lys Leu Glu Leu Lys
            100                 105

<210> SEQ ID NO 48
<211> LENGTH: 107
<212> TYPE: PRT
<213> ORGANISM: Artificial Sequence
<220> FEATURE:
<223> OTHER INFORMATION: L104V and L106I variant of SEQ ID NO: 57

<400> SEQUENCE: 48

Asp Ile Gln Met Thr Gln Ser Pro Ala Ser Leu Ser Ala Ser Leu Glu
1               5                   10                  15

Glu Ile Val Thr Ile Thr Cys Gln Ala Ser Gln Asp Ile Gly Asn Trp
            20                  25                  30

Leu Ala Trp Tyr Gln Gln Lys Pro Gly Lys Ser Pro Gln Leu Leu Ile
        35                  40                  45

Tyr Gly Ala Thr Ser Leu Ala Asp Gly Val Pro Ser Arg Phe Ser Gly
    50                  55                  60

Ser Arg Ser Gly Thr Gln Phe Ser Leu Lys Ile Ser Arg Val Gln Val
65                  70                  75                  80

Glu Asp Ile Gly Ile Tyr Tyr Cys Leu Gln Ala Tyr Asn Thr Pro Trp
                85                  90                  95

Thr Phe Gly Gly Gly Thr Lys Val Glu Ile Lys
            100                 105

<210> SEQ ID NO 49
<211> LENGTH: 122
<212> TYPE: PRT
<213> ORGANISM: Artificial Sequence
<220> FEATURE:
<223> OTHER INFORMATION: 299-023 VH humanization variant_DASG

<400> SEQUENCE: 49

Gln Ser Met Gln Glu Ser Gly Pro Gly Leu Val Lys Pro Ser Gln Thr
1               5                   10                  15

Leu Ser Leu Thr Cys Thr Val Ser Gly Phe Ser Leu Ser Ser Tyr Ala
            20                  25                  30
```

Met Ser Trp Ile Arg Gln His Pro Gly Lys Gly Leu Glu Trp Ile Gly
        35                  40                  45

Tyr Ile Trp Ser Gly Gly Ser Thr Asp Tyr Ala Ser Trp Ala Lys Ser
    50                  55                  60

Arg Val Thr Ile Ser Lys Thr Ser Thr Thr Val Ser Leu Lys Leu Ser
65                  70                  75                  80

Ser Val Thr Ala Ala Asp Thr Ala Val Tyr Tyr Cys Ala Arg Arg Tyr
            85                  90                  95

Gly Thr Ser Tyr Pro Asp Tyr Gly Asp Ala Ser Gly Phe Asp Pro Trp
            100                 105                 110

Gly Gln Gly Thr Leu Val Thr Val Ser Ser
        115                 120

<210> SEQ ID NO 50
<211> LENGTH: 110
<212> TYPE: PRT
<213> ORGANISM: Artificial Sequence
<220> FEATURE:
<223> OTHER INFORMATION: 299-009 VL humanization variant_NYA

<400> SEQUENCE: 50

Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Ala Trp Tyr Gln Gln Lys Pro Gly Lys Ala Pro Lys Leu Leu Ile
        35                  40                  45

Tyr Arg Ala Ser Thr Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Asn Tyr Ala Ser Ser Asn
            85                  90                  95

Val Asp Asn Thr Phe Gly Gly Gly Thr Lys Val Glu Ile Lys
            100                 105                 110

<210> SEQ ID NO 51
<211> LENGTH: 7
<212> TYPE: PRT
<213> ORGANISM: Oryctolagus cuniculus

<400> SEQUENCE: 51

Gly Phe Ser Leu Ser Ser Tyr
1               5

<210> SEQ ID NO 52
<211> LENGTH: 5
<212> TYPE: PRT
<213> ORGANISM: Oryctolagus cuniculus

<400> SEQUENCE: 52

Trp Ser Gly Gly Ser
1               5

<210> SEQ ID NO 53
<211> LENGTH: 17
<212> TYPE: PRT
<213> ORGANISM: Oryctolagus cuniculus

<400> SEQUENCE: 53

Arg Tyr Gly Thr Ser Tyr Pro Asp Tyr Gly Asp Ala Asn Gly Phe Asp
1               5                   10                  15

Pro

<210> SEQ ID NO 54
<211> LENGTH: 17
<212> TYPE: PRT
<213> ORGANISM: Artificial Sequence
<220> FEATURE:
<223> OTHER INFORMATION: 299-000 HVR-H3 DASG

<400> SEQUENCE: 54

Arg Tyr Gly Thr Ser Tyr Pro Asp Tyr Gly Asp Ala Ser Gly Phe Asp
1               5                   10                  15

Pro

<210> SEQ ID NO 55
<211> LENGTH: 17
<212> TYPE: PRT
<213> ORGANISM: Artificial Sequence
<220> FEATURE:
<223> OTHER INFORMATION: 299-000 HVR-H3 DAQG

<400> SEQUENCE: 55

Arg Tyr Gly Thr Ser Tyr Pro Asp Tyr Gly Asp Ala Gln Gly Phe Asp
1               5                   10                  15

Pro

<210> SEQ ID NO 56
<211> LENGTH: 11
<212> TYPE: PRT
<213> ORGANISM: Artificial Sequence
<220> FEATURE:
<223> OTHER INFORMATION: 299-000 HVR-L1 RAA

<400> SEQUENCE: 56

Arg Ala Ser Gln Ser Ile Ser Ser Tyr Leu Ala
1               5                   10

<210> SEQ ID NO 57
<211> LENGTH: 7
<212> TYPE: PRT
<213> ORGANISM: Oryctolagus cuniculus

<400> SEQUENCE: 57

Arg Ala Ser Thr Leu Ala Ser
1               5

<210> SEQ ID NO 58
<211> LENGTH: 12
<212> TYPE: PRT
<213> ORGANISM: Artificial Sequence
<220> FEATURE:
<223> OTHER INFORMATION: 299-000 HVR-L3 NYA

<400> SEQUENCE: 58

Gln Gln Asn Tyr Ala Ser Ser Asn Val Asp Asn Thr
1               5                   10

<210> SEQ ID NO 59
<211> LENGTH: 12
<212> TYPE: PRT
<213> ORGANISM: Artificial Sequence
<220> FEATURE:

<223> OTHER INFORMATION: sequence LC variant 0

<400> SEQUENCE: 59

Gln Ser Leu Glu Asn Ser Asn Gly Asn Thr Tyr Leu
1               5                   10

<210> SEQ ID NO 60
<211> LENGTH: 12
<212> TYPE: PRT
<213> ORGANISM: Artificial Sequence
<220> FEATURE:
<223> OTHER INFORMATION: sequence LC variant 1

<400> SEQUENCE: 60

Gln Ser Leu Glu His Ser Asn Gly Asn Thr Tyr Leu
1               5                   10

<210> SEQ ID NO 61
<211> LENGTH: 12
<212> TYPE: PRT
<213> ORGANISM: Artificial Sequence
<220> FEATURE:
<223> OTHER INFORMATION: sequence LC variant 2

<400> SEQUENCE: 61

Gln Ser Leu Glu Gln Ser Asn Gly Asn Thr Tyr Leu
1               5                   10

<210> SEQ ID NO 62
<211> LENGTH: 12
<212> TYPE: PRT
<213> ORGANISM: Artificial Sequence
<220> FEATURE:
<223> OTHER INFORMATION: sequence LC variant 3

<400> SEQUENCE: 62

Gln Ser Leu Glu Asn Ala Asn Gly Asn Thr Tyr Leu
1               5                   10

<210> SEQ ID NO 63
<211> LENGTH: 12
<212> TYPE: PRT
<213> ORGANISM: Artificial Sequence
<220> FEATURE:
<223> OTHER INFORMATION: sequence LC variant 4

<400> SEQUENCE: 63

Gln Ser Leu Glu Asn Val Asn Gly Asn Thr Tyr Leu
1               5                   10

<210> SEQ ID NO 64
<211> LENGTH: 12
<212> TYPE: PRT
<213> ORGANISM: Artificial Sequence
<220> FEATURE:
<223> OTHER INFORMATION: sequence LC variant 5

<400> SEQUENCE: 64

Gln Ser Leu Glu Asn Pro Asn Gly Asn Thr Tyr Leu
1               5                   10

<210> SEQ ID NO 65
<211> LENGTH: 12
<212> TYPE: PRT
<213> ORGANISM: Artificial Sequence
<220> FEATURE:
<223> OTHER INFORMATION: sequence LC variant 6

```
<400> SEQUENCE: 65

Gln Ser Leu Glu Asn Ser Gln Gly Asn Thr Tyr Leu
1               5                   10

<210> SEQ ID NO 66
<211> LENGTH: 12
<212> TYPE: PRT
<213> ORGANISM: Artificial Sequence
<220> FEATURE:
<223> OTHER INFORMATION: sequence LC variant 7

<400> SEQUENCE: 66

Gln Ser Leu Glu Asn Ser Asn Ala Asn Thr Tyr Leu
1               5                   10

<210> SEQ ID NO 67
<211> LENGTH: 12
<212> TYPE: PRT
<213> ORGANISM: Artificial Sequence
<220> FEATURE:
<223> OTHER INFORMATION: sequence LC variant 8

<400> SEQUENCE: 67

Gln Ser Leu Glu Asn Ser Asn Val Asn Thr Tyr Leu
1               5                   10

<210> SEQ ID NO 68
<211> LENGTH: 12
<212> TYPE: PRT
<213> ORGANISM: Artificial Sequence
<220> FEATURE:
<223> OTHER INFORMATION: sequence LC variant 9

<400> SEQUENCE: 68

Gln Ser Leu Glu Asn Pro Ser Gly Asn Thr Tyr Leu
1               5                   10

<210> SEQ ID NO 69
<211> LENGTH: 10
<212> TYPE: PRT
<213> ORGANISM: Artificial Sequence
<220> FEATURE:
<223> OTHER INFORMATION: sequence HC variant 0

<400> SEQUENCE: 69

Thr Glu Lys Phe Asn Gly Lys Ala Thr Leu
1               5                   10

<210> SEQ ID NO 70
<211> LENGTH: 10
<212> TYPE: PRT
<213> ORGANISM: Artificial Sequence
<220> FEATURE:
<223> OTHER INFORMATION: sequence HC variant 1

<400> SEQUENCE: 70

Thr Glu Lys Phe Gln Gly Arg Val Thr Met
1               5                   10
```